(12) United States Patent
Akasapu et al.

(10) Patent No.: US 12,097,178 B2
(45) Date of Patent: *Sep. 24, 2024

(54) METHODS OF EFFICIENTLY TREATING VITAMIN C DEFICIENCY-RELATED DISEASES AND OTHER CONDITIONS

(71) Applicant: Somerset Therapeutics, LLC, Hollywood, FL (US)

(72) Inventors: Prem Sagar Akasapu, Chesterfield, NJ (US); Veerappan Subramanian, Warren, NJ (US); Ilango Subramanian, Warren, NJ (US)

(73) Assignee: SOMERSET THERAPEUTICS, LLC, Hollywood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/064,222

(22) Filed: Dec. 9, 2022

(65) Prior Publication Data

US 2023/0181526 A1 Jun. 15, 2023

Related U.S. Application Data

(60) Provisional application No. 63/288,391, filed on Dec. 10, 2021.

(51) Int. Cl.
| | | |
|---|---|---|
| A61K 31/375 | (2006.01) | |
| A61K 9/00 | (2006.01) | |
| A61K 47/02 | (2006.01) | |
| A61K 47/26 | (2006.01) | |

(52) U.S. Cl.
CPC .......... *A61K 31/375* (2013.01); *A61K 9/0019* (2013.01); *A61K 47/02* (2013.01); *A61K 47/26* (2013.01)

(58) Field of Classification Search
CPC ............................ A61K 31/375; A61K 9/0019
See application file for complete search history.

(56) References Cited

U.S. PATENT DOCUMENTS

| | | | | |
|---|---|---|---|---|
| 2009/0232943 A1* | 9/2009 | Gamay | ................... | A23L 33/15 426/72 |
| 2018/0312903 A1* | 11/2018 | Grölz | ................. | C12N 15/1003 |

FOREIGN PATENT DOCUMENTS

| | | | |
|---|---|---|---|
| CN | 111803516 | * | 10/2000 |
| CN | 102247317 | | 11/2011 |
| CN | 102885771 | | 1/2013 |
| CN | 111803516 A | | 10/2020 |
| IN | 448045 | | 8/2023 |
| JP | 2012/140395 | * | 7/2012 |
| WO | WO 2000/066599 | * | 11/2000 |

OTHER PUBLICATIONS

Li et al. CN 111803516, published: Oct. 23, 2020, English machine translation obtained on Feb. 8, 2023. (Year: 2023).*
Zhang, JP 2012/140395, published: Jul. 26, 2012, , English machine translation obtained on Feb. 8, 2023. (Year: 2023).*
Chin et al. "Extended stability of ascorbic acid in 5% dextrose injection and 0.9% sodium chloride injection." Am J Health-Syst Pharm. 2005; 62: 1073-4. (Year: 2005), May 1, 2005, Chin, Alfred.
Final Office Action on Aug. 21, 2023 for U.S. Appl. No. 18/064,204, Kucharczk, Jed A.
Non-Final Office Action on Apr. 5, 2023 for U.S. Appl. No. 18/064,204, Kucharczk, Jed A.
McGuff Pharmaceutical, Inc. Ascor Product Label. "Highlights of Prescribing Information." Revised Jul. 2022. Published Oct. 21, 2022.
Yuan, Jian-Ping and Chen, Feng. "Degradation of Ascorbic Acid in Aqueous Solution." J. Agric. Food Chem. 1998, 46, 5078-5082. https://pubs.acs.org/doi/pdf/10.1021/jf9805404. Published on Web Nov. 21, 1998, Yuan, Jian-Ping.
Bayne A.C., "Five benefits of using antioxidants in pharma formulations," Pharmaceutical Manufacturer, published Oct. 6, 2022, Bayne, Anne-Cecile.
CD Formulations, "Antioxidants." (Year: 2023). Retrieved Nov. 21, 2023. https://www.formulationbio.com/products/antioxidants.html.
Fleming E, et al., "Co-delivery of synergistic antioxidants from food sources for the prevention of oxidative stress" Journal of Agriculture and Food Research, vol. 3, 2021, 100107. https://doi.org/10.1016/j.jafr.2021.100107. Published Feb. 2, 2021, Fleming, Erika.
Non-Final Office Action on Jan. 17, 2024 for U.S. Appl. No. 18/064,204, Kucharczk, Jed A.
Losada-Barreiro S, et al., "Biochemistry of Antioxidants: Mechanisms and Pharmaceutical Applications." Biomedicines. Nov. 25, 2022; 10(12):3051. doi: 10.3390/biomedicines10123051. PMID: 36551806; PMCID: PMC9776363, Losada-Barreiro, Sonia.
Pramanick S, et al. "Excipient Selection in Parenteral Formulation Development." Pharma Times, vol. 45, No. 3, Mar. 10, 2023, p. 69 (Mar. 10, 2013), Pramanick, Sougata.
Rowe R, et al., "Handbook of Pharmaceutical Excipients." Pharmaceutical Press, ISBN 978 1 58212 135 2, 6th Edition, 2009, p. 45 (Jan. 1, 2009), Rowe, Raymond C.

(Continued)

*Primary Examiner* — Genevieve S Alley
(74) *Attorney, Agent, or Firm* — Len S. Smith; Julie E. Kurzrok; Transformative Legal LLC

(57) ABSTRACT

The invention described here provides methods of efficiently treating vitamin C deficiency-related diseases and other conditions comprising the administration of pharmaceutical compositions comprising ascorbic acid compound(s), such as sodium ascorbate, and one or more pharmaceutically acceptable excipients (e.g., a carrier and optionally other agents, such as a tonicity agent, a chelator, or both). The methods comprise administration of such compositions in ready-to-use (RTU) form, provided in single unit dose packaging, wherein the compositions are stable when stored at 20° C. to 25° C.±2° C. for at least about 3 months. Compositions provided by the invention comprise an osmolality of between about 270 mOsm/kg to about 340 mOsm/kg and do not require dilution or further manipulation prior to use.

17 Claims, No Drawings

(56) References Cited

OTHER PUBLICATIONS

Shakeyla D, "Effectiveness of Antioxidants in Selected Model Drugs: Mitigation Strategy and Impact of Reformulation in Their Stability," United States Food and Drug Administration CDER, Jun. 15, 2023, Shakleya, Diaa.

Sheraz M, et al., "Stability and Stabilization of Ascorbic Acid a Review," Household and Personal Care Today vol. 10(3) May/Jun. 2015. Published Jun. 1, 2015, Sheraz, Muhammad Ali.

* cited by examiner

METHODS OF EFFICIENTLY TREATING VITAMIN C DEFICIENCY-RELATED DISEASES AND OTHER CONDITIONS

CROSS REFERENCE TO RELATED APPLICATIONS

This patent application claims priority to U.S. Provisional Application No. 63/288,391 filed Dec. 10, 2021, entitled "Methods of Efficiently Treating Vitamin C Deficiency-Related Diseases and Other Conditions." This application claims the benefit of priority to, and incorporates by reference the entirety of, this above-referenced priority application.

FIELD OF THE INVENTION

The invention primarily relates to injectable, ready-to-use pharmaceutical compositions comprising effective amounts of ascorbic acid compound(s), processes for manufacturing such compositions, and methods of using such compositions in preventing or treating conditions related to vitamin C deficiency, such as scurvy.

BACKGROUND OF THE INVENTION

Ascorbic acid, also known as vitamin C, is a critical compound to health, identified as an essential drug on the World Health Organization's List of Essential Medicines.

Ascorbic acid is chemically (2R)-2-[(1S)-1,2-Dihydydroxyethyl]-3,4-dihydroxy-2H-furan-5-one, having molecular formula is $C_6H_8O_6$ and following structural formula:

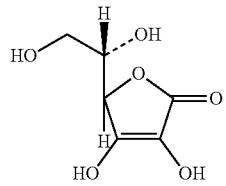

Ascorbic acid is an acid polyol containing 6 carbon atoms. The compound has acidic properties not provided by a carboxy group but from an enol, wherein hydroxyls in its C2 and C3 position very easily dissociate and discharge H+. Two types of ascorbic acid are found in nature: reduced L-ascorbic acid and oxidized dehydroascorbic acid. These two substances are reversible and provide much of the same or similar physiological activity. Ascorbic acid is typically sold, transported, and stored as a crystalline powder that is white in color, soluble in water, and stable under acid conditions.

Ascorbic acid is useful in the treatment of several diseases, conditions, or symptoms related to vitamin C deficiency, such as, e.g., nasal bleeding, hematuria, pigmentation (freckle, freckles), and certain skin diseases. Ascorbic acid can promote the formation of body gamma globulin, strengthen anti-infection ability (e.g., impact the immune system); participate in biological oxidation processes in vivo, aid in the synthesis of red blood cells, adrenocortical hormone(s), and neurotransmitter(s) etc. Further, ascorbic acid can participate in natural detoxification processes and prevent or reduce oxidation due to its antioxidant capacity and can promote heavy metal ion excretion, improve myocardial metabolism, strengthen tissue contractility, promote collagen fiber formation, and promote wound healing among other biological activity.

Ascorbic acid is specifically well known to be effective in the treatment and prevention of scurvy, a disease characterized by lack of sufficient consumption of vitamin C, resulting in physical weakness and fatigue, irritability, sadness, joint and/or limb pain, swollen and bleeding gums sometimes leading to tooth loss, and dermal effects such as red or blue spotting or bruising.

Pharmaceutical ascorbic acid is mainly available in oral tablet and injectable forms. Ascorbic acid is stable in dry conditions (e.g., is fairly stable in tablet form or dry powder form) but is easily oxidized in aqueous solution. The degradation of ascorbic acid has been considered one of the major causes of quality and color changes within pharmaceutical preparations during processing and storage of ascorbic acid in aqueous solution. The degradation processes of ascorbic acid are very complex, such processes containing a number of oxidation/reduction and inter-molecular rearrangement reactions. Dehydroascorbic acid, the oxidized form of ascorbic acid, is highly unstable in an aqueous solution, the compound being converted to a variety of degradation products, such as 2-furoic acid, 3-hydroxy-2-pyrone, 5-methyl-3,4-dihydroxytetrone, furfural, etc. (J. Agric. Food Chem. 1998, 46, 5078-5082). Oxidation of ascorbic acid is accelerated by heat, light, alkaline substances, copper or zinc, and oxidase, and, therefore, preparing a stable liquid composition of ascorbic acid, especially an aqueous composition for parenteral administration, with minimal degradation of drug is always challenging for pharmaceutical formulators.

Treatment of scurvy is often accomplished by administration of ascorbic acid by parenteral administration, most often by intravenous injection or continuous intravenous infusion. Ascorbic acid for the treatment of scurvy is commercially available as Ascor® (herein "Ascor®" or "ASCOR®" refers to the product approved under the United States Food and Drug Administration NDA number 209112 as of the first priority/filing date of this disclosure with the United States Patent and Trademark Office). Ascor® is a composition provided for intravenous administration, currently marketed by McGuff Pharmaceuticals, Inc. Ascor® is currently supplied in a pharmacy bulk package, wherein ascorbic acid is provided in a concentration of 500 mg/mL, requiring dilution prior to use, and wherein the product is administered under a pharmacy admixture program.

Each mL of Ascor® contains 500 mg of ascorbic acid, an amount equivalent to 562.5 mg of sodium ascorbate, hence comprising 65 mg sodium/mL of Ascor®. The largest recommended dosage for the Ascor® product is 200 mg for adults and pediatric patients 11 years and older and is even less for pediatric patients aged 1 year to less than 11 years (100 mg) and pediatric patients aged 5 months to less than 12 months (50 mg), hence any single container of Ascor® is unsuitable for administration to a single patient. Each mL of Ascor® further comprises 0.25 mg of edetate disodium. Ascor® is provided with a water carrier, however, as stated, Ascor® requires further dilution prior to use. Sodium hydroxide and sodium bicarbonate are added for pH adjustment (pH range 5.6 to 6.6). Ascor® contains no bacteriostatic or antimicrobial agent.

Ascor® injection is intended for dispensing of single doses from a single vial of Ascor® to multiple patients in a pharmacy admixture program and is restricted to the preparation of admixture for infusion. Per the Ascor® label, the bulk drug product should not be administered as an undiluted intravenous injection and, prior to administration, must be diluted in a suitable infusion solution. A suitable infusion solution per the product label is a 5% dextrose injection or sterile water for injection, each with added appropriate solutes, as necessary, to form an isotonic final solution. Once the closure system (vial) of Ascor® has been penetrated, all dispensing from the pharmacy bulk package vial must be completed within 4 hours. Any unused portion of Ascor® is then discarded.

Ascor® was first approved by the US FDA in 1947, and formulations of ascorbic acid for intravenous administration have not seemed to have advanced beyond the need for high-maintenance manipulation prior to use in the past 70 plus years. For example, even more recent products continue to require dilution prior to use, such dilution steps potentially leading to miscalculations in dosing, product contamination, or both. Ascorbic acid is also available in Europe and India as Ascorbic acid Injection 500 mg per 5 ml vial by Phoenix Labs and 100 mg/mL in 1.5 mL vial by Mankind Pharma. Ascorbic acid compositions are also described in, e.g., Zhanqi et al, CN 102247317 A, disclosing a vitamin C injection and a preparation method thereof, wherein the concentration of Vitamin C is 50% w/v, and wherein the composition(s) further comprise an antioxidant 0.1 to 0.3% w/v, a metal chelating agent in an amount of 0.01 to 0.05% w/v, sodium bicarbonate in an amount of 20 to 26% w/v, and water in an amount of 68 to 72% w/v.

Tang Xing et al, CN 102885771 A, discloses a vitamin C injectable solution, comprising vitamin C, ethylene diamine tetraacetic acid disodium salt, sodium metabisulfite, L-cysteine, sodium bicarbonate and water for injection, and further comprising sodium diethyldithiocarbamate, wherein the concentration of the vitamin C in the solution is 10.0 to 30.0 g/L, and the concentration of the sodium diethyldithiocarbamate is 0.4 to 1.0 g/L. Notably, the CN 102885771 A disclosure describes multiple ingredients providing a chelating effect, preservation effect, or both.

Providing high concentrations of ascorbic acid requiring dilution prior to use aids in the formulator's challenges in providing ascorbic acid in solubilized form. High concentration solutions of ascorbic acid are typical in parentally delivered products for treating scurvy, reflecting a view in the art that high concentrations of ascorbic acid are favorable or required in this context. Further complicating the convenient and efficient use of such products is their requirement for storage at refrigerated temperatures prior to use. For example, the Ascor® label and the Phoenix Labs ascorbic acid products both require storage in a refrigerator at 2° C. to 8° C. prior to use.

Clearly, the number of similarities between these products (high API concentration, refrigeration storage, etc.), spanning the course of over 70 years of use and possible development, reflects that producing a new effective parentally acceptable formulation of ascorbic acid is difficult, particularly products that are more convenient for patient and healthcare provider use. These facts evidence that developing effective alternative ascorbic acid compound products, e.g., injectable ascorbic acid compound products for the effective and efficient treatment of scurvy, requires application of inventive ingenuity.

CONSTRUCTION, TERMS, AND ACRONYMS

This section offers guidelines for reading this disclosure. The intended audience for this disclosure ("readers") are persons having ordinary skill in the practice of technologies discussed or used herein. Readers may also be called "skilled persons," and such technologies called "the art." Terms such as "understood," "known," and "ordinary meaning," refer to the general knowledge of skilled persons.

The term "uncontradicted" means not contradicted by this disclosure, logic, or plausibility based on knowledge of skilled persons.

Disclosed here are several different but related exemplary aspects of the invention (referred also to as, e.g., "cases," "facets," or "embodiments"). The invention encompasses all aspects, as described individually and as can be arrived at by any combination of such individual aspects. The breadth and scope of the invention should not be limited by any exemplary embodiment(s). No language in this disclosure should be construed as indicating any element/step is essential to the practice of the invention unless such a requirement is explicitly stated. Uncontradicted, any aspect(s) can be combined with any other aspect(s).

Uncontradicted, all technical/scientific terms used here generally have the same meanings as commonly understood by skilled persons, regardless of any narrower examples or descriptions provided here (including any term introduced initially in quotations). However, aspects characterized by the inclusion of elements, steps, etc., associated with specific descriptions provided here are distinct embodiments of the invention. Uncontradicted, disclosure of any aspect using known terms, which terms are narrowed by example or otherwise in this disclosure, implicitly discloses related aspects in which such terms are alternatively interpreted using the broadest reasonable interpretation of skilled persons.

Uncontradicted, "or" means "and/or" here, regardless of any occasional inclusion of "and/or" (e.g., phrases such as "A, B, or C" and "A, B, and/or C" simultaneously disclose aspects including (1) all of A, B, and C; (2) A and C; (3) A and B; (4) B and C; (5) only A; (6) only B; and (7) only C (and also support sub-groupings, such as "A or B," "A or C," etc.)).

Uncontradicted, "also" means "also or alternatively." Uncontradicted, "here" & "herein" mean "in this disclosure". The term "i.a." means "inter alia" or "among other things." "Also known as" is abbreviated "aka" or "AKA." "Elsewhere" means "elsewhere herein."

For conciseness, symbols are used where appropriate. E.g., "&" is used for "and," & "~" for "about." Symbols such as < and > are given their ordinary meaning (e.g., "≤" means "less than or equal to" & "≥" means "greater than or equal to"). A slash "/" can represent "or" ("A/B" means "A or B") or identify synonyms of an element, as will be clear from context.

The inclusion of "(s)" after an element or a step indicates that ≥1 of such an element is present, step performed, and the like. E.g., "element(s)" means both 1 element or ≥2 elements, with the understanding that each thereof is an independent aspect of the invention.

Use of the abbreviation "etc." (or "et cetera") in association with a list of elements/steps means any or all suitable combinations of the recited elements/steps or any known equivalents of such recited elements/steps for achieving the function(s) of such elements/steps that are known in the art. Terms such as "and combinations," or "or combinations" regarding listed elements/steps means any or all possible/suitable combinations of such elements/steps.

Aspects may be described as suitable for use(s) disclosed herein. Uncontradicted, terms such as "suitability" means acceptable or appropriate for performing a particular function/achieving particular state(s)/outcome(s), and typically means effective, practical, and non-deleterious/harmful in the context the term is used. E.g., uncontradicted, the term "suitable" means appropriate, acceptable, or in contexts sufficient, or providing at least generally or substantially all of an intended function, without causing or imparting significant negative/detrimental impact.

Uncontradicted, heading(s) (e.g., "Construction, Terms . . . ") and subheadings are included for convenience and do not limit the scope of any aspect(s). Uncontradicted, aspect(s), step(s), or element(s) described under one heading can apply to other aspect(s) or step(s)/element(s) here.

Ranges of values are used to represent each value falling within such range that are within an order of magnitude of the smallest endpoint of the range without having to explicitly write each value of the range. E.g., a recited range of 1-2 implicitly discloses each of 1.0, 1.1, 1.2, . . . 1.9, and 2.0 and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593).

Terms of approximation (e.g., "about,"~," or "approximately") are used (1) to refer to a set of related values or (2) where a precise value is difficult to define (e.g., due to limits of measurement). Uncontradicted, all exact values provided here simultaneously/implicitly disclose corresponding approximate values and vice versa (e.g., disclosure of "about 10" provides explicit support for the use of 10 exactly in such aspect/description). Ranges described with approximate value(s) include all values encompassed by each approximate endpoint, regardless of presentation (e.g., "about 10-20" has the same meaning as "about 10—about 20"). The scope of value(s) encompassed by an approximate term typically depends on the context of the disclosure, criticality or operability, statistical significance, understanding in the art, etc. In the absence of guidance here or in the art for an element, terms such as "about" when used in connection with an element should be interpreted as ±10% of the indicated value(s) and implicitly disclosing ±5%, ±2%, ±1%, and ±0.5%.

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of an element/step implicitly discloses corresponding use of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a composition comprising "an X" and "one or more Ys," the paragraph should be understood as providing disclosure of "one or more Xs" and "one or more Ys."

"Significant" and "significantly" mean results/characteristics that are statistically significant using ≥1 appropriate test(s)/trial(s) in the given context (e.g., p≤0.05/0.01). "Detectable" means measurably present/different using known detection tools/techniques. The acronym "DOS" (or "DoS") means "detectable(ly) or significant(ly)."

Uncontradicted, any value here that is not accompanied by a unit of measurement (e.g., a weight of 50 or a length of 20), any previously provided unit for the same element/step or the same type of element/step will apply, or, in cases where no such disclosure exists, the unit most commonly used in association with such an element/step in the art will apply.

Uncontradicted, the terms "including," "containing," "comprising," and "having" mean "including, but not limited to" or "including, without limitation." Uncontradicted, use of terms such as comprising and including regarding elements/steps means including any detectable number or amount of an element or including any detectable performance of a step/number of steps (with or without other elements/steps).

For conciseness, description of an aspect "comprising" or "including" an element, with respect to a collection/whole (e.g., a system, device, or composition), implicitly provides support for any detectable amount/number or ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the whole/collection being made up of the element, or essentially all of the whole/collection being made up of the element (i.e., that the collection consists essentially of the referenced element). Similarly, a method described as including a step with respect to an effect/outcome implicitly provides support for the referenced step providing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the effect/outcome, representing ≥~1%, ≥~5%, ≥~10%, ≥~20%, ≥~25%, ≥~33%, ≥~50%, ≥~51%, ≥~66%, ≥~75%, ~90%, ≥~95%, ≥~99%, or ~100% of the steps/effort performed, or both. Explicit listing of percentages of elements/steps in connection with aspects does not limit or contradict such implicit disclosure.

Uncontradicted, terms such as "comprising" when used in connection with a step of a method provide implicit support for performing the step once, ≥2 times, or until an associated function/effect is achieved.

Uncontradicted, the term "one" means a single type, single iteration/copy/thing, of a recited element or step, or both, which will be clear from context. For example, the referent "one" used with a component of a composition can refer to one type of element (which may be present in numerous copies, as in the case of an ingredient in a composition), one unit of the element, or both. Similarly, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a component of a composition/system).

The term "some" means ≥2 copies/instances or ≥5% of a listed collection/whole is, or is made up of, an element. Regarding methods, some means ≥5% of an effect, effort, or both, is made up of or is attributable to a step (e.g., as in "some of the method is performed by step Y") or indicates a step is performed ≥2 times (e.g., as in "step X is repeated some number of times"). "Predominately," "most," or "mostly," means detectably >50% (e.g., mostly comprises, predominately includes, etc., mean >50%) (e.g., a system that mostly includes element X is composed of >50% of element X). The term "generally" means ≥75% (e.g., generally consists of, generally associated with, generally comprises, etc., means ≥75%) (e.g., a method that generally consists of step X means that 75% of the effort or effect of the method is attributable to step X). "Substantially" or "nearly" means ≥95% (e.g., nearly all, substantially consists of, etc., mean ≥95%) (e.g., a collection that nearly entirely is made up of element X means that at least 95% of the elements in the collection are element X). Terms such as "generally free" of an element or "generally lacking" and element mean comprising ≤~25% of an element and terms such as "substantially free" of an element mean comprising ≤~5% of an element.

Uncontradicted, any aspect described with respect to an optionally present element(s)/step(s) also provides implicit support for corresponding aspect(s) in which one, some, most, generally all, nearly all, essentially all, or all of such element(s) are lacking/step(s) not performed, in respect of the relevant aspect. E.g., disclosure of a system comprising element X implicitly also supports a system lacking element X.

Uncontradicted, changes to tense or presentation of terms (e.g., using "comprises predominately" in place of "predominately comprises") do not change the meaning of the corresponding term/phrase.

Uncontradicted, all methods provided here can be performed in any suitable order regardless of presentation (e.g., a method comprising steps A, B, and C, can be performed in the order C, B, and A; B and A and C simultaneously, etc.). Uncontradicted, elements of a composition can be assembled in any suitable manner by any suitable method. In general, any methods and materials similar or equivalent to those described here can be used in the practice of embodiments. Uncontradicted, the use of ordinal numbers such as "first," "second," "third," etc. is to distinguish respective elements rather than to denote a particular order of those elements.

Uncontradicted, any elements, steps, components, or features of aspects and all variations thereof, etc., are within the scope of the invention.

Elements associated with a function can be described as "means for" performing a function in a composition/device/system or a "step for" performing a part of a method, and parts of this disclosure refer to "equivalents," which means equivalents known in the art for achieving a referenced function associated with disclosed mean(s)/step(s). However, no element of this disclosure or claim should be interpreted as limited to a "means-plus-function" construction unless such intent is clearly indicated by the use of the terms "means for" or "step for." Terms such as "configured to" or "adapted to" do not indicate "means-plus-function" interpretation, but, rather, describe element(s)/step(s) configured to, designed to, selected to, or adapted to achieve a certain performance, characteristic, property, etc. using teachings provided here or in the art.

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/incorporation of patent documents is limited to the technical disclosure thereof and does not reflect any view regarding the validity, patentability, etc., thereof. In the event of any conflict between this disclosure and the teachings of such documents, the content of this disclosure controls regarding aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

All original claims contained in this disclosure when filed are incorporated into this specification as if they were a part of the description.

Additional Terms, Concepts, and Acronyms

The following description of certain terms and acronyms is provided to assist readers in understanding the invention. Additional acronyms may be only provided in other parts of this disclosure and acronyms that are well known in the art may not be provided here.

Uncontradicted, any description of weight provided herein is weight percent by volume ("% w/v").

The term "composition" as used herein, is interchangeable with the word "formulation." Inventive "composition(s)" or "formulation(s)" described herein refer to preparations comprising an ascorbic acid compound in a form suitable for administration, e.g., parental administration, to a recipient, e.g., a mammal, specifically, e.g., a human patient/recipient. Compositions/formulations of the invention are typically pharmaceutically acceptable, meaning that they have been demonstrated to be safe and effective for pharmaceutical use in a number of mammalian recipients, typically humans, in connection with the treatment or prevention of one or more diseases/conditions (e.g., not resulting in an unacceptable level of adverse events with respect to US FDA standards or having issues in terms of safety, potency, quality, purity, stability, and the like, such as to not be deemed acceptable for pharmaceutical use under US FDA standards). Demonstrations of suitability can be made by, e.g., clinical development (e.g., according to one, two, or more well controlled and adequate clinical studies), bioequivalence to an already approved product, or a combination thereof.

Except where explicitly indicated or clearly indicated by context, "improved" herein means "increased." In aspects, "improved" means "reduced," such as with respect to the toxicity of a composition. Uncontradicted, terms such as "enhanced," "improved," and the like are used synonymously.

"Pharmaceutical suitability", "pharmaceutically suitable", "ophthalmologically suitable" or "ophthalmological suitability" are phrases typically used to refer to compositions that are safe and effective for pharmaceutical administration and application, having sufficient potency, purity, strength, quality, and safety for pharmaceutical application, in cases specifically to the eye, as may be judged by regulatory authority review, and as established by, e.g., one or more well controlled and adequate clinical studies performed in compliance with generally prevailing regulatory authority standards. Compositions described as "ophthalmologically suitable" should be interpreted to mean suitable for ophthalmic delivery when provided in a potency, purity, strength, or quality making it safe for ophthalmic use. Components described as "ophthalmologically suitable" should be interpreted in a similar manner. Uncontradicted, a description of "suitability" implicitly means that the referenced element, step, etc., is ophthalmologically/pharmaceutically suitable or otherwise medically suitable (e.g., safe and effective as determined by proper nonclinical/clinical testing).

Excipients herein are typically present in "effective amounts," and, uncontradicted, any described class of excipient or specific excipient is understood to be present in the associated composition/formulation in an effective amount, which generally means, in this context, an amount that is effective for the described function(s) associated with the excipient (it being understood that some excipient compound(s)/ingredient(s) exhibit more than one effect). E.g., a tonicity agent will be understood to be present in a composition/formulation in an amount that is effective to impart an indicated tonicity effect, a tonicity effect that is required for suitability of the composition, or an effect that imparts a significant tonicity effect on a composition (with respect to a comparator composition lacking the compound(s)/ingredient(s)).

In some cases, descriptions of terms and/or acronyms are repeated one or more times in the following portions of the disclosure to aid readability.

SUMMARY OF THE INVENTION

The inventions described and claimed herein have many attributes and aspects including, but not limited to, those set forth in, e.g., described or referenced in, this Summary. This Summary of the Invention ("Summary") is not intended to be all-inclusive, and the scope of the invention is not limited to or by the aspects, features, elements, or embodiments provided in this Summary, which is included for illustrative purposes only and not restriction. Any of the aspects described under this section can be combined with any other aspect described in this section or with any other aspect of this disclosure.

In certain aspects, the invention provides a method of treating a disease related to vitamin C deficiency. In aspects, the method comprises providing an injectable pharmaceutically acceptable composition in a container component, wherein the composition comprises an effective unit dose amount of an ascorbic acid compound component and one or more excipients. In aspects, the composition is contained in the container component in ready-to-use form. In aspects, the composition is maintained in the container component in ready-to-use form from the completion of the manufacturing process to the time of use. In aspects, the composition stored in ready-to-use form has an osmolality of about 270 mOsm/kg to about 340 mOsm/kg. In aspects, the composition in ready-to-use form is stable when stored at 20° C. to 25° C.±2° C. for at least 3 months prior to use. In aspects, the method comprises directly administering an effective amount of the formulation to a subject having a vitamin C deficiency by parenteral administration, such as, e.g., by injection or slow intravenous infusion. In aspects, the method comprises repeating administration for a number of times effective to treat a vitamin C deficiency in the subject.

According to certain embodiments, the invention provides a method of treating scurvy in an individual diagnosed with scurvy, the method comprising administration of a ready-to-use composition comprising an ascorbic acid compound component, wherein the composition has any one or more of the characteristics described above, such as, e.g., the composition is stable when stored at a temperature of 20° C. to 25° C.±2° C. for at least about 1 month, such as, e.g., about 1-3 months, about 1-6 months, about 1-9 months, about 1-12 months, or, e.g., about 1-18 or about 1-24 months or more prior to use. In specific aspects, the invention provides a method of treating scurvy in an individual diagnosed with scurvy, the method comprising administering an individually packaged dose of a composition provided in ready-to-use form, the composition having any one or more of the characteristics described above. In one specific aspect, the invention provides a method of treating scurvy in an individual, the method comprising administering an individually packaged dose of a composition provided in ready-to-use form, the composition comprising an ascorbic acid compound component present in the composition in a total amount of no more than about 400 mg, such as, e.g., no more than about 350 mg, about 300 mg, about 250 mg, about 200 mg, about 150 mg, about 100 mg, about 50 mg, or, e.g., in aspects no more than about 25 mg (e.g., about 10-100 mg, about 10-400 mg, about 10-250 mg, about 10-200 mg, about 25-250 mg, about 25-375 mg, about 25-125 mg, about 35-350 mg, about 50-400 mg, about 50-300 mg, about 50-250 mg, about 50-100 mg, or another range defined by specific values provided herein).

In some aspects, the invention provides a method of treating scurvy in a population of patients diagnosed with scurvy, wherein (a) the population of patients comprises at least 2 patients requiring a different total amount of ascorbic acid compound per dose; (b) the method comprises administering to each patient of the population of patients an individually packaged, ready-to-use, single dose of a composition comprising an ascorbic acid compound component, stable when stored at about 20° C. to 25° C.±2° C. for a period of at least 1 month, and (c) the method results in (I) an amount of waste of the ascorbic acid compound(s) which is detectably or significantly less than the amount of an ascorbic acid compound left unused with respect to treatment of scurvy in a similar population of patients with the product approved under the United States Food and Drug Administration NDA number 209112 (ASCOR®) (as of the filing/priority date of this disclosure—this limitation being generally applicable to references to ASCOR® herein); (II) a detectably or significantly reduced risk of administering to any single patient within a similar population of patients treated with the product approved under the United States Food and Drug Administration NDA number 209112 (ASCOR®) a total amount of ascorbic acid compound other than the intended total amount of ascorbic acid compound; or (III) a detectably or significantly reduced risk of contamination of the composition compared to a second composition approved under the United States Food and Drug Administration NDA number 209112 (ASCOR®) prior to the administration of ASCOR® for treating scurvy in a similar population of patients. In one aspect, the invention provides a method of treating scurvy in a patient diagnosed with scurvy with a ready-to-use composition comprising an ascorbic acid compound component, wherein the composition (a) is stable when stored at 20° C. to 25° C.±2° C. for at least one month prior to use, and (b) is provided in a single dose container entered a single time by a collection device when being administered to a patient.

In another aspect, the invention provides a method of treating vitamin C deficiency in an individual diagnosed with vitamin C deficiency, the method comprising administering an individually packaged dose of a composition comprising an ascorbic acid compound component provided in ready-to-use form, the composition having any one or more of the characteristics described above. In one specific aspect, the invention provides a method of treating a vitamin C deficiency in a patient, the method comprising administration of a ready-to-use composition comprising (a) an ascorbic acid compound component, (b) at least one of a chelation component, a tonicity component, or both, and (c) one or more additional excipients, wherein the composition is stable when stored between 20° C. to 25° C.±2° C. for at least one month. In another specific aspect, the invention provides a method of treating a vitamin C deficiency in a patient, the method comprising administration of a ready to use composition comprising (a) an ascorbic acid compound which is (I) present in an amount of less than 400 mg, (II) present in a concentration of no more than 50 mg/mL, or (III) both (I) and (II), (b) optionally at least one of a chelation component, tonicity component, or both and (c) one or more additional excipients, wherein the composition is stable when stored between 20° C. to 25° C.±2° C. for at least about one month. In aspects, the subject does not have a vitamin C deficiency, but, rather, the method described herein (or any other method described herein in connection with a particular condition, such as treatment of scurvy) (a) treats or prevents a disease or condition that is treatable/preventable by administration of an effective amount of the composition or (b) modulates a physiological state in a subject, such as a human patient, that is modulated by administration of an effective amount of the composition.

In alternative aspects, the invention provides a method of detectably or significantly decreasing the healing time of a wound in a mammal suffering therefrom, the method comprising administration of a composition comprising an ascorbic acid compound component, wherein the composition has any one or more of the characteristics described above or elsewhere in connection with compositions described here. In one specific aspect, the invention provides a method of detectably or significantly decreasing the healing time of a wound in a mammal suffering therefrom, the method comprising administering an individually packaged dose of a composition provided in ready-to-use form, the composition having any one or more of the characteristics described above or elsewhere. In another specific aspect, the invention provides a method of detectably or significantly decreasing the healing time of a wound in a mammal suffering therefrom, the method comprising administration of a ready-to-use composition comprising (a) an ascorbic acid compound component, (b) at least one of a chelation component, a tonicity component, or both, and (c) one or more additional excipients, wherein the composition is stable when stored between 20° C. to 25° C.±2° C. for at least about one month. In another specific aspect, the invention provides a method of detectably or significantly decreasing the healing time of a wound in a mammal suffering therefrom, the method comprising administration of a ready to use composition comprising (a) an ascorbic acid compound component which is (I) present in an amount of less than 400 mg, (II) present in a concentration of no more than 50 mg/mL, or (III) both (I) and (II), (b) at least one chelation agent, and (c) one or more additional excipients, wherein the composition is stable when stored between 20° C. to 25° C.±2° C. for at least about one month.

According to aspects, the invention provides ready-to-use (RTU) pharmaceutical compositions. In reference to the inventive composition(s) herein, ready-to-use should be interpreted as a pre-mixed pharmaceutical composition which does not require reconstitution or dilution before administration to a recipient. An RTU composition stands in contrast to pharmacy bulk pack composition(s) comprising ascorbic acid, such pharmacy bulk pack composition(s) requiring dilution prior to use, e.g., with a diluent and in a container selected by administering personnel. According to aspects, the invention provides RTU pharmaceutical compositions of ascorbic acid compounds (ASCC(s)). ASCC(s) refer(s) to ascorbic acid or any pharmaceutically acceptable derivatives thereof, such as, e.g., prodrugs, hydrates, salts, enantiomers, polymorphs, or solvates, of ascorbic acid.

According to aspects, the invention provides RTU pharmaceutical compositions comprising ASCC(s) provided as an ascorbic acid compound component (ASCC component) and one or more pharmaceutically acceptable excipients, wherein the composition can be stored at 20° C. to 25° C.±2° C. for at least one month, such as, e.g., at least about 2, about 3, about 6, about 9, about 12, or, e.g., at least about 18 or 24 months prior to use, and wherein the pharmaceutical composition is pharmaceutically acceptable when obtained from storage under suitable conditions and thereafter directly administered parenterally to a patient.

According to aspects, the invention provides RTU pharmaceutical compositions comprising an ASCC component and one or more pharmaceutically acceptable excipients, wherein the composition can be stored at 20° C. to 25° C.±2° C. for at least one month, such as, e.g., at least about 2, about 3, about 6, about 9, about 12, or, e.g., at least about 18 or 24 months prior to use. In aspects, the ready-to-use compositions do not require dilution prior to use, and, wherein without any further manipulation or preparation, the compositions comprise an osmolality of between about 270 mOsm/kg to about 340 mOsm/kg. In aspects, the composition(s) provided by the invention comprise ascorbic acid, e.g., L-ascorbic acid, or a derivative of ascorbic acid, such as, e.g., an ascorbic acid salt, such as, e.g., sodium ascorbate. In aspects, the RTU composition(s) comprise an ASCC component in a concentration of less than 50 mg/mL, such as, e.g., about 25 mg/mL. In aspects, composition(s) are provided in single unit dose packaging, wherein each single unit dose comprises an ASCC component present in a total amount of less than about 400 mg, such as, e.g., about 350 mg, about 250 mg, 200 mg, 150 mg, 100 mg, or, e.g., 50 mg. In aspects, the single unit dose packaging comprises a volume of composition of no more than about 10 mL, such as, e.g., no more than about 8 mL, about 6 mL, about 4 mL, or, e.g., in aspects, no more than about 2 mL. In aspects, an amount, e.g., the full amount, of composition single unit dose package is safe to administer to a single patient.

In aspects, the invention provides RTU composition(s) such as those described above, wherein the one or more pharmaceutically acceptable excipients is a chelation component. In aspects, the invention provides RTU pharmaceutical composition(s) wherein the ratio of the ascorbic acid compound component to the chelation component is less than about 1:0.00018, such as, e.g., between about 1:5 to about 1:0.04. In aspects, the chelation component comprises a single chelation agent. In aspects, the single chelation agent is edetate disodium.

In aspects, the invention provides RTU composition(s) such as those described above, wherein the one or more pharmaceutically acceptable excipients are contained in/form part of a tonicity component (one or more ingredients that are tonicity agent(s)). In aspects, the invention provides RTU pharmaceutical composition(s) wherein the ratio of the ascorbic acid compound component to the tonicity component is between about 1:50 to about 1:0.018. In other aspects, compositions lack a tonicity component.

In aspects, the invention provides RTU composition(s) such as those described above, wherein the composition(s) further or alternatively comprise one or more additional excipients, such as, e.g., excipients selected from stabilizing agent(s), buffer(s), pH adjusting agent(s), antioxidant(s), preservative(s), and carrier(s). In aspects, composition(s) provided by the invention comprise a buffer component. In aspects, composition(s) provided by the invention comprise a pH adjusting component. In aspects, the invention provides composition(s) which comprise water as a carrier, such that the composition(s) are characterizable as aqueous composition(s), or, e.g., more specifically, aqueous solutions (a composition/solution wherein water acts as a solvent, and that typically a composition/solution wherein most of any carrier component, such as generally all, essentially all, or all of any carrier is composed of water).

In aspects, the invention provides the RTU compositions described above, wherein the compositions are stable when stored at 20° C. to 25° C.±2° C. for a period of at least about 1 month, such as, e.g., about 2 months, about 3 months, about 6 months, about 12 months, or, e.g., about 18 or about 24 months prior to use (e.g., about 1-24 months, about 2-24 months, about 3-24 months, about 6-24 months, or about 12-24 months), as determined by, e.g., maintaining at least 90% of the initial amount of the ASCC component, assessment according to one or more United States Pharmacopeia (USP) defined measures of stability (such as, e.g., measures of stability described in the USP-National Formulary, version USP-NF 2021, Issue 3, dated Dec. 1, 2021,) or, e.g., earlier editions of the same (pre-dating the date of this Application) or (i.e., "and/or") comparison to one or more associated regulatory standards such as those established by the United States Food and Drug Administration (US FDA)), such as, e.g., assessments such as the particulate matter test under USP<788>, the pH test under USP<791>, the completeness of solution test under USP<641>, the visible particles test under USP <790>, impurity levels under USP<621>, total aerobic microbial count (TAMC) under USP<621>, total yeast and molds count (TYMC) under USP<621>, endotoxins under USP<85>, or sterility under USP<71>.

In aspects, the invention provides RTU, stable, pharmaceutical compositions comprising ascorbic acid compound(s) (in general, any such compositions comprise a pharmaceutically/therapeutically effective amount of such API(s)), one or more excipients such as, e.g., one or both of a chelation component and a tonicity component, which are suitable for intravenous administration, such as, e.g., intravenous injection or continuous intravenous infusion. In certain aspects, the RTU pharmaceutical composition(s) described herein comprise ascorbic acid compound(s) as the active ingredient, and one or more of a chelation component, a buffer component, a pH adjustment component, optionally one or more tonicity agents, and water. In aspects, the buffer component, pH adjustment component, or both comprise sodium bicarbonate, hydrochloric acid, sodium hydroxide, or a mixture thereof.

In one specific aspect, the invention provides a RTU pharmaceutical composition comprising (a) an ascorbic acid compound component in an amount of less than 50 mg/mL and (b) a chelation component, wherein the ratio of the ascorbic acid compound component to the chelation component is less than 1:0.00018, and wherein the composition can be stored at 20° C. to 25° C.±2° C. for at least one month prior to use. In one specific aspect, the invention provides a RTU pharmaceutical composition comprising (a) an ascorbic acid compound component in an amount of less than 50 mg/mL and (b) a single chelating agent, wherein the composition can be stored at 20° C. to 25° C.±2° C. for at least one month prior to use. In one specific aspect, the invention provides a RTU pharmaceutical composition comprising an ascorbic acid compound component (one or more ascorbic acid compound(s)), wherein the composition is provided in packaging comprising no more than 400 mg of the compound, and wherein the composition is capable of being stored at a temperature of 20° C. to 25° C.±2° C. for at least 1 month prior to use. In one specific aspect, the invention provides a RTU pharmaceutical composition for parenteral administration comprising (a) an ascorbic acid compound component in a concentration of about 1.0 mg/mL to about 35.0 mg/mL, (b) one or more tonicity agents in a concentration of about 0.1% w/v to about 5.0% w/v, (c) a chelation component in a concentration of about 0.001% w/v to about 0.1% w/v, (d) one or more buffers or pH-adjusting agents, and (e) a carrier. In aspects, similar compositions are provided lacking one or more of (b)-(d).

In one specific aspect, the invention provides a RTU pharmaceutical composition for parenteral administration, comprising (a) an ascorbic acid compound component in an amount of no more than about 400 mg, (b) one or more tonicity agents in an amount of no more than about 10- about 600 mg, (c) a chelation component in an amount of no more than about 0.1-10 mg, (d) one or more buffers or pH-adjusting agents, and (e) a carrier. In aspects, similar compositions are provided lacking one or more of (b)-(d).

In one specific aspect, the invention provides a ready-to-use pharmaceutical composition for parenteral administration comprising an ascorbic acid compound component, one or more tonicity agent(s), and one or more pharmaceutically acceptable excipients, wherein the composition can be stored for a period of at least 1 month at controlled room temperature in an airtight container without an increase in pressure within the container indicative of instability of the composition or component(s) thereof as measured by an appropriate United States Pharmacopeia defined test (e.g., such tests described herein, equivalents thereof, or substantially similar replacement or alternative tests known in the art). In aspects, the invention provides a RTU pharmaceutical composition comprising an ascorbic acid compound component for parenteral administration provided in single-use packaging, wherein the entire contents of the single-use packaging can be safely administered to a single patient, and wherein the single-dose packaging comprises no more than about 10 mL of composition.

In another specific aspect, the invention provides an injectable, RTU pharmaceutical composition comprising (a) a unit dose amount of an ascorbic acid compound component, (b) one or more excipients that are pharmaceutically suitable for an injectable ascorbic acid compound composition, wherein (c) the ready-to-use pharmaceutical composition has an osmolality of about 270 mOsm/kg to about 340 mOsm/kg, (d) the RTU pharmaceutical composition does not require dilution prior to administration to a patient, (e) the RTU pharmaceutical composition is stable according to United States Food and Drug Administration stability standards when stored at 20° C. to 25° C.±2° C. for at least 3 months prior to use, and (f) (I) the RTU pharmaceutical composition has been demonstrated to be effective in treating scurvy in a statistically significant population of scurvy patients when administered in an effective daily dose for a sufficient period, (II) the RTU pharmaceutical composition is bioequivalent to a second pharmaceutical composition, wherein the second pharmaceutical composition when administered to a population of scurvy patients results in a statistically significant number of the scurvy patients being effectively treated in one or more well controlled and adequate studies, or (III) both (I) and (II) are true.

According to certain embodiments, the invention provides a RTU pharmaceutical composition for the treatment of scurvy, wherein (a) the composition is manufactured by a process wherein all steps of the manufacturing process are performed under aseptic processing conditions; (b) the resulting product is stable when stored under wherein the composition can be stored at 20° C. to 25° C.±2° C. for at least about one month prior to use; and (c) the composition comprises any one or more additional characteristics described above or elsewhere in this disclosure. In certain aspects, the invention provides a ready-to-use pharmaceutical composition for the treatment of scurvy, wherein the composition is manufacture by (a) aseptically mixing a single chelating agent, an ascorbic acid compound, and optionally one or more tonicity agents with a sufficient amount of water to form a clear solution; (b) aseptically mixing one or more pH adjusting agents to establish a pH of about 5 to about 8; and (c) aseptically filling single-use containers with the resulting composition.

DETAILED DESCRIPTION OF THE INVENTION

For convenience, both combinations of components/elements/steps of compositions and methods of the invention and individual components/elements/steps may be described in this section of this disclosure. Despite the inclusion of passages focused on specific components/elements/steps, readers will understand that any suitable aspect, facet, embodiment, or other description of particular component(s), step(s) or element(s) can be applied to any general description of the compositions/methods of the invention, or any other recited component(s)/element(s)/step(s) thereof, which are provided in any part of this disclosure.

Compositions

In aspects, the invention provides ready-to-use (RTU) pharmaceutically suitable compositions comprising one or more ascorbic acid compounds (in pharmaceutically/therapeutically effective amount(s)) and, in facets, one or more excipients for aiding in storage or administration, e.g., aiding in parenteral administration of the composition. In aspects, such compositions are used in the prevention or treatment of one or more diseases, conditions, or symptoms related to vitamin C deficiency, such as scurvy. In aspects, compositions are compositions that have been demonstrated to have such effectiveness through clinical trials, bioequivalence to a reference product (such as ASCOR®), or a combination thereof.

Ascorbic Acid Compound (ASCC) Component
Ascorbic Acid Compounds

In aspects, compositions herein comprise an ascorbic acid compound (ASCC) component, comprising one or more ascorbic acid compounds (ASCCs). In aspects, an ASSC can be ascorbic acid or any pharmaceutically acceptable derivative of ascorbic acid, such as, e.g., any pharmaceutically acceptable prodrug, hydrate, salt, solvate, enantiomer, or polymorph of ascorbic acid. In aspects, an ASCC can be a natural ascorbic acid compound. In aspects, an ASCC can be a synthetic ascorbic acid compound.

In aspects, examples of ascorbic acid derivatives include one or more ascorbic acid prodrugs, e.g., ascorbic acid esters such as, e.g., ascorbyl palmitate (e.g., ascorbyl-6-palmitate), L-ascorbic acid diphosphate, ascorbyl-6-palmitate, prodrugs disclosed in, for example U.S. Pat. No. 9,550,744, etc., or combination(s) thereof. In aspects, examples of ascorbic acid derivatives include hydrate(s) of ascorbic acid, such as, e.g., hydrated species described by Bichara, et. al., in "Hydration of species derived from ascorbic acid in aqueous solution. An experimental and theoretical study by using DFT calculations," Journal of Molecular Liquids, Volume 181, May 2012, Pages 34-43, etc., or combination(s) thereof. In aspects, examples of ascorbic acid derivatives include salt(s) of ascorbic acid, including, e.g., sodium ascorbate, calcium ascorbate, potassium ascorbate, magnesium ascorbate, zinc ascorbate, molybdenum ascorbate, chromium ascorbate, manganese ascorbate, etc., salts of ascorbic acid derivatives, such as, e.g., magnesium ascorbyl phosphate, or combination(s) of any or all thereof. In aspects, examples of ascorbic acid derivatives include enantiomers of ascorbic acid, such as, e.g., the "l" isomer of ascorbic acid (l-ascorbic acid), the "d" isomer of ascorbic acid (d-ascorbic acid), or combination(s) thereof. In aspects, examples of ascorbic acid derivatives include polymorph(s) of ascorbic acid, including, e.g., those described by Arslantas, et. al., in, "Study of Polymorph Prediction For L-Ascorbic Acid," International Journal of Molecular Sciences, Volume 6, Dec. 6, 2005, Pages 291-302. In aspects, examples of ascorbic acid derivatives include solvates of ascorbic acid. A number of ascorbic acid derivatives have been developed in the art, with most tested to date for cosmetic/topical applications (see, e.g., Caritá, et al. Nanomedicine: Nanotechnology, Biology and Medicine, Volume 24, 2020, 102117, ISSN 1549-9634, doi.org/10.1016/j.nano.2019.102117), but with at least some references describing ascorbic acid derivatives proposed for use in injectable products (see, e.g., U.S. Ser. No. 10/039,767, EP0202589, and JP2016104708). Other similar disclosures of ascorbic acid derivatives are available in the art. In aspects, compositions can comprise any one or more such derivative(s) or combination of such derivative(s).

According to specific aspects, the compositions provided by the invention comprise one ASCC. In aspects, the ASCC is ascorbic acid. In alternative aspects, the ASCC is an ascorbic acid salt. In aspects, the ascorbic acid salt is a mineral ascorbate. In specific aspects, the mineral ascorbate is sodium ascorbate. In aspects, the ASCC, e.g., ascorbic acid or sodium ascorbate.

In aspects, only a single form of ASCC is present in composition(s) provided by the invention. In aspects, two or more forms of ASCC are present in composition(s), such as, e.g., both ascorbic acid and, e.g., sodium ascorbate. In aspects, the ASCC is the only vitamin compound present in the composition. In aspects, the ASCC(s) are the only pharmaceutically active ingredient(s) present in the composition. In aspects, one or more additional active pharmaceutical ingredients (APIs) can be present along with the ASCC(s).

Concentration/Amount

In aspects, compositions provided by the invention comprise an ASCC component comprising one or more ASCCs, such as, e.g., ascorbic acid or sodium ascorbate, wherein the concentration of the ASCC component in the composition is less than about 50 mg/mL, such as, for example, ≤~45 mg/mL, ≤~40 mg/ml, ≤~35 mg/mL, or, e.g., ≤~30 mg/mL. In aspects, compositions provided by the invention comprise one or more ASCCs, such as, e.g., ascorbic acid or sodium ascorbate, wherein the concentration of the ASCC(s) is about 1 mg/ml to about 50 mg/mL, such as, e.g., ~1-~45 mg/mL, ~1-~40 mg/mL, ~1-~35 mg/mL, ~1-~30 mg/mL, or ~1-~25 mg/mL, such as for example ~5-50 mg/ml, ~10-50 mg/mL, ~15-50 mg/mL, ~20-~50 mg/mL, or ~25-~50 mg/mL, as in, e.g., ~5-~45 mg/mL, ~10-~40 mg/mL, ~15-~35 mg/mL, or ~20-~30 mg/mL. In aspects, the concentration of the ASCC component (e.g., ASCC(s)) in the composition is about 25 mg/mL.

In aspects, the ASCC is a salt of ascorbic acid, e.g., sodium ascorbate, wherein the concentration of the ingredient can be described as an amount providing an equivalent amount of ascorbic acid. In aspects, the ASCC is sodium ascorbate, present in an amount of about 28.1 mg/mL, equivalent to about 25 mg/mL ascorbic acid. In aspects, sodium ascorbate is present in compositions provided by the invention in an amount of between about 1 mg/mL and about 56.2 mg/mL, wherein the equivalent amount of ascorbic acid is an amount of between about 1 mg/mL and 50 mg/mL. In aspects, the ASCC is sodium ascorbate in concentrations equivalent to the amounts of ascorbic acid described above, such amounts of sodium ascorbate calculated/adjusted as appropriate and demonstrated here.

In aspects, the invention provides a composition(s) comprising an ASCC component present in the composition(s) in a concentration of no more than about 50 mg/mL, such as, e.g., ≤~45 mg/ml, ≤~40 mg/ml, ≤~35 mg/mL, ≤~30 mg/ml, ≤~25 mg/mL, or, e.g., ≤~20 mg/mL. In aspects, the invention provides composition(s) packaged doses of composition provided in RTU form, each dose comprising an ASCC component present in a total amount of no more than about 500 mg, such as, e.g. no more than ~475 mg, ~450 mg, ~425 mg, ~400 mg, ~375 mg, ~350 mg, ~325 mg, ~300 mg, ~275 mg, ~250 mg, ~225 mg, or, e.g., ~200 mg, such as, e.g., no more than about 175 mg, ~150 mg, ~125 mg, ~100 mg, ~75 mg, or, e.g., ~50 mg, ~40 mg, ~30 mg, or, e.g., ~20 mg of an ASCC component.

In aspects, compositions provided by the invention are RTU compositions comprising (a) an ASCC, or, in specific aspects, an equivalent amount of ascorbic acid, in an amount of less than 50 mg/mL, such as, e.g., ~25 mg/mL, and (b) one or more excipients. Examples of such excipients are described here, and can include, e.g., one or more chelating agents, or, specifically, a single chelating agent. In aspects, compositions comprising one or more ASCCs and one or more excipients can be provided as an RTU composition which can be stored at controlled room temperature prior to use.

Excipients

According to aspects, compositions provided by the invention comprise one or more pharmaceutically acceptable excipients in addition to effective amount(s) of one or more ASCC(s). Herein, a "pharmaceutically acceptable excipient" should be interpreted as a pharmaceutically inactive component that is compatible with other ingredients of the composition; that is, the component does not cause such other components to be inactivated, become unstable, react to form undesirable reactants, significantly reduce its efficacy, etc. Herein, a "pharmaceutically acceptable excipient" is typically not detectably or significantly deleterious to the recipient of the composition or to the activity of the any API of the composition. Such excipients typically detectably or significantly improve one or more characteristics of the associated formulation/composition (e.g., delivery, stability, form, distribution of API, chemical characteristics of the composition, etc.). For example, a "pharmaceutically acceptable salt" references salt forms of the referenced compound prepared with counter ions non-toxic under the conditions of use, compatible with other ingredients of the composition, and not deleterious to the stability of the composition. Such references to "pharmaceutically acceptable" can be similarly applied herein to active ingredients, e.g., ASCCs.

According to aspects, compositions provided by the invention comprise one or more excipients which are suitable for delivery of the composition(s) by parenteral administration, such as, e.g., by injection, for example by intravenous administration.

In aspects, compositions provided by the invention comprise one or more pharmaceutically acceptable excipients selected from the group consisting of chelating agent(s), tonicity agent(s), stabilizing agents(s), antioxidant(s), preservative(s), buffering agent(s), pH-adjusting agent(s), and carrier(s). Examples of certain such agent(s) are described here. In aspects, such agents are provided as a "component", such as, e.g., a "chelation component" or a "tonicity component". Herein, a "component" should be interpreted as one or more ingredients sharing a function. For example, a "chelation component" can comprise one or more ingredients (e.g., the component comprising one or more ingredient constituents) providing a detectable or significant chelating effect; a "tonicity component" can comprise one or more ingredients/components providing a detectable or significant effect on the osmolality of the composition(s).

Chelation Component (Chelating Agent(s))

In aspects, compositions do not comprise any ingredient characterizable as a chelator/chelating agent (e.g., does not result in a chelation effect similar to those compounds in the art characterized as chelators or does not result in a significant chelation effect in a formulation/composition or in an environment in which a composition/formulation is used). In alternative aspects, compositions provided by the invention comprise an effective amount of a chelation component (comprising one or more chelator compound(s)). In aspects, the chelation component provides a detectable or significant chelation effect within the composition. In aspects, the chelation component comprises an effective amount of at least two chelation agents (e.g., ingredients characterizable as a chelator). In aspects, the chelation component comprises an effective amount of a single chelating agent/compound, or formulation/composition comprises a chelator component that mostly comprises, generally consists of, consists essentially of, substantially consists of, or consists of only a single chelating compound/ingredient.

In aspects, a chelation component detectably or significantly enhances stability of composition(s), detectably or significantly enhances preservation of compositions(s), detectably or significantly reduces the amount/number of impurities within a composition over a storage period, or any combination thereof. In aspects, compositions comprising a chelation component comprising one or more chelation constituents result in a composition which is stable under controlled room temperature storage conditions, e.g., compositions which retain at least about 95% (e.g., ≥~96%, ≥~97%, ≥~98%, or ≥~99%, of an ASCC of the composition when stored under standard storage conditions of about 25° C.±2° C. and about 60%±5% relative humidity, under accelerated conditions of about 40° C.±2° C. and about 75%±5% relative humidity, or both, for at least about 1 month, such as, e.g., ≥~2 months, ≥~3 months, ≥~6 months, ≥~9 months, or, e.g., ≥~12 months.

In aspects, the chelation component can comprise any pharmaceutically acceptable chelating agent. In aspects, such a chelating agent can be, e.g., cromolyn, or, e.g., a monomeric polyacid such as EDTA, cyclohexanediamine tetraacetic acid (CDTA), hydroxyethylethylenediaminetriacetic acid (HEDTA), diethylenetriaminepentaacetic acid (DTPA), dimercaptopropane sulfonic acid (DMPS), dimercapto succinic acid (DMSA), or aminotrimethylene phosphonic acid (ATPA), or pharmaceutically suitable and effective derivatives or analogs of any thereof or other related compounds, or suitable combinations of any or all thereof. In other aspects, a chelating agent can be a phosphate, such as, e.g., pyrophosphates, tripolyphosphates, and hexametaphosphates. In aspects, the chelation component can comprise a chelating antibiotic compound, such as, e.g., chloroquine and tetracycline. In aspects, the chelation component can comprise a nitrogen-containing chelating agent comprising two or more chelating nitrogen atoms within an imino group or in an aromatic ring (e.g., diimines, 2,2'-bipyridines, etc.), or, e.g., a polyamine such as cyclam (1,4,7,11-tetraazacyclotetradecane), N—(C1-C30 alkyl)-substituted cyclams (e.g., hexadecyclam, tetramethyl hexadecyl cyclam), diethylenetriamine (DETA), spermine, diethylnorspermine (DENSPM), diethylhomospermine (DEHOP), and deferoxamine (N'-[5-[[4-[[5-(acetylhydroxyamino) pentyl] amino]-1,4-dioxobutyl]hydroxyamino]pentyl]-N'-(5-aminopentyl)-N-hydroxybutanediamide; also known as desferrioxamine B and DFO). In aspects, a chelation component can comprise any one or more such chelating agents or pharmaceutically acceptable derivatives thereof. In aspects, a chelation component can comprise one or more other pharmaceutically acceptable chelating agents or pharmaceutically acceptable derivatives thereof known in the art.

In specific aspects, composition(s) provided by the invention comprise one or more pharmaceutically acceptable and suitable chelating agents characterizable as a monomeric polyacid. In aspects, the chelating agent comprises an ethylenediaminetetraacetic acid (EDTA) compound or a suitable EDTA salt such as, e.g., diammonium EDTA, disodium EDTA (edetate disodium), dipotassium EDTA, triammonium EDTA, trisodium EDTA, tripotassium EDTA, or calcium disodium EDTA. In aspects, compositions provided by the invention comprise a chelation component comprising a single chelation agent constituent. In aspects, the single chelation agent is edetate disodium.

In aspects, compositions provided by the invention comprise an effective amount of a chelation component. In aspects, the chelation component is present in compositions in an amount representing about 0.001% w/v to about 0.5% w/v of the composition, such as, e.g., ~0.001% w/v-~0.4% w/v, ~0.001% w/v-~0.3% w/v, ~0.001% w/v-~0.2% w/v, ~0.001% w/v-~0.1% w/v, or, e.g., ~0.001% w/v-~0.05% w/v. In aspects, the chelation component is present in compositions in an amount representing less than about 0.5% w/v of the composition, such as, e.g., ≤~0.4% w/v, ≤~0.3% w/v, ≤~0.2% w/v, ≤~0.1% w/v, ≤~0.05% w/v, ≤~0.04% w/v, ≤~0.03% w/v, ≤~0.02% w/v, ≤~0.01% w/v, or, e.g., ≤~0.005% w/v, ~0.001% w/v, or, e.g., ≤~0.0005% w/v, such as, e.g., in aspects the chelation component is present in compositions in an amount representing about 0.0005% w/v to about 0.15% w/v of the composition, such as, e.g., about 0.001% w/v of the composition. In aspects, the chelation component comprises a single chelation constituent. In aspects, the chelation component comprises only edetate disodium (disodium EDTA) in such disclosed amounts.

In this and any other ingredient aspect of the invention, the invention also can be characterized as comprising a "means" for providing a recited function, here imparting/providing an effective, detectable, or significant chelation effect to composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described chelation agents/compounds or components can be described as chelation means or means for providing effective, detectable, or significant chelation activity/characteristics to the composition).

Tonicity Component (Tonicity Agent(s))

In aspects, compositions do not comprise any ingredient characterizable as a tonicity agent. In aspects, compositions do not comprise any component characterizable as a tonicity component.

In alternative aspects, compositions provided by the invention comprise an effective amount of a tonicity component, comprising one or more compound(s)/ingredient(s)/agent(s) that exhibit a tonicity effect, are described herein as tonicity agents, or are recognized as a tonicity agent in the art. In aspects, the tonicity component provides a detectable or significant effect on the tonicity (e.g., as indicated by osmolality) of the composition(s). In aspects, the tonicity component comprises an effective amount of at least two tonicity agents (e.g., ingredients characterizable as capable of detectably or significantly modifying the tonicity of the composition(s)). In aspects, the tonicity component comprises an effective amount of a single tonicity agent. In aspects, most, generally all, essentially all, substantially all, or all of a tonicity component is a single agent/ingredient.

In aspects, compositions provided by the invention have a physiologically suitable tonicity such that no tonicity agent is required in order to facilitate safe administration of the composition(s). In aspects, the tonicity of the RTU compositions provided by the invention have a physiologically compatible tonicity. In aspects, the tonicity of the composition(s) provided by the invention is modified or modifiable by the concentrations of other component(s) present in the RTU composition(s) such that no specific tonicity agent is required to establish a physiologically compatible tonicity for the composition(s). In aspects, provided that the compositions are physiologically compatible, the compositions do not require any particular osmolality.

In aspects, a physiologically suitable tonicity characteristic of a composition/formulation is between about 270 mOsm/kg and about 340 mOsm/kg, such as, e.g., between about 270 mOsm/kg and about 300 mOsm/kg. In aspects, compositions have an osmolality of between about 270 mOsm/kg and about 340 mOsm/kg, e.g., between about 270 mOsm/kg and about 300 mOsm/kg without the addition of one or more tonicity agents.

In aspects, compositions provided by the invention comprise a tonicity component effective in establishing an osmolality of composition(s) of between about 270 mOsm/kg and about 340 mOsm/kg, such as, e.g., between about 270 mOsm/kg and about 300 mOsm/kg. In aspects, the presence of a tonicity component provides for composition(s) which are physiologically isotonic. In aspects, the presence of a tonicity component provides for composition(s) which are physiologically compatible with the osmotic pressure of body fluids such as blood and plasma.

In aspects, a tonicity component, when present, is present in the composition at the time of packaging; that is, in aspects, a tonicity component, when present, is present as a part of a RTU composition and is not added as a part of a dilution process or other process employed/required prior to use of the composition.

Typically, the RTU pharmaceutical compositions provided by the invention have a tonicity of between about 270 to about 340 mOsm/kg, such as, e.g., ~280 mOsm/kg-~340 mOsm/kg, ~290 mOsm/kg-~340 mOsm/kg, or ~300 mOsm/kg-~340 mOsm/kg, as in ~270 mOsm/kg-~330 mOsm/kg, ~270 mOsm/kg-~320 mOsm/kg, ~270 mOsm/kg-~310 mOsm/kg, or ~270 mOsm/kg-~300 mOsm/kg, such as, e.g., ~280 mOsm/kg-~330 mOsm/kg, ~280 mOsm/kg-~320 mOsm/kg, or, e.g., 290 to about 310 mOsm/kg. In aspects, such an osmolality is attained without the presence of a tonicity component. In aspects, such an osmolality is attained by the presence of a tonicity component comprising one or more tonicity agents.

In aspects, a tonicity agent can be any pharmaceutically acceptable tonicity agent. Suitable tonicity agents for use in the RTU compositions include, e.g., anhydrous or hydrous forms of sodium chloride, dextrose, sucrose, xylitol, fructose, glycerol, sorbitol, mannitol, potassium chloride, mannose, calcium chloride, magnesium chloride, other inorganic salts, etc. In other aspects, a tonicity agent can be, e.g., guanidine, magnesium chloride, maltose, etc. In aspects, a tonicity component can comprise sodium chloride, dextrose, or sodium chloride and dextrose.

In aspects, compositions provided by the invention comprise an effective amount of a tonicity component. In aspects, the tonicity component is present in compositions in an amount representing about 0.2% w/v to about 6% w/v (~2 mg/mL-~60 mg/mL) of the composition, such as, e.g., ~0.2% w/v-~5.5% w/v (~2 mg/mL-~55 mg/mL), ~0.2% w/v-~5% w/v (~2 mg/mL-~50 mg/mL), or ~0.2% w/v-~4.5% w/v (~2 mg/mL-~45 mg/mL). In other aspects, compositions of the invention comprise a tonicity component in an amount representing, e.g., ~0.2% w/v-~4% w/v (~2 mg/mL-~40 mg/mL), ~0.2% w/v-~3.5% w/v (~2 mg/mL-~35 mg/mL), ~0.2% w/v-~3% w/v (~2 mg/mL-~30 mg/mL), or, e.g., ~0.2% w/v-~2.5% w/v (~2 mg/mL-~25 mg/mL), such as, for example, ~0.5% w/v-~6% w/v (~5 mg/mL-~60 mg/mL) of a composition. Still other examples of suitable concentration ranges of tonicity agents for compositions of the invention can include, in aspects, ~1% w/v-~6% w/v (~10 mg/mL-~60 mg/mL), ~1.5% w/v-~6% w/v (~15 mg/mL-~60 mg/mL), ~2% w/v-~6% w/v (~20 mg/mL-~60 mg/mL), or, e.g., ~2.5% w/v-~6% w/v (~25 mg/mL-~60 mg/mL), as in, for example, ~0.5% w/v-~5.5% w/v (~5 mg/mL-~55 mg/mL), ~1% w/v-~5% w/v (~10 mg/mL-~50 mg/mL), ~1.5% w/v-~4.5% w/v (~15 mg/mL-~45 mg/mL), or, e.g., ~2% w/v-~4% w/v (~20 mg/mL-~40 mg/mL) of a composition.

In certain aspects, the tonicity component can comprise sodium chloride and dextrose in such a disclosed amount. In aspects, composition(s) provided by the invention comprise a tonicity component comprising sodium chloride, wherein the sodium chloride is present in an amount representing about 0.1% w/v to about 0.9% w/v (1 mg/mL to about 9 mg/mL) of the composition, such as, for example ~0.1% w/v-~0.8% w/v (~1 mg/mL-~8 mg/mL), ~0.1% w/v-~0.7% w/v (~1 mg/mL-~7 mg/mL), ~0.1% w/v-~0.6% w/v (~1 mg/ml-~6 mg/mL), ~0.1% w/v-~0.5% w/v (~1 mg/mL-~5 mg/mL), such as, e.g., ~0.2% w/v-~0.9% w/v (~2 mg/mL-~9 mg/mL), ~0.3% w/v-~0.9% w/v (~3 mg/mL-~9 mg/mL), ~0.4% w/v-~0.9% w/v (~4 mg/mL-~9 mg/mL), ~0.5% w/v-~0.9% w/v (~5 mg/mL-~9 mg/mL), or, e.g., ~0.2% w/v-~0.8% w/v (~2 mg/mL-~8 mg/mL), ~0.3% w/v-~0.7% w/v (~3 mg/mL-~7 mg/mL), or, e.g., ~0.4% w/v-~0.6% w/v (~4 mg/mL-~6 mg/mL) of the composition.

In aspects, composition(s) provided by the invention comprise a tonicity component comprising dextrose or an equivalent, wherein the dextrose/dextrose equivalent is present in an amount representing about 0.1% w/v to about 5% w/v (1 mg/mL to about 50 mg/mL) of the composition, such as, for example, ~0.1% w/v-~4.5% w/v (~1 mg/mL-~45 mg/mL), ~0.1% w/v-~4% w/v (~1 mg/mL-~40 mg/mL), ~0.1% w/v-~3.5% w/v (~1 mg/mL-~35 mg/mL), ~0.1% w/v-~3% w/v (~1 mg/mL-30 mg/mL), ~0.1% w/v-~2.5% w/v (1 mg/mL-~25 mg/mL), or ~0.1% w/v-~2% w/v (~1 mg/mL-~20 mg/mL). In alternative aspects, the amount of dextrose in a formulation/composition of the invention can range from, e.g., about (~)0.5% w/v-about (~)5% w/v (~5 mg/mL-~50 mg/mL), ~1% w/v-~5% w/v (~10 mg/ml-~50 mg/ml), ~1.5% w/v-~5% w/v (~15 mg/ml-~50 mg/ml), ~2% w/v-~5% w/v (~20 mg/mL-~50 mg/mL), or, e.g., ~2.5% w/v-~5% w/v (~25 mg/mL-~50 mg/mL), as in, for example, ~0.5% w/v-~4.5% w/v (~5 mg/mL-~45 mg/mL), ~1% w/v-~4% w/v (~10 mg/mL-~40 mg/mL), ~1.5% w/v-~3% w/v (~15 mg/mL-~30 mg/mL), or, e.g., ~2% w/v-~2.5% w/v (~20 mg/mL-~25 mg/mL) of the composition/formulation.

In this and any other ingredient aspect of the invention, the invention also can be characterized as comprising a "means" for providing a recited function, here imparting/providing an effective, detectable, or significant tonicity modification effect to composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described tonicity agents/compounds or components can be described as tonicity means or means for providing effective, detectable, or significant tonicity modification activity activity/characteristics to the composition).

Buffer Component (Buffers)

In aspects, compositions do not comprise any ingredient characterizable as a buffer. In alternative aspects, compositions comprise and effective amount of a buffer component. In aspects, a buffer component provides a detectable or significant buffering effect of the composition, such as, e.g., the ability of the composition to maintain a pH of between about 4 to about 8, such as, e.g., ~5.0-~7.0, or, e.g., ~5.5-~7.0, or, e.g., in specific aspects, a pH of about 5.6 to about 6.6. In aspects, a buffer component comprises a single buffering agent. In alternative aspects, a buffer component comprises two or more buffering agents.

In aspects, compositions provided by the invention comprise an effective amount of a buffer component. In aspects, the buffer component comprises one or more of any pharmaceutically acceptable buffers, including, e.g., pharmaceutically acceptable salts and acids of acetate, glutamate, citrate, tartrate, benzoate, lactate, histidine or other amino acids, gluconate, phosphate, malate, succinate, formate, propionate, and carbonate, etc. In aspects, a buffer component comprises sodium bicarbonate.

According to aspects, a buffer component can be present in composition(s) of the invention in an amount which provides a resulting composition capable of maintaining a pH of between about 4.0 to about 8.0, such as, e.g., between about 5.0 to about 7.0, e.g., about 5.5 to about 7.0, or, e.g., in specific aspects, a pH range of about 5.6 to about 6.6.

In aspects, the concentration of a buffer component in the composition is, e.g., about 0.00001% w/v to about 10% w/v (0.0001 mg/mL to about 100 mg/mL), ~0.0001% w/v-~10% w/v (~0.001 mg/mL-~100 mg/mL), ~0.001% w/v-~10% w/v (~0.01 mg/mL-~100 mg/mL), or ~0.01% w/v-~10% w/v (~0.1 mg/mL-~100 mg/mL). In alternative aspects, the concentration of a buffer component of a composition/formulation of the invention can be in a range such as about (~)0.1% w/v-about (~)10% w/v (~1 mg/mL-~100 mg/mL), ~1% w/v-~10% w/v (~10 mg/mL-~100 mg/mL), or ~5% w/v-~10% w/v (~50 mg/mL-~100 mg/mL), such as, e.g., 0.00001% w/v to about 5% w/v (~0.0001 mg/mL-~50 mg/mL), 0.00001% w/v to about 1% w/v (~0.0001 mg/mL-~10 mg/mL), 0.00001% w/v to about 0.1% w/v (~0.0001 mg/mL-~1 mg/mL), 0.00001% w/v to about 0.01% w/v (~0.0001 mg/mL-~0.1 mg/mL), 0.00001% w/v to about 0.001% w/v (0.0001 mg/mL-~0.01 mg/mL), or 0.00001% w/v to about 0.0001% w/v (~0.0001 mg/mL-~0.001 mg/mL).

In aspects, the buffer component of a composition can be described as, e.g., expressible as, a molar concentration. In aspects, compositions provided by the invention comprise a suitable buffer in a concentration of about 0.1 mM to 100 mM, such as, e.g., ~0.1 mM-~90 mM, ~0.1 mM-~80 mM, ~0.1 mM-~70 mM, ~0.1 mM-~60 mM, or ~0.1 mM-~50 mM, e.g., a buffer having a concentration of about ~1 mM-~100 mM, ~10 mM-~100 mM, ~20 mM-~100 mM, ~30 mM-~100 mM, ~40 mM-~100 mM, or, e.g., ~50 mM-~100 mM.

In this and any other ingredient aspect of the invention, the invention also can be characterized as comprising a "means" for providing a recited function, here imparting/providing an effective, detectable, or significant buffering capacity to composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described buffering agents/compounds or components can be described as buffering means or means for providing effective, detectable, or significant buffering capacity to the composition).

pH Adjusting Component (pH Adjusting Agents)

In aspects, the pH of pharmaceutical composition(s) provided by the invention can be adjusted using one or more pharmaceutically acceptable suitable pH adjusting agent(s). In aspects, a pH adjusting agent is added during the manufacturing process of the composition(s) to adjust the pH of the composition prior to final packaging. In aspects, compositions do not comprise any ingredient characterizable as a pH adjusting agent. In alternative aspects, compositions comprise an effective amount of a pH adjusting component. In aspects, a pH adjusting component provides a detectable or significant pH altering effect, such as, e.g., establishing a pH of composition(s) of about 4 to about 8, such as, e.g., ~5.0-~7.0 (5-7), or, e.g., ~5.5-~7.0, or, e.g., in specific aspects, a pH of about 5.6 to about 6.6. In aspects, a pH adjusting component comprises an effective amount of a single pH adjusting agent. In alternative aspects, a pH adjusting component comprises an effective amount of two or more pH adjusting agents.

In aspects, a pH-adjusting component establishes the pH of a composition between about 4 to about 8, (e.g., ~5.5-~7) which is maintained when the composition is stored at about 25° C.±2° C. and about 60%±5% relative humidity, under accelerated conditions of about 40° C.±2° C. and about 75%±5% relative humidity, or both, for a period of at least about 1 month, e.g., ≥~2 months, ≥~3 months, ≥~6 months, ≥~9 months, or, e.g., ≥~12 months.

In aspects, the pH-adjusting component can comprise any pharmaceutically acceptable pH adjusting agent. Herein, a "pH adjusting agent" is an acidifying or alkalizing agent used to significantly lower or raise the pH (potential hydrogen) of the composition to a target value. In aspects, a pH adjusting agent is an agent which, alone, is incapable of providing a buffering capacity of the composition. In aspects, a pH adjusting agent is not accompanied by a corresponding acid or base to provide a buffering capacity to the composition. In aspects, an acidifying pH adjusting agent is present to lower the pH, while an alkalizing agent is present to raise the pH to a target level. In aspects, an acidifying agent is characterizable as a strong acid. In aspects, an alkalizing agent is characterizable as a strong base. In aspects, a pH adjusting agent is added during the manufacturing process of the composition(s) to adjust the pH of the composition prior to final packaging. In aspects, a pH-adjusting component can comprise any suitable pH adjusting agent known in the art, such as, e.g., an acid such as a strong acid or, e.g., a base such as a strong base. In aspects, a pH-adjusting component can comprise an effective amount of only an acid. In aspects, a pH-adjusting component can comprise an effective amount of only a base. In aspects, a pH adjusting component can comprise an effective amount of both an acid and a base. In aspects, a pH-adjusting component can comprise a pH adjusting agent characterizable as a mineral acid, such as, e.g., sodium hydroxide (NaOH), hydrochloric acid (HCl), such as, e.g., about 1N NaOH or about 1N HCl (1N being the concentration of the agent added to the composition(s) to adjust the pH of the composition(s)). In aspects, a pH adjusting agent can be sodium carbonate or sodium bicarbonate. In aspects, a pH adjusting agent can be lactic acid or phosphoric acid. In aspects, compositions provided by the invention comprise a pH-adjusting component comprising a combination of pH adjusting agents selected from sodium hydroxide, hydrochloric acid, and sodium bicarbonate.

In aspects, one or more pH adjusting agent(s) (e.g., a pH-adjusting component) can be present in the compositions provided by the invention in an amount effective in providing the target pH. In aspects, such an amount can be considered a "trace amount," e.g., less than ~0.005% w/v, <0.004% w/v, <~0.003% w/v, <0.002% w/v, e.g., <~0.001% w/v. In aspects, such an amount can be an amount representing between about 0-about 0.01% w/v. In aspects, one or more pH adjusting agent(s) (e.g., present as a pH-adjusting component) can be present in the compositions provided by the invent ion in an amount effective in providing the target pH, such amounts representing between about 0-about 0.1% w/v, such as, e.g., about 0.01% w/v, ~0.02% w/v, ~0.03% w/v, ~0.04% w/v, ~0.05% w/v, ~0.06% w/v, ~0.07% w/v, ~0.08% w/v, or, e.g., ~0.09% w/v of the composition(s).

In this and any other ingredient aspect of the invention, the invention also can be characterized as comprising a "means" for effectively rendering composition(s) of the invention as having a pharmaceutically acceptable pH. In such a respect, any known equivalents of such named agents can also be, e.g., are, incorporated into compositions or methods of the invention. As with other sections similarly described herein, any of the components of the invention can be, where suitable, described as means for performing function(s) (e.g., the above-described pH adjusting agents/compounds or components can be described as pH adjusting means or means for effectively establishing a suitable target pH of the composition).

Preservative Component (Preservation Agents)

In aspects, compositions do not comprise any ingredient characterizable as a preservative. In alternative aspects, compositions provided by the invention comprise an effective amount of a preservative component. In aspects, the preservative component provides a detectable or significant preservative effect within the composition. In aspects, the preservative component comprises an effective amount of at least two preservation agents (e.g., ingredients characterizable as detectably or significantly contributing preservative effect). In aspects, the preservative component comprises an effective amount of a single preservation agent.

In aspects, a preservation component can comprise two or more preservation agents which each provide a different type of activity contributing to preservation of the composition(s). For example, a preservation component of compositions provided by the invention can comprise, e.g., a first preservation agent providing detectable or significant antimicrobial activity, and a second preservation agent providing detectable or significant chelation effect.

In aspects, a "preservative," or an ingredient demonstrating detectable or significant preservation effect, is a compound which detectably or significantly enhances stability of the composition(s), such as the stability of the ascorbic acid compound (e.g., ascorbic or sodium ascorbate), reduces the number(s)/amount(s) of detectable/significant impurities over the course of a storage (e.g., at least about 1, ~3, ~6, ~9, or at least about 12 months) under room temperature or accelerated storage conditions (e.g., about 25° C.±2° C. and about 60%±5% relative humidity, about 40° C.±2° C. and about 75%±5% relative humidity, or both), detectably or significantly reduces antimicrobial activity, or any combination of any or all thereof. In aspects, a preservation component can be present in composition(s) of the invention in an amount which detectably or significantly enhance stability of the composition(s), such as the stability of the ascorbic acid compound, reduces the amount of impurities, or any combination of any or all thereof, such as providing for a composition which is stable under room temperature storage conditions, e.g., providing for compositions which can retain at least 95% of the ascorbic acid compound when stored at controlled room temperature at about 25° C.±2° C. and about 60%±5% relative humidity, at accelerated conditions of about 40° C.±2° C. and about 75% 5% relative humidity, or both, for at least about one month such as ≥~2 months, ≥~3 months, ≥~6 months, ≥~9 months, or, e.g., ≥~12 months.

In aspects, the preservation component can comprise an effective amount of any pharmaceutically acceptable preservative agent. In aspects, such a preservative agent can be, e.g., hydrogen peroxide; sorbic acid; biguanides; quaternary ammonium salts such as benzalkonium chloride and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; and thiomersal, etc., or any pharmaceutically acceptable salts thereof, or combinations of any two or more such compounds, or equivalents thereof. In aspects, a chelating agent can also aid in extending the stability of a composition, and can, thus, be considered a preservation agent. In aspects, compositions comprise a preservation component which comprises at least one agent providing preservative effect which is not a chelating agent. In aspects, compositions do not comprise a preservation component which comprises an agent providing a preservative effect other than a chelating effect.

In aspects, compositions provided by the invention can comprise a preservative component comprising one or more anti-microbial preservative agents in effective amount(s) which can detectably or significantly inhibit microbial growth. In aspects, an "antimicrobial effective amount" of a preservative can be determined by performing preservative efficacy test(s) or antimicrobial effectiveness test(s) known in the art. In aspects, such tests are described in, e.g., chapter 51 of the United States Pharmacopeia 29-National Formulary 24 (USP 29-NF 24). In aspects, composition(s) provided by the invention can comprise one or more preservatives in an amount within the concentration ranges described in standard reference books like the most recent edition of Remington's Pharmaceutical Sciences and Handbook of Pharmaceutical Excipients or Handbook of Pharmaceutical Excipients. In aspects, compositions comprise a preservative component comprising one or more anti-microbial preservative agents in an amount representing between about 0.5 w/v % and about 4 w/v %, such as, e.g., ~0.5 w/v %-~3.5 w/v %, ~0.5 w/v %-~3 w/v %, ~0.5 w/v %-~2.5 w/v %, or ~0.5-~2 w/v %.

In aspects, compositions comprise a preservative component comprising one or more anti-microbial preservative agents in an amount representing between about 2 w/v % and about 6.3 w/v %, such as, e.g., ~2 w/v %-~6 w/v %, ~2 w/v %-~5.5 w/v %, ~2 w/v %-5 w/v %, ~2.5 w/v %-~4.5 w/v %, or, e.g., ~2.5-~4 w/v %, such as, e.g., between about 0.5 w/v %-about 6.3 w/v % of the composition In aspects, compositions comprise a preservative component comprising one or more chelating agents and one or more anti-microbial agents, wherein the preservative component is present in an amount representing between about 0.5% w/v and about 6.3% w/v of the composition, such as, e.g., ~0.5% w/v-~6% w/v, ~0.5% w/v-~5% w/v, ~0.5% w/v-~4% w/v, ~0.5% w/v-~3% w/v, ~0.5% w/v-~2% w/v, or ~0.5% w/v-~1% w/v, as in, e.g., ~0.6% w/v-~6.3% w/v, ~0.8% w/v-~6.3% w/v, or, e.g., ~1% w/v-~6.3% w/v of the composition.

In this and any other ingredient aspect of the invention, the invention also can be characterized as comprising a "means" for providing a recited function, here imparting/providing an effective, detectable, or significant preservation effect to composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described preservation agents/compounds or components can be described as preservation means or means for providing effective, detectable, or significant preservation activity/characteristics to the composition).

Carrier Component (Carrier Agents)

In aspects, compositions herein comprise a carrier component (a component that typically includes one or more compound(s)/ingredient(s) that serve to deliver the ascorbic acid compound(s) of the composition, to dilute such API, to arrive at a desired amount of composition, etc.), such a carrier component typically rendering the composition suitable for parenteral administration or, at least, being suitable for parenteral administration. In alternative aspects, compositions provided by the invention do not comprise a carrier component. In aspects, the carrier component provides a fluid, e.g., a liquid, character to the ready-to-use compositions herein. In aspects, the carrier maintains all constituents of the composition in solubilized form. In aspects, the composition is characterizable as a solution. Herein, the term "solution" refers to a typically clear, typically homogeneous, liquid dosage form containing at least one active pharmaceutical ingredient, e.g., at least one ascorbic acid compound (e.g., ascorbic acid or sodium ascorbate) dissolved in a solvent or mixture of mutually miscible solvents (e.g., water).

In aspects, the presence of a carrier component provides for a RTU composition. In aspects, the presence of a carrier component provides specifically for a ready-to-inject composition. In aspects, the presence of a carrier component provides for an RTU, ready-to-inject composition wherein all components are present in RTU, ready-to-inject concentrations.

In aspects, a carrier component comprises a combination of two or more carrier agents. In aspects, a carrier component comprises a single carrier agent. In aspects, a carrier component can comprise any pharmaceutically acceptable carrier. In aspects, a carrier component can comprise any pharmaceutically acceptable carrier (e.g., also referred to as a "vehicle") which does not cause a detectable or significant level of vascular irritation, thrombosis, or hemolysis. In aspects, the carrier component comprises any pharmaceutically acceptable carrier suitable for intravenous injection. In aspects, such carriers can include, e.g., water, or non-aqueous solvents, e.g., oils and alcohols, including organic solvents, such as, e.g., propylene glycol, polkyethylene glycols, ethanol, dimethyl sulfoxide, N-methyl-2-pyrrolidone, glycofurol, Solketal, glycerol formal, acetone, tetrahydrofurfuryl alcohol, diglyme, dimethyl isosorbide, ethyl lactate, arachic oil, cottonseed oil, almond oil, sesame oil, etc. In specific aspects, pharmaceutical compositions provided by the invention are aqueous (water-based) compositions, e.g., aqueous solutions, wherein the carrier is water, e.g., water for injection (WFI).

In aspects, the carrier component is present in an amount such that the total volume of an individually packaged dose of composition has a total volume of, e.g., about 1 mL, 2 mL, ~3 mL, ~4 mL, ~5 mL, ~6 mL, ~7 mL, ~8 mL, ~9 mL, or, e.g., ~10 mL.

In aspects, the carrier component is present in an amount which effectively maintains all composition constituents in solubilized form. In aspects, the carrier component is present in an amount which places all constituents of the composition(s) in RTU concentrations, e.g., ready-to-inject concentrations. In aspects, the invention provides RTU aqueous pharmaceutical compositions for parenteral administration, e.g., for intravenous administration, comprising ASCC(s), a chelating agent, one or more buffers or pH adjusting agents, optionally one or more tonicity agents, and water. In aspects, the invention provides a RTU pharmaceutical composition for parenteral administration comprising an ASCC in a concentration of about 1 mg/mL to about 35 mg/mL, a chelation component in a concentration of about 0.001% w/v to about 0.1% w/v, optionally a tonicity agent in a concentration of about 0.1% w/v to about 5% w/v, one or more buffers or pH adjusting agents, and a carrier, wherein the carrier maintains such constituents in such concentrations in ready-to-administer volumes of about 1 mL, ~2 mL, ~3 mL, ~4 mL, ~5 mL, ~6 mL, ~7 mL, ~8 mL, ~9 mL, or ~10 mL. In aspects, the carrier is water for injection in an amount representing at least about 50% w/v of the composition.

In aspects, a RTU pharmaceutical composition for parenteral administration is provided that comprises (a) an ASCC in an amount of no more than about 400 mg, (b) a chelation component in an amount of no more than about 0.1-10 mg, (c) optionally one or more tonicity agents in an amount of no more than about 10- about 600 mg, (d) one or more buffers or pH-adjusting agents, and (e) a carrier, wherein the carrier is a carrier capable of, and present in an amount capable of, maintaining such constituents in such amounts in solution for a period of at least about 1, ~3, ~6, ~9, or ~12 months when stored under standard conditions of under standard storage conditions of about 25° C.±2° C. and about 60%±5% relative humidity, under accelerated conditions of about 40° C.±2° C. and about 75%±5% relative humidity, or both.

In aspects, compositions provided by the invention are aqueous compositions. In aspects, compositions comprise at least 50% w/v water (e.g., water for injection), such as, e.g., ≥~55% w/v, ≥~60% w/v, ≥~65% w/v, ≥~70% w/v, ≥~75% w/v, ≥~80% w/v, ≥~85% w/v, or, e.g., ≥~90% w/v water.

In this and any other ingredient aspect of the invention, components of the invention also can be characterized as comprising a "means" for providing function(s), here effective, detectable, or significant carrier functionality for compounds of compositions, or effective, detectable, or significant carrier functionality to composition(s). In such a respect, any known equivalents of such named agents can also be, e.g., are, incorporated into compositions or methods of the invention. As with other sections similar described herein any of the components of the invention can be, where suitable, described as means (e.g., the above-described carrier agents/compounds/fluids (e.g., liquids) or components can be described as carrier means or means for providing effective, detectable, or significant carrier functionality/ characteristics to the composition).

Other Ingredients (API(s) & Excipients)

In aspects, the compositions provided by the invention can consist of or consist essentially of ASCC(s), a chelation component, a buffer component, optionally a tonicity component, optionally a pH-adjusting component, and a carrier. In aspects, compositions can comprise one or more other ingredients. In aspects, compositions can comprise one or more other ingredients, including pharmaceutically active- and non-active ingredients. In aspects, any additional ingredient(s) does not detectably or significantly negatively affect the stability of the compositions, such that compositions comprising any one or more additional ingredients maintain the ability to be stored at 25° C.±2° C. and about 60%±5% relative humidity, under accelerated conditions of about 40° C.±2° C. and about 75%±5% relative humidity, or both, for a period of at least about 1 months, ≥~3 months, ≥~6 months, ≥~9 months, or ≥~12 months, with at least about 95% (e.g., ≥~96%, ≥~97%, ≥~98%, or ≥~99%) of any ASCC of the composition being retained over such storage period(s).

In aspects, an added ingredient can be any ingredient enhancing the efficacy of the ASCC in relieving ascorbic acid (vitamin C) deficiency, providing one or more additional nutritional or general health benefits, or both. In aspects, compositions provided by the invention are parenterally administered compositions, and, accordingly, an additional additive is an additive administrable by parenteral administration, such as, e.g., by intravenous administration.

In certain aspects, compositions comprise one or more parenterally administrable nutrition additive(s). In aspects, the nutrition additive is a macronutrient, e.g., a protein or protein building blocks, carbohydrate, or fat). In aspects, the nutrition additive is a micronutrient, e.g., an electrolyte, vitamin, or trace mineral. In aspects, protein is provided as a pharmaceutically acceptable crystalline amino acid component of a composition. In aspects, such a crystalline amino acid component can comprise one or more essential amino acids (EAA(s)), one or more nonessential amino acids (NEAA(s)), or mixtures thereof. In aspects, carbohydrate(s) are provided as a pharmaceutically acceptable carbohydrate component of a composition. In aspects, a carbohydrate component can comprise any pharmaceutically acceptable carbohydrate, such as, e.g., dextrose. In aspects, lipid(s) are provided as a pharmaceutically acceptable lipid component of a composition. In aspects, a lipid component can comprise, e.g., soybean oil or, e.g., safflower plus soybean oil-based emulsions. In aspects, a lipid component can comprise primarily long-chain fatty acids, e.g., linoleic and linolenic acid. In aspects, such lipid components can comprise one or more other ingredients, such as, e.g., egg yolk phospholipids for emulsification. In aspects, a lipid component can comprise medium-chain triglycerides, olive oil, or both. In aspects, micronutrients are provided as a pharmaceutically acceptable micronutrient component of a composition. In aspects, a micronutrient component can comprise one or more electrolytes, such as, e.g., sodium, potassium, magnesium, calcium, phosphorus, chloride, acetate, etc.; vitamins, such as, e.g., vitamin A (e.g., retinol), vitamin B1 (thiamine), vitamin B2 (riboflavin), vitamin B3 (niacin), vitamin B5 (pantothenic acid), vitamin B6 (pyridoxine), vitamin B7 (vitamin H or biotin), vitamin B9 (folate/folic acid), vitamin B12 (e.g., cyanocobalamin), vitamin D (e.g., ergocalciferol), vitamin E (e.g., dl-alpha-tocopheryl acetate), vitamin K (e.g., phylloquinone), etc.; or, e.g., trace minerals, such as, e.g., chromium, copper, manganese, zinc, selenium, iodine, molybdenum, etc.

In this and any other ingredient aspect of the invention, components of the invention also can be characterized as comprising a "means" for providing function(s), here effective, detectable, or significant nutritional functionality for compounds of compositions, or effective, detectable, or significant carrier functionality to composition(s). In such a respect, any known equivalents of such named agents can also be, e.g., are, incorporated into compositions or methods of the invention. As with other sections similar described herein any of the components of the invention can be, where suitable, described as means (e.g., the above-described nutritional agents/compounds/fluids (e.g., liquids) or components can be described as nutritional means or means for providing effective, detectable, or significant nutritional functionality/characteristics to the composition).

In aspects, such components can be provided in any detectable, physiologically safe, physiologically effective, or significant amount, such as, e.g., in an amount similar or equivalent to a recommended daily amount for compounds where such recommended daily amounts have been established by an industry-recognized or governmental organization, such as, e.g., the United States Food and Drug Administration (FDA). In aspects, such components can be added in an amount which is a fraction of such a recommended daily amount, while in alternative aspects, such components can be added in an amount which higher than such a recommended daily amount, so long as any such amount is an amount known or demonstrated to be safe and effective and non-detrimental to the stability of the composition(s) or the stability or efficacy of any ASCC of the composition.

In aspects, compositions provided by the invention can comprise an ingredient provided in addition to any ASCC which is added to specifically address one or more health-related conditions or symptoms which may or may not be related to a deficiency in ascorbic acid (vitamin C). In aspects, one or more health-related conditions can be, e.g., digestive or digestive tract-related ailments or conditions, allergic symptoms, sleep ailments, pain, inflammation, or, e.g., conditions related to an addiction or addiction-related recovery. As non-limiting examples, compounds which may be added to compositions herein include one or more compounds related to digestive issues, such as, e.g., famotidine (reduction of stomach acid), metoclopramide (nausea, vomiting, heartburn, gastroesophageal reflux), ondansetron (nausea), etc.; or steroidal or non-steroidal anti-inflammatory agents such as ketorolac, etc. for pain or inflammation; antihistamines such as diphenhydramine, etc.

In aspects, compositions provided by the invention can comprise one or more excipients added to support the addition of (e.g., facilitate or allow for the successful addition and inclusion of) one or more such additionally added ingredients described here or, e.g., in aspects, to further enhance the efficacy or stability of any composition(s) described herein. In aspects, compositions can comprise, e.g., one or more surfactants (e.g., colfosceril palmitate, palmitic acid, poloxamer 188, polysorbate 20, polysorbate 80, sodium lauryl sulfate, tripalmitin, etc.); one or more lyoprotectants (e.g., dextran 40, glycine, lactose, mannitol, sucrose, trehalose, etc.); one or more stabilizers (e.g., albumin, protamine sulfate, zinc, etc.); one or more solubilizing agents (e.g., glycerin, polyethylene glycol 3350, polyethylene glycol 6000, sorbitol, etc.); one or more antioxidants (such antioxidants providing detectable or significant general oxidative stress reduction benefits, detectable or significant stabilization or protective benefit to one or more composition components, or both) (e.g., methionine, niacinamide, glutathione, etc.); one or more complexing agents (e.g., chelators described elsewhere herein or, e.g., calcium acetate, edetic acid, pentetic acid, stannous chloride, etc.); dispersing agents (e.g., carboxymethylcellulose sodium, hypromellose, proline, etc.); and antiadhesives, etc. In aspects other such additives or excipients can include, e.g., compound(s) which detectably or significantly enhance the bioavailability or efficacy of any ASCC (such as, e.g., flavonoids, bioflavonoids, etc.), vitamin C metabolites (such as, e.g., dehydroascorbate, calcium threonate, xylonate, lyxonate), lipid metabolites (e.g., lipid metabolites of lipid triglycerides and citrus bioflavonoids), cinnamic acid, petrolatum, phenylalanine, cyclodextrin, threonine, sodium sulfate, tranexamic acid, ursodiol, nicotinamide adenine dinucleotide (NAD+), amino acids such as taurine, or other compounds which are known in the art to be safely and effectively administered by parenteral administration and which are compatible with any ASCC(s) accompanying such compounds in compositions herein.

Compositions Do Not Include/Are Not Provided As

In certain aspects, composition(s) provided by the invention are characterizable by compound(s), ingredient(s), and the like, which are not present in the composition(s), or characteristics that are not attributable to compositions/formulations.

In certain aspects, compositions herein comprise an ASCC in an amount which is less than about 50 wt. %.

In certain aspects, composition(s) provided by the invention comprise a chelation component which does not comprise more than one chelation agent. In aspects, compositions comprise a single chelating agent. In aspects, compositions do not comprise an antioxidant. In aspects, compositions do not comprise sodium diethyldithiocarbamate. In aspects, compositions do not comprise both sodium diethylthiocarbamate and sodium metabisulphite. In aspects, compositions do not comprise sodium metabisulfphite. In aspects, compositions do not comprise sodium pyrosulfite. In aspects, compositions do not comprise sodium bisulfite. In aspects, compositions do not comprise cysteine hydrochloride. In aspects, compositions do not comprise L-cysteine. In aspects, compositions do not comprise sodium bicarbonate in an amount greater than about 5 wt. %, such as, e.g., not greater than about 4.5 wt. %, ≤~4 wt. %, ≤~3.5 wt. %, ≤~3 wt. %, ≤~2.5 wt. %, ≤~2 wt. %, or ≤~1.5 wt. %.

In certain aspects, composition(s) provided by the invention do not comprise a tonicity agent. In aspects, composition(s) provided by the invention are packaged in ready-to-use form. In aspects, composition(s) provided by the invention do not comprise a tonicity agent when in packaged form. In aspects, no tonicity agent is added to the composition prior to administration (such as, e.g., by the addition of a diluent comprising a tonicity agent). In aspects, composition(s) provided by the invention, when comprising a tonicity agent, comprise the tonicity agent when in packaged, ready-to-use form. In aspects, compositions comprise a tonicity agent and the product is provided in ready-to-use form, hence, such a tonicity agent is not added as, e.g., part of a dilution step, prior to administration to a recipient.

In certain aspects, compositions provided by the invention are not terminally sterilized as part of the manufacturing process. In certain aspects, compositions provided by the invention are not provided in a Pharmacy Bulk Package (PBP). In certain aspects, any single package of composition provided by the invention is not dispensed as single doses to multiple patients in a pharmacy admixture program. Terms such as "pharmacy bulk package" here refer to a container of a sterile preparation for parenteral use that contains a plurality of doses, e.g., multiple single doses. Herein, a "pharmacy admixture program" is the preparation of pharmaceutical product requiring the measured addition of a medication to a 50 mL or greater bag or bottle of IV (intravenous) fluid. In aspect, compositions provided by the invention are not restricted to the preparation of admixtures for infusion. In aspects, compositions provided by the invention do not require dilution prior to use. In aspects, compositions provided by the invention should not be diluted prior to use.

In aspects, compositions are provided in single use packaging. In aspects, each single use package is designed for single administration to a single patient. In aspects, compositions herein are packaged such that a single unit package cannot be used to administer composition(s) to multiple recipients.

Ratios

In aspects, compositions provided by the invention are characterizable by the ratios between components thereof.

In aspects, the invention provides a ready-to-use pharmaceutical composition comprising (a) an ascorbic acid compound (ASCC) component, and (b) a chelation component, wherein the ratio of the ASCC component to the chelation component is less than or equal to about 1:0.00018, such as, e.g., less than or equal to about 1:0.00027, ≤~1:0.00036, ≤~0.0004, ≤~1:0.00054, ≤~1:0.0009, ≤~1:0.0018, ≤~1:0.0054, ≤~1:0.08, ≤~1:0.09, ≤~1:1, e.g., ≤~1:2, ≤~1:3, or ≤~1:4, such as less than or equal to 1:5. In aspects, the invention provides a ready-to-use pharmaceutical composition comprising (a) an ascorbic acid compound (ASCC) component, and (b) a chelation component, wherein the ratio of the ASCC component to the chelation component is between 1:0.04 to about 1:0.0004, such as, e.g., ~1:0.03-~1:0.0004, ~1:0.02-~1:0.0004, or ~1:0.01-~1:0.0004, such as e.g., ~1:0.005-~1:0.0004.~1:0.004-~1:0.0004, ~1:0.002-~1:0.0004, or ~1:0.001-~1:0.0004. Other exemplary ratios of the ASCC component to the chelation component are, for example, ~1:0.04-~1:0.0008, ~1:0.04-~1:0.0007, ~1:0.04-~1:0.0006, or e.g., ~1:0.04-~1:0.0005.

In aspects, the invention provides a ready-to-use pharmaceutical composition comprising (a) an ASCC component in an amount of less than 50 mg/mL, and (b) a chelation component, wherein the ratio of the ASCC component to the chelation component is less than 1:0.0004, and wherein the composition can be stored at 20° C. to 25° C.±2° C. for at least one month prior to use.

In aspects, the invention provides a ready-to-use pharmaceutical composition comprising (a) an ascorbic acid compound (ASCC) component, and (b) a tonicity component, wherein the ratio of the ASCC component to the tonicity component at any time after manufacturing (e.g., at any time during storage and prior to the administration of the composition), is less than or equal to about 1:0.018, such as, e.g., than or equal to about 1:0.027, ≤~1:0.036, ≤~1:0.054, ≤~1:0.09, ≤~1:0.18, ≤~1:0.54, ≤~1:1, ≤~1:2, ≤~1:4, ≤~1:6, ≤~1:8, ≤~1:10, ≤~1:15, ≤~1:20, or, e.g., ≤~1:25, ≤~1:30, ≤~1:35, ≤~1:40, or ≤1:45, such as less than or equal to 1:50.

In aspects, the ratio of the ASCC component to the tonicity component in the composition is between about 1:2 to about 1:0.04, such as, e.g., ~1:1.5-~1:0.04, ~1:1-~1:0.04, ~1:0.9-~1:0.04, ~1:0.8-~1:0.04, ~1:0.7-~1:0.04, ~1:0.6-~1:0.04, ~1:0.5-~1:0.04, ~1:0.4-~1:0.04, ~1:0.3-~1:0.04, ~1:0.2-~1:0.04, such as, e.g., ~1:0.1-~1:0.04. Other exemplary ratios of ASCC component to the tonicity component are, for example, ~1:0.4-~1:0.08, or, e.g., ~1:0.4-~1:0.05. According to certain alternative aspects, the invention provides a ready-to-use pharmaceutical composition comprising an ASCC component and no tonicity component such that such a ratio of ASCC component to tonicity component is not present.

In aspects, the invention provides a ready-to-use pharmaceutical composition comprising (a) an ASCC component in an amount of less than 50 mg/mL, and (b) a tonicity component, wherein the ratio of the ASCC component to the tonicity component is less than 1:3, and wherein the composition can be stored at 20° C. to 25° C.±2° C. for at least one month, e.g., ≥3 months, ≥6 months, ≥9 months, or, e.g., ≥12 months, prior to use.

In aspects, the invention provides a ready-to-use pharmaceutical composition comprising (a) an ASCC component in an amount of less than 50 mg/mL, (b) a chelation component, wherein the ratio of the ASCC component to the chelation component is less than 1:0.04, and (c) a tonicity component, wherein the ratio of the ASCC component to the tonicity component is less than 1:3, and wherein the composition can be stored at 20° C. to 25° C.±2° C. for at least one month, e.g., ≥3 months, ≥6 months, ≥9 months, or, e.g., ≥12 months, prior to use.

In aspects, any component(s) or compound(s)/agent(s) described herein can be present in composition(s) in therapeutically effective amount(s), compositionally compatible amount(s), or both. In aspects, any single component or compound/agent provided herein can be present in a relationship with, such as, e.g., in a ratio with, any one or more other single component or compound/agent. In aspects, any combination of component(s) or compound(s)/agent(s) provided herein can be present in a ratio with any other combination of component(s) or compound(s)/agent(s). In aspects, ratio(s) between such component(s) or compound(s)/agent(s) or compositions thereof can be established using any provided amounts for each disclosed herein, including, e.g., values within ranges of such amounts disclosed herein.

Additional Means/Steps for Performing Functions

In aspects, compositions provided by the invention comprise one or more means for performing one or more specific functions and methods of the invention include steps for performing functions. In general, any element described herein as a "means" for performing a function can also, wherever suitable, serve as a "step for" performing a function in the context of methods of the invention, and vice versa. E.g., a component described herein as a means for preserving a composition also simultaneously and implicitly supports a method of making such a composition comprising a step of preserving a composition and a kit comprising a means for delivering a composition implicitly and simultaneously provides a step for delivering the composition comprising the use of such delivery means.

In one aspect, compositions provided by the invention comprise means for adjusting or establishing the tonicity of compositions, such means for establishing a target tonicity (or osmolality) of a composition detectably or significantly modifying the tonicity of the composition ("tonicity means"). Support for tonicity means can be found in, e.g., the section herein titled, "tonicity component."

In one aspect, compositions provided by the invention comprise means for maintaining the pH of compositions within a target range, such means for maintaining a target pH range of a composition detectably or significantly providing a buffering capacity of the composition ("buffer means"). Support for buffer means can be found in, e.g., the section herein titled, "buffer component."

In one aspect, compositions provided by the invention comprise means for adjusting or establishing the pH of compositions, such means for establishing a target pH of a composition detectably or significantly modifying the pH of the composition ("pH adjusting means"). Support for pH means can be found in, e.g., the section herein titled, "pH adjusting component."

In one aspect, compositions comprise means for preserving the composition(s), e.g., detectably or significantly inhibit microbial growth, detectably or significantly reducing the number of impurities or detectably or significantly improving the stability of the compositions such that compositions remain safe and suitable for administration after storage of at least about 1 month, e.g., ~2 months, ~3 months, ~6 months, ~9 months, or ~12 months, or more after manufacturing at about 25° C.±2° C. and about 60%±5% relative humidity, under accelerated conditions of about 40° C.±2° C. and about 75%±5% relative humidity, or both.

Composition Characteristics
Ready-to-Use (RTU)

In aspects, compositions of the invention are characterizable as ready-to-use (RTU), i.e., in being ready for use without significant modification to the composition, e.g., does not need any dilution prior to administration. In aspects, RTU formulations are present in dosage amounts, or containers/packages comprising typical unit dosage amounts.

Pharmaceutical compositions in the form of ready-to-use intravenous solutions comprising ascorbic acid or a pharmaceutically acceptable salt thereof are described herein. Typically, a stable ready-to-use liquid compositions comprising ascorbic acid or a pharmaceutically acceptable salt thereof, one or more tonicity agents and one or more pharmaceutically acceptable excipients, which does not need any dilution prior to administration and can be stored at controlled room temperature.

In one general aspect, there is provided a stable ready-to-use pharmaceutical composition of ascorbic acid or a pharmaceutically acceptable salt thereof, wherein the composition does not need any dilution prior to administration.

pH

In aspects, composition(s) provided by the invention have a physiologically suitable pH. In aspects, composition(s) provided by the invention have a pH suitable for parenteral administration, such as, e.g., by intravenous administration. In aspects, composition(s) typically have a pH within the range from about 5 to about 8, such as, e.g., a pH of ~5-~7.5, ~5-~7, or ~5-~6.5, such as, e.g., ~5.5-~8, ~6-~8, or ~6.5-~8, such as, e.g., ~5.5-~7.5, ~5.5-~7, ~5.5-~6.5, or, e.g., ~5.6-~6.6.

In one aspect, the invention provides ready-to-use pharmaceutical composition(s) of ASCC(s) for parenteral administration comprising an ASCC component, optionally a tonicity component, and one or more pharmaceutically acceptable excipients, wherein the composition requires no dilution before administration, has a pH from about 5.0 to about 8.0, about 5.0 to about 7.0, or about 5.5 to about 7.0, and can be stored at controlled room temperature for a period of at least 1 month, such as, e.g., at least about 2, ~3, ~6, ~9, or ~12 months prior to administration.

Osmolality

In aspects, composition(s) provided by the invention have a physiologically suitable osmolality. In aspects, composition(s) are hypotonic. In aspects, composition(s) are hypertonic. In aspects, composition(s) are isotonic. In certain aspects, composition(s) provided by the invention are isotonic with blood. In aspects, composition(s) have a tonicity such that the osmolality of composition(s) is about 270-340 mOsmol/kg, such as, for example ~270-~335 mOsmol/kg, ~270-~330 mOsmol/kg, ~270-~325 mOsmol/kg, or, e.g., ~270-~320 mOsmol/kg, such as, for example ~265-~340 mOsmol/kg, ~260-~340 mOsmol/kg, ~255-~340 mOsmol/kg, or, e.g., ~250-~340 mOsmol/kg, such as, for example, about ~280-~330 mOsmol/kg, ~270-~320 mOsmol/kg, or, e.g., ~280-~310 mOsmol/kg.

In aspects, the described osmolality of compositions provided by the invention is the osmolality of the compositions upon completion of manufacturing, packaging of the composition(s), storage of the composition(s), and at the time of administration. In aspects, compositions are provided in ready-to-use (RTU) form and have such an osmolality without the need to dilute the composition, add a tonicity agent to adjust tonicity prior to administration, or both.

In aspects, composition(s) have an osmolality described here which is attained by the addition of one or more tonicity agents as constituent(s) of a tonicity component during manufacturing. In aspects, compositions do not comprise a tonicity component and hence do not comprise any ingredient characterizable as a tonicity agent, such that the agent is capable of, and present in a suitable and sufficient amount to, detectably or significantly modify or affect the tonicity (osmolality) of the composition(s).

Aqueous

In aspects, compositions provided by the invention comprise water (e.g., water for injection) as a carrier and hence are characterizable as aqueous composition(s). In aspects, water is a solvent or the solvent for the composition. In aspects, compositions provided by the invention are aqueous solutions. In aspects, most of any carrier component, e.g., generally all, essentially all, substantially all, or all of a carrier component is water. In aspects, compositions provided by the invention are stable, ready-to-use, aqueous solutions comprising an ASCC component, a chelation component, optionally a tonicity component, and one or more additional excipients, wherein the composition can be stored at controlled room temperature for a period of at least ~1 month, ~2 months, ~3 months, ~6 months, ~9 months, or, e.g., at least about 12 months at controlled room temperature.

Storage & Stability

In aspects, compositions herein are characterizable as stable at controlled room temperature for at least about 1 months, such as, for example, ≥~2 months, ≥~3 months, ≥~4 months, ≥~5 months, ≥~6 months, ≥~7 months, ≥~8 months, ≥~9 months, ≥~10 months, ≥~11 months, ≥~12 months, ≥~16 months, ≥~20 months, ≥~24 months, ≥~28 months, ≥~32 months, or, e.g., ≥~36 months. Herein, a "stable composition" refers to preparation(s) of ASCCs having sufficient physical stability, chemical stability, or both, to allow storage at a convenient temperature, such as between about 0° C. and about 50° C., e.g., ~0° C.-~45° C., ~0°

C.-~40° C., ~0° C.-~35° C., ~0° C.-~30° C., ~0° C.-~25° C., or, e.g., ~5° C.-~50° C., ~10° C.-~50° C., ~15° C.-~50° C., ~20° C.-~50° C., or, e.g., ~25° C.-~50° C., such as, for example, ~5° C.-~45° C., ~10° C.-~40° C., ~15° C.-~35° C., ~20° C.-~30° C., or, e.g., about 25° C., for a commercially reasonable period of time.

The term "physical stability" herein refers to maintenance of color, maintenance of dissolved oxygen level, maintenance of head space oxygen level, maintenance of acceptable levels of particulate matter, or any combination thereof.

The term "chemical stability" herein refers to the lack of formation of any unacceptable levels) of drug-related impurities, e.g., in terms of total impurity(ies), single maximum individual impurity, maximum individual unknown impurity(ies), or any combination thereof. For the purpose of the present invention, "chemical stability" also includes maintenance of a pH of the finished formulation of between about 5 and 8. Herein, a commercially relevant period of time is a period of time after manufacturing extending to about, e.g., at least about 3 months, such as, e.g., ≥~6 months, ≥~9 months, ≥~12 months, ≥~18 months, ≥~24 months, or, e.g., ≥~36 months, during which period of time the finished product (the finished composition in ready-to-use form, e.g., a form ready for parenteral administration without a requirement for additional modification such as, e.g., by dilution or tonicity adjustment) is maintained in its original packaging under specified storage conditions.

Herein, "controlled room temperature" means a temperature of between about 20° C. and about 30° C., such as, e.g., 20° C. to about 25° C., such as, for example, about 25° C.±2° C., or, e.g., temperatures which would be considered in the art as room temperature, such as not requiring refrigeration or freezing storage temperatures. In aspects, compositions provided by the invention do not require storage under refrigerated conditions. In aspects, compositions provided by the invention do not require freezer storage.

In aspects, composition(s) provided by the invention remain stable when stored at room temperature conditions, e.g., about 25° C.±2° C. and about 60%±5% relative humidity, accelerated conditions, e.g., about 40° C.±2° C. and about 75% RH±5% relative humidity, or both, for a period of at least about 3 months. Specific measures of stability, such as, e.g., stability according to the United States FDA stability standards, are described here.

In aspects, the invention provides ready-to-use (RTU) pharmaceutical composition(s) comprising (a) an ASCC component, and (b) one or more pharmaceutically acceptable excipients which can, optionally, include a tonicity agent component, wherein the composition can be stored at 20° C. to 25° C.±2° C. for at least one month, e.g., ≥~2 months, ≥~3 months, ≥~6 months, ≥~9 months, ≥~12 months, ≥~18 months, ≥~24 months, or, e.g., ≥~36 months prior to use, and wherein over such period of time the pharmaceutical composition(s) are stable according to one or more United States Food and Drug Administration stability standards In aspects, the invention provides ready-to-use (RTU) pharmaceutical composition(s) comprising (a) an ASCC component, and (b) one or more pharmaceutically acceptable excipients which can, optionally, include a tonicity agent component, wherein the composition(s) exhibit greater than 95%, such as, e.g., ≥~96%, ≥~97%, ≥~98%, or even ≥~99%, undegraded ASCC(s) compared to initial concentration when stored for at least 3 months, such as, e.g., ≥~6 months, ≥~9 months, or ≥~12 months, at 25° C.±2° C. and 60%±5% relative humidity, 40° C.±2° C. and 75%±5% relative humidity, or both. Alternatively stated, ASCC(s) demonstrate less than about 5% degradation, e.g., ≤~4%, ≤~3%, ≤~2%, or, e.g., ≤~1% degradation from an initial starting amount when stored for at least 3 months, such as, e.g., ≥~6 months, ≥~9 months, or ≥~12 months, at 25° C.±2° C. and 60%=5% relative humidity, 40° C.±2° C. and 75%±5% relative humidity, or both.

In aspects, RTU composition(s) described herein retain at least about 90%, such as, e.g., ≥~91%, ≥~92%, ≥~93%, ≥~94%, ≥~95%, ≥~96%, ≥~97%, ≥~98%, or, e.g., ≥~99%, of the labelled concentration of ASCC(s) after storage under typical (e.g., about room temperature, e.g., controlled room temperature) and/or accelerated conditions.

In aspects, RTU compositions of ASCC(s) provided by the invention are capable of maintaining at least about 90%, ≥~92%, ≥~94%, ≥~96%, ≥~98%, or, e.g., ≥~99%, of the ASCC component in undegraded form after storage for at least about 3 months, ~6 months, or at least about 12 months or longer at room temperature, and, further, wherein the amount of ASCC component present after about 1, ~3, ~6, ~8, ~10, ~12, ~14, ~16, ~18, ~20, ~22, ~24, ~26, ~28, ~30, ~32, ~34, or about 36 months of storage at 20° C. to 25° C.±2° C. is at least about 90% of the amount of ASCC component, e.g., ≥~92%, ≥~94%, ≥~96%, ≥~98%, or, e.g., ≥~99%, of the amount of ASCC component, present in the composition(s) at the time of packaging.

In aspects, RTU compositions of ASCC(s) provided by the invention contain less than about 2.5%, such as, e.g., ≤~2%, ≤~1.5%, ≤~1%, or, e.g., ≤~0.5%, total impurities when stored at 25° C.±2° C. and 60%±5% relative humidity, 40° C.±2° C. and 75%±5% relative humidity, or both, for a period of at least about 1 month, at least about 2 months, or e.g., ≥~3, ≥~6 months, ≥~9 months, ≥~12 months, ≥~18 months, or, e.g., ≥~24 months prior to use.

In aspects, RTU compositions of ASCC(s) provided by the invention pass the Particulate Matter test under USP<788> when stored at 20° C. to 25° C.±2° C. for at least about 3 months, such as, e.g., ≥~6 months, ≥~9 months, ≥~12 months, ≥~18 months, or, e.g., ≥~24 months prior to use. Herein, reference to "USP<[#]>" refers to the chapter number of the United States Pharmacopeia (USP) at the time of this disclosure, describing the referenced standard (e.g., assay/test) or a recognized international equivalent standard. Substantially equivalent standards or other equivalents thereof also may be suitably used in aspects.

In aspects, RTU compositions of ASCC(s) provided by the invention pass the pH test under USP<791> with variation in pH of ±0.5 pH unit or less compared to original pH when stored at 20° C. to 25° C.±2° C. for at least about 1 month, at least about 2 months, or, e.g., ≥~3, ≥~6 months, ≥~9 months, ≥~12 months, ≥~18 months, or, e.g., ≥~24 months prior to use.

In aspects, RTU compositions of ASCC(s) provided by the invention pass the Completeness of Solution Test under USP<641>, exhibiting a clear solution, when stored at 20° C. to 25° C.±2° C. for at least about 3 months, such as, e.g., ≥~6 months, ≥~9 months, ≥~12 months, ≥~18 months, or, e.g., ≥~24 months prior to use.

In aspects, RTU compositions of ASCC(s) provided by the invention pass the Visible Particles test under USP<790>, exhibiting absence of visible particles, when stored at 20° C. to 25° C.±2° C. for at least about 3 months, such as, e.g., ≥~6 months, ≥~9 months, ≥~12 months, ≥~18 months, or, e.g., ≥~24 months prior to use.

In aspects, RTU compositions of ASCC(s) provided by the invention exhibit ASCC(s) as measured by HPLC of 95-105% of initial value under USP<621> when stored at 20° C. to 25° C.±2° C. for at least about 3 months, such as, e.g., ≥~6 months, ≥~9 months, ≥~12 months, ≥~18 months, or, e.g., ≥~24 months prior to use.

In aspects, RTU compositions of ASCC(s) provided by the invention exhibit not more than 0.1% ascorbic acid related impurity as measured by HPLC under USP<621>, such as, e.g., <0.09%, <0.08%, <0.06%, <0.04%, or, e.g., <0.02%, when stored at 20° C. to 25° C.±2° C. for at least about 3 months, such as, e.g., ≥~6 months, ≥~9 months, ≥~12 months, ≥~18 months, or, e.g., ≥~24 months prior to use.

In aspects, RTU compositions of ASCC(s) provided by the invention exhibit not more than 0.1% of any single unidentified impurity as measured by HPLC under USP<621>, such as, e.g., <0.09%, <0.08%, <0.06%, <0.04%, or, e.g., <0.02%, when stored at 20° C. to 25° C.±2° C. for at least about 3 months, such as, e.g., ≥~6 months, ≥~9 months, ≥~12 months, ≥~18 months, or, e.g., ≥~24 months prior to use.

In aspects, RTU compositions of ASCC(s) provided by the invention exhibit not more than 0.4% total impurities as measured by HPLC under USP<621>, such as, e.g., <0.3%, <0.2%, <0.1%, <0.08%, <0.06%, <0.04%, or, e.g., <0.02%, when stored at 20° C. to 25° C.±2° C. for at least about 3 months, such as, e.g., ≥~6 months, ≥~9 months, ≥~12 months, ≥~18 months, or, e.g., ≥~24 months prior to use.

In aspects, RTU compositions of ASCC(s) provided by the invention exhibit a Total Aerobic Microbial Count (TAMC) of no greater than 10 cfu/100 mL by USP <621>, such as, e.g., ≤9 cfu/100 mL, ≤8 cfu/100 mL, ≤7 cfu/100 mL, ≤6 cfu/100 mL, ≤5 cfu/100 mL, ≤4 cfu/100 mL, ≤3 cfu/100 mL, ≤2 cfu/100 mL, or, e.g., ≤1 cfu/100 mL, when stored at 20° C. to 25° C.±2° C. for at least about 3 months, such as, e.g., ≥~6 months, ≥~9 months, ≥~12 months, ≥~18 months, or, e.g., ≥~24 months prior to use.

In aspects, RTU compositions of ASCC(s) provided by the invention exhibit a Total Yeast and Molds Count (TYMC) of no greater than 10 cfu/100 mL by USP <621>, such as, e.g., such as, e.g., ≤9 cfu/100 mL, ≤8 cfu/100 mL, ≤7 cfu/100 mL, ≤6 cfu/100 mL, ≤5 cfu/100 mL, ≤4 cfu/100 mL, ≤3 cfu/100 mL, ≤2 cfu/100 mL, or, e.g., ≤1 cfu/100 mL, when stored at 20° C. to 25° C.±2° C. for at least about 3 months, such as, e.g., ≥~6 months, ≥~9 months, ≥~12 months, ≥~18 months, or, e.g., ≥~24 months prior to use.

In aspects, RTU compositions of ASCC(s) provided by the invention exhibit no greater than 35 IU/mL Endotoxins by USP<85>, such as, e.g., ≤30 IU/mL, ≤25 IU/mL, ≤20 IU/mL, ≤15 IU/mL, ≤10 IU/mL, or, e.g., ≤5 IU/mL Endotoxins at the time of manufacture and when stored at 20° C. to 25° C.±2° C. for at least about 3 months, such as, e.g., ≥~6 months, ≥~9 months, ≥~12 months, ≥~18 months, or, e.g., ≥~24 months prior to use.

In aspects, RTU compositions of ASCC(s) provided by the invention are characterizable as, e.g., identifiable as, sterile by USP <71>, at the time of manufacture and when stored at 20° C. to 25° C.±2° C. for at least about 3 months, such as, e.g., ≥~6 months, ≥~9 months≥~12 months, ≥~18 months, or, e.g., ≥~24 months prior to use.

In aspects, RTU compositions of ASCC(s) provided by the invention that are pH 5-8 by USP <791>, at the time of manufacture and after storage at 20° C. to 25° C.±2° C. for at least about 3 months, such as, e.g., ≥~6 months, ≥~9 months, ≥~12 months, ≥~18 months, or, e.g., ≥~24 months prior to use.

In aspects, RTU compositions of ASCC(s) provided by the invention are capable of being stored in airtight packaging at 20° C. to 25° C.±2° C. for about 1 month, such as, e.g., ~3 months, ~6 months, ~9 months, ~12 months, ~18 months, ~24 month, ~36 months, or, e.g., longer, without experiencing an increase in pressure within the airtight packaging which would demonstrate product instability according to any industry recognized standard of stability, such as, e.g., a United States Food and Drug-recognized measure of stability.

Administered Form & Administration Rates

In aspects, RTU compositions provided by the invention are administered by any suitable method of administration, such as, e.g., by parenteral routes of administration, such as, e.g., subcutaneous, intramuscular, intravenous, intra-atrial, or intra-arterial continuous infusion to a patient.

In specific aspects, compositions provided by the invention are administered intravenously, e.g., by intravenous injection or intravenous infusion.

In aspects, pharmaceutical compositions provided by the invention are ready-to-use (RTU) pharmaceutical compositions of ASCC(s) intended for intravenous administration. In aspects, intravenous administration is selected from one or more of intravenous injection and intravenous infusion. Compositions administered without dilution by intravenous injection can be administered, e.g., once, twice, three times, four times, or more times, per day. In aspects, compositions administered by intravenous infusion can be administered without dilution at an infusion rate of about 1 mg/min to about 50 mg/min, such as, e.g., ~1 mg/min-~45 mg/min, ~1 mg/min-~40 mg/min, ~1 mg/min-~35 mg/min, ~1 mg/min-~30 mg/min, ~1 mg/min-~25 mg/min, ~1 mg/min-~20 mg/min, ~1 mg/min-~15 mg/min, ~1 mg/min-~10 mg/min, or, e.g., ~1 mg/min-~5 mg/min, such as, e.g., ~5 mg/min-~50 mg/min, ~10 mg/min-~50 mg/min, ~15 mg/min-~50 mg/min, ~20 mg/min-~50 mg/min, ~25 mg/min-~50 mg/min, ~30 mg/min-~50 mg/min, ~35 mg/min-~50 mg/min, ~40 mg/min-~50 mg/min, or, e.g., ~45 mg/min-~50 mg/min, such as, e.g., about 1.3 mg/min, 3.3 mg/min, or, e.g., 33 mg/min or more.

According to one specific aspect, the invention provides an injectable, ready-to-use (RTU) pharmaceutical composition comprising (a) a unit dose amount of an ascorbic acid compound component (ASCC component). In aspects, the RTU pharmaceutical composition further comprises one or more excipients that are pharmaceutically suitable for an injectable ascorbic acid compound composition. In aspects, the RTU pharmaceutical composition has an osmolality of about 270 mOsm/kg to about 340 mOsm/kg. In aspects, the RTU pharmaceutical composition does not require dilution prior to administration to a patient. In aspects, the RTU pharmaceutical composition is stable according to United States Food and Drug Administration stability standards when stored at 20° C. to 25° C.±2° C. for at least 3 months prior to use. In aspects, the RTU pharmaceutical composition has been demonstrated to be effective in treating scurvy in a statistically significant population of scurvy patients when administered in an effective daily dose for a sufficient period. In aspects, the RTU pharmaceutical composition is bioequivalent to a second pharmaceutical composition, wherein the second pharmaceutical composition when administered to a population of scurvy patients results in a statistically significant number of the scurvy patients being effectively treated in one or more well controlled and adequate studies. In aspects, the second pharmaceutical composition is the product approved under the United States Food and Drug Administration NDA number 209112 (ASCOR®). In aspects, both (a) the RTU pharmaceutical composition has been demonstrated to be effective in treating scurvy in a statistically significant population of scurvy patients when administered in an effective daily dose for a sufficient period, and (b) the RTU pharmaceutical composition is bioequivalent to a second pharmaceutical composition, wherein the second pharmaceutical composition when administered to a population of scurvy patients results in a statistically significant number of the scurvy patients being effectively treated in one or more well controlled and adequate studies, are true.

Methods of Use

In aspects, compositions provided by the invention are ready-to-use compositions suitable for treating or preventing diseases, conditions, symptoms, or combination(s) thereof related to or caused by ascorbic acid (vitamin C) deficiency or for otherwise modulating the physiological state of a patient or for preventing or treating any disease or condition that is preventable or treatable by delivery of an effective amount of a composition/formulation of the invention. In aspects, the phrase, "a vitamin C deficiency" or "ascorbic acid deficiency" means disease(s), condition(s), symptom(s), or any combination thereof related to a deficiency of ascorbic acid (vitamin C). In aspects, "to treat" or "treatment of" means to detectably or significantly ameliorate, or detectable or significant amelioration of, e.g., a disease, condition, symptom, or combination thereof, or, e.g., detectably or significantly improving or modulating, or detectable or significant improvement or modulation of, e.g., a disease, condition, symptom, or combination thereof. In aspects, "disease" and "condition" are interchangeable, such that, e.g., a condition in aspects generally indicates a state of health, and, e.g., a condition wherein the state of health is characterizable as ill or poor, or has otherwise been diagnosed as a disease or a disorder, a "condition" can be also be referred to as a "disease"/"disorder". For example, disclosure related to the treatment disease(s), condition(s), or symptom(s) with a composition provided by the invention can be interpreted as the detectable or significant amelioration, modulation, or improvement of such disease(s), condition(s), or symptom(s), given the provision of a sufficient quantity of a composition provided by the invention. In aspects, "to prevent" or "prevention of" means to detectably or significantly reduce the severity of onset, delay the onset, delay an increase in severity, or to avoid the onset of, e.g., a disease, condition, symptom, or combination thereof, given the provision of a sufficient quantity of a composition provided by the invention.

In certain aspects, compositions provided by the invention allow treatment of one or more such conditions with ready-to-use compositions such that administering personnel (those administering composition(s) to a recipient) do not need to perform any additional preparation of the composition(s) prior to administration, such as, e.g., compositions do not require additional dilution, tonicity modification, or both prior to administration. Accordingly, in aspects, significant benefits of such compositions include a reduction in the time required for treating an individual in need thereof.

In aspects, RTU pharmaceutical compositions of ASCC(s) provided by the invention detectably or significantly reduce the risk of contamination of composition(s) prior to administration when treating a significant number of patients in a population of patients in need thereof, compared to the risk of contamination of a pharmacy bulk packaging preparation of an ascorbic acid composition administered via a pharmacy admixture program to a similar population of patients.

In aspects, RTU pharmaceutical compositions of ASCC(s) provided by the invention detectably or significantly reduce the number of dosing errors (a dosing error being an error related to the dose of an ASCC due to human mistakes incurred during preparation of the composition(s), prior to administration of composition(s), leading to a recipient receiving an unintended dose of ASCC), when treating a significant number of patients in a population of patients in need thereof, compared to the number of dosing errors when treating a similar population of patients with a pharmacy bulk packaging preparation of an ascorbic acid composition administered via a pharmacy admixture program.

According to aspects, compositions provided by the invention are administered parenterally, such as, e.g., by intravenous injection or intravenous infusion, at least once per day for up to at least about 7 days, such as, e.g., at least twice per day, at least three times per day, or, e.g., at least four times per day, for up to about 7 days, such as, e.g., for up to about 1 day, about 2 days, about 3 days, about, 4 days, about 5 days, about 6 days, or, e.g., about 7 days.

In aspects, compositions provided by the invention are administered to a human recipient of at least about 5 months of age, e.g., compositions herein can be administered to a human recipient of about 4 months, of age, 5 months of age, 6 months of age, 8 months of age, 10 months of age, 1 year of age, or older, such as to children (e.g., 3 years of age or older), teens (e.g., 13 years of age or older), adults (e.g., 18 years of age or older), and the elderly (e.g., 65 years of age or older).

In aspects, compositions provided by the invention provide ASCC(s) to a recipient, such as, e.g., a human recipient, for whom oral ASCC administration has been previously demonstrated as unsuccessful, insufficient, or both, or, e.g., for whom oral ASCC administration is not possible (such as, e.g., an inability to swallow or other condition prohibiting oral intake of such ASCC(s)) or is contraindicated.

Exemplary Target/Treatable Conditions

Scurvy

In aspects, compositions provided by the invention can be administered in sufficient amounts to treat scurvy (e.g., in an amount that is demonstrated to be effective in the treatment of one or more aspects of scurvy in a significant number of patients, through clinical trials, bioequivalence, or otherwise). In aspects, the invention provides a method of treating scurvy in an individual diagnosed with scurvy. In aspects, the invention provides a method of treating scurvy comprising administering an effective amount of a pharmaceutical composition described herein, such as, e.g., a composition comprising an ASCC component and one or more excipients, for a period of 1 week or less, such as, e.g., about 6 days or less, ≤~5 days, ≤~4 days, ≤~3 days, ≤~2 days, or, e.g., ~1 day.

In aspects, the invention provides a method of treating scurvy in adult and pediatric patients aged 5 months and older for whom oral administration is not possible, insufficient, or contraindicated, with the RTU pharmaceutical compositions of ASCC(s) described herein, for a period of up to 1 week (7 days).

In aspects, the invention provides a method of treating scurvy with an RTU pharmaceutical composition of ASCC (s), wherein the composition is stable when stored between 20° C. to 25° C.±2° C. for at least about one month, such as, e.g., ≥~3 months, ≥~6 months, ≥~9 months, ≥~12 months, ≥~18 months, or, e.g., ≥~24 months prior to use. In aspects, such compositions comprise one or more additional excipients. In aspects, such excipients comprise a chelation component. In aspects, such a chelation component comprises a single chelation agent. In aspects, such excipients comprise a tonicity component. In aspects, such excipients do not comprise a tonicity component.

In aspects, composition(s) provided by the invention are effective in treating scurvy in a statistically significant population of scurvy patients when administered in an effective daily dose for a sufficient period. In aspects, the invention provides a method of treating scurvy in a human recipient, the method comprising use of the pharmaceutical composition(s) described herein, wherein the RTU pharmaceutical composition(s) have been demonstrated to be effective in treating scurvy in a statistically significant population of scurvy patients when administered in an effective daily dose for a sufficient period.

In aspects, composition(s) provided by the invention are bioequivalent to a second pharmaceutical composition. In aspects, administration of the second pharmaceutical composition to a population of scurvy patients results in a statistically significant number of the scurvy patients being effectively treated. In aspects, the invention provides a method of treating scurvy wherein in a human recipient, the method comprising use of the pharmaceutical composition(s) described herein, wherein the RTU pharmaceutical composition(s) is bioequivalent to a second pharmaceutical composition, wherein the second pharmaceutical composition, when administered to a population of scurvy patients results, results in a statistically significant number of the scurvy patients being effectively treated in one or more well controlled and adequate studies.

In aspects, the invention provides a method of treating scurvy in a population of patients diagnosed with scurvy, wherein (a) the population of patients comprises at least 2 patients requiring a different total amount of ascorbic acid compound per dose; (b) the method comprises administering to each patient of the population of patients an individually packaged, ready-to-use, single dose of a composition comprising an ascorbic acid compound, stable when stored at about 20° C. to 25° C.±2° C. for a period of at least 1 month, and (c) the method results in an amount of waste of the ascorbic acid compound which is detectably or significantly less than the amount of an ascorbic acid compound left unused with respect to treatment of scurvy in a similar population of patients with the product approved under the United States Food and Drug Administration NDA number 209112 (ASCOR®).

A method of treating scurvy in a patient diagnosed with scurvy with a ready-to-use composition comprising an ascorbic acid compound, wherein the composition (a) is stable when stored at 20° C. to 25° C.±2° C. for at least one month prior to use, and (b) is provided in a single dose container entered a single time by a collection device when administered to a patient.

In aspects, the invention provides a method of treating scurvy in a population of patients diagnosed with scurvy, wherein the method comprises administration of at least one individually packaged, ready-to-use single dose of a composition comprising an ascorbic acid compound, wherein the risk of administering to any single patient within the population of patients a total amount of the ascorbic acid compound other than the intended total amount of the ascorbic acid compound is detectably or significantly less than the risk of administering any single patient within a similar population of patients treated with the product approved under the United States Food and Drug Administration NDA number 209112 (ASCOR®) a total amount of ascorbic acid compound other than the intended total amount of ascorbic acid compound.

In aspects, the invention provides a method of treating scurvy in a population of patients diagnosed with scurvy, wherein the method comprises administration of at least one individually packaged, ready-to-use, single dose of a composition comprising an ascorbic acid compound, wherein the method results in a risk of contaminating the composition prior to administration of the composition to any single patient within the population of patients which is detectably or significantly less than the risk of contaminating a second composition approved under the United States Food and Drug Administration NDA number 209112 (ASCOR®) prior to the administration of ASCOR® for treating scurvy in a similar population of patients.

In aspects, the invention provides a method of treating scurvy in an individual recipient, the method comprising administering an individually packaged dose of a composition provided in ready-to-use form, the composition comprising an ASCC component present in the composition in a concentration of no more than about 50 mg/mL, such as, e.g., ≤~45 mg/mL, ≤~40 mg/ml, ≤~35 mg/ml, ≤~30 mg/ml, ≤~25 mg/mL, or, e.g., ≤~20 mg/ml.

In aspects, the invention provides a method of treating scurvy in an individual diagnosed with scurvy, the method comprising administering an individually packaged, single dose of a composition comprising ASCC(s) provided in ready-to-use form. In aspects, the individually packaged dose of a composition provided in RTU form comprises an ASCC component present in the composition in a total amount of no more than about 500 mg, such as, e.g. no more than ~475 mg, ~450 mg, ~425 mg, ~400 mg, ~375 mg, ~350 mg, ~325 mg, ~300 mg, ~275 mg, ~250 mg, ~225 mg, or, e.g., ~200 mg, such as, e.g., no more than about 175 mg, ~150 mg, ~125 mg, ~100 mg, ~75 mg, or, e.g., ~50 mg, ~40 mg, ~30 mg, or, e.g., ~20 mg of an ASCC component.

Wound Healing

In aspects, the invention provides a method of detectably or significantly decreasing the healing time (e.g., increasing the speed at which a wound exhibits detectable or significant healing) of a wound in a mammal suffering therefrom, the method comprising administration of a composition comprising an ASCC component, such compositions being any one or more compositions described herein.

In aspects, the invention provides a method of detectably or significantly decreasing the healing time (e.g., increasing the speed at which a wound exhibits detectable or significant healing) of a wound in a mammal suffering therefrom, the method comprising administering an individually packaged dose of a composition described herein, provided in ready-to-use form.

In aspects, the invention provides a method of detectably or significantly decreasing the healing time (e.g., increasing the speed at which a wound exhibits detectable or significant healing) of a wound in a mammal suffering therefrom, the method comprising administration of a ready-to-use composition comprising (a) an ASCC component, and (b) at least one or more additional excipients, wherein the one or more additional excipients may in aspects comprise a chelation component, a tonicity component, or both, wherein the composition is stable when stored at 20° C. to 25° C.±2° C. for at least about one month, such as, e.g., ≥~3 months, ≥~6 months, ≥~9 months≥~12 months, ≥~18 months, or, e.g., ≥~24 months prior to use.

In aspects, the invention provides a method of detectably or significantly decreasing the healing time (e.g., increasing the speed at which a wound exhibits detectable or significant healing) of a wound in a mammal suffering therefrom, the method comprising administration of a ready-to-use composition comprising (a) an ascorbic acid compound which is (I) present in an amount of less than about 400 mg, such as less than ~400 mg, (II) present in a concentration of no more than 50 mg/mL, or (III) both (I) and (II), (b) one or more additional excipients, and (c) optionally a tonicity component, and wherein the composition is stable when stored between 20° C. to 25° C.±2° C. for at least about one month, such as, e.g., ≥~3 months, ≥~6 months, ≥~9 months, ≥~12 months, ≥~18 months, or, e.g., ≥~24 months prior to use.

In aspects, the invention provides a method of detectably or significantly decreasing the healing time (e.g., increasing the speed at which a wound exhibits detectable or significant healing) of a wound in a mammal suffering therefrom, the method comprising injecting a sufficient amount of a composition so as to deliver about 1 g of an ASCC component, about once per day, for a period of about, e.g., 3 days to about 25 days, such as, e.g., ~5 days-~25 days, ~10 days-~25 days, ~15 days-~25 days, or, e.g., ~20 days-~25 days, such as, for example, ~3 days-~20 days, ~3 days-~15 days, ~10 days-~10 days, or, e.g., ~3 days-~5 days, such as, e.g., for a period of about 5 to about 21 days.

Other Vitamin C-Related Conditions/Applications

According to aspects, the invention provides a method of modulating the physical state of a subject (recipient), the physical state being a physical state being a physical state which can be detectably or significantly modified by the provision of a sufficient amount of ascorbic acid, the method comprising administration of a composition described herein comprising an ASCC component. In aspects, the invention provides a method of detectably or significantly increasing the level of ascorbic acid (vitamin C), the method comprising administration of a composition described herein comprising an ASCC component. In aspects, the method comprises detectably or significantly increasing the level of ascorbic acid (vitamin C) in a recipient suffering from or diagnosed with a disease or condition related to vitamin C deficiency or suffering from a symptom related to vitamin C deficiency.

In aspects, the invention provides a method of treating vitamin C deficiency in an individual diagnosed with vitamin C deficiency, the method comprising administration of a RTU composition described herein comprising an ASCC component. In aspects, the method comprises administering an individually packaged dose of such a composition provided in ready-to-use form.

In aspects, the invention provides a method of treating a vitamin C deficiency in a patient, the method comprising administration of a RTU composition comprising (a) an ASCC component, and (b) excipient(s), such one or more excipients comprising, e.g., a chelation component and, optionally, a tonicity component, and wherein the composition is stable when stored between 20° C. to 25° C.±2° C. for at least one month, such as, e.g., ≥~3 months, ≥~6 months, ≥~9 months, ≥~12 months, ≥~18 months, or, e.g., ≥~24 months prior to use.

In aspects, the invention provides a method of treating a vitamin C deficiency in a recipient, the method comprising administration of a RTU composition comprising (a) an ASCC component which is (I) present in an amount of less than about 400 mg, such as, e.g., less than about 350 mg, (II) present in a concentration of no more than 50 mg/mL, or (III) both (I) and (II), (b) excipient(s), wherein the one or more additional excipients is a chelating component and, optionally, a tonicity component, and, wherein the composition is stable when stored between 20° C. to 25° C.±2° C. for at least one month, such as, e.g., ≥~3 months, ≥~6 months, ≥~9 months, ≥~12 months, ≥~18 months, or, e.g., ≥~24 months prior to use.

In aspects, the invention provides a method of treating a vitamin C deficiency in a recipient, the method comprising administration of a RTU composition described herein in a sufficient amount so as to provide about 200 mg of the ASCC component per dose, wherein such an administration is provided about once per day for a period of about 1 day, about 2 days, about 3 days, about 4 days, about 5 days, about 6 days, or, e.g., about 7 days (e.g., about 1 week).

In one exemplary aspect, the invention provides a method of treating a disease, condition, or symptom related to vitamin C deficiency, the method comprising (a) providing an injectable pharmaceutically acceptable composition in a container component (in a container), the composition comprising an effective unit dose amount of an ascorbic acid compound component (such as, e.g., a component comprising or essentially consisting of sodium ascorbate) and one or more excipients, the composition being stored in the container component in ready-to-use form, wherein the composition has an osmolality of about 270 mOsm/kg to about 340 mOsm/kg and is stable when stored at 20° C. to 25° C.±2° C. for at least 3 months (e.g., ≥~1, ≥~2, ≥~3, ≥~6, ≥~9,≥~12, or, e.g., ≥~18 months, prior to use, (b) directly administering an effective amount of the formulation to a subject having a vitamin C deficiency by parenteral administration, such as, e.g., by injection or slow intravenous infusion, and (c) as needed to effectively treat a vitamin C deficiency, repeating steps (a) and (b) for a number of times until effective treatment of the disease or condition related to vitamin C deficiency in the subject is achieved. In aspects, steps (a) and (b) are repeated at least once per day, such as, e.g., 1 time per day, 2 times per day, or 3 times per day or more, for a period of about 2 days to about 14 days, such as, e.g., ~2 days-~12 days, ~2 days-~10 days, ~2 days-~8 days, or, e.g., ~2 days-~7 days.

In another specific aspect, the invention provides a method of preventing a disease, condition, or symptom related to vitamin C deficiency, the method comprising (a) providing an injectable pharmaceutically acceptable composition in a container component (in a container), the composition comprising an effective unit dose amount of an ascorbic acid compound component (such as, e.g., a component comprising or essentially consisting of sodium ascorbate) and one or more excipients, the composition being stored in the container component in ready-to-use form, wherein the composition has an osmolality of about 270 mOsm/kg to about 340 mOsm/kg and is stable when stored at 20° C. to 25° C.±2° C. for at least 3 months (e.g., ≥~1, ≥~2, ≥~3,≥~6,≥~9,≥~12, or, e.g., ≥~18 months, prior to use, (b) directly administering an effective amount of the composition to a subject having or at risk of developing a vitamin C deficiency by parenteral administration, such as, e.g., by injection or slow intravenous infusion, and (c) as needed to effectively prevent a vitamin C deficiency, repeating steps (a) and (b) for a number of times such that prevention of a vitamin C deficiency in the subject is achieved.

In aspects, the invention provides method(s) of treating disease(s), condition(s), or symptom(s) related to vitamin C with composition(s) described herein, such diseases, conditions, or symptoms including but not being limited to, e.g., those previously described (e.g., scurvy, wound healing, etc.) and, e.g., physical weakness or fatigue (such as, e.g., during pregnancy), poor or negative mood, weight gain joint pain, joint swelling, capillary bleeding (e.g., bleeding gums), nasal bleeding, hematuria, anemia, dry skin, skin pigmentation (e.g., freckles), bruising, inflammation, oxidative stress, and, e.g., absorption-related diseases (e.g., sunlight sensitivity and skin diseases). In aspects, compositions provided by the invention are used to, or, e.g., are used in methods resulting in, skin whitening, promote/promotion of the formation of gamma globulin, strengthen/strengthening the immune system, participate/participation in the biological oxidation process in vivo, participate/participation in erythropoiesis, adrenocortical hormone synthesis, and, e.g., neurotransmitter synthesis, participate/participation in detoxification process(es), etc. In aspects, the invention provides methods of promoting healthy aging, treating or detectably or significantly reducing the risk of age-related diseases or conditions, such as, e.g., tumor development, cancer, heart disease, arthritis, etc., or, e.g., or, e.g., detectably or significantly reducing free radical development, accumulation, or both (e.g., by reducing oxidation/providing anti-oxidant effect), detectably or significantly promoting heavy metal ion excretion, reducing or preventing the generation of nitrosamine, improving myocardial metabolism, strengthening tissue contractility, promoting collagen fiber formation, promoting the formation of cementing substances, etc. In aspects, the invention provides methods of detectably or significantly increasing collagen production or treating one or more conditions related to collagen production, such as, e.g., rough or bumpy skin (keratosis pilaris), the method comprising administering a composition described herein. In aspects, the invention provides a method of detectably or significantly modulating the protein structure of hair as it grows, such as, e.g., hair growing in bent or coiled shapes (e.g., "corkscrew hair"), the method comprising administering a composition described herein. In aspects, the invention provides methods of detectably or significantly decreasing perifollicular hemorrhaging (the breaking of blood vessels supplying blood to hair follicles), the method comprising a composition described herein. In aspects, the invention provides methods of detectably or significantly reducing one or more characteristics of or conditions related to nail(s) or nail bed(s), such as, e.g., splinter hemorrhaging (red spots or vertical lines in the nail bed) or spoon-shaped (concave) nail beds, the method comprising administration of a composition described herein.

In aspects, such methods can, in aspects, comprise administering composition(s) described herein in sufficient doses/amounts and at sufficient frequency to detectably or significantly treat such diseases, conditions, or to attain such targeted effect. In aspects, such dosing and frequency of administration can be a dosing and frequency described above; in aspects, such a dose can be much higher, such as, e.g., in the case of skin whitening, wherein a dose administered by IV can be, e.g., from about 2,500 grams to about 5,000 grams or higher.

Optionally Excluded Elements—Methods

In aspects, the invention provides methods of using compositions described herein, wherein the method(s) is/are characterizable by the lack/absence of certain steps, elements, or characteristics. For example, in aspects, methods provided by the invention do not comprise dilution of composition(s) prior to use. That is, in aspects, methods provided by the invention to not comprise a step for modifying the concentration of the composition(s) or composition components prior to administration.

In further aspects, methods provided by the invention do not comprise treating more than one patient with each provided package of composition. In aspects, methods provided by the invention do not comprise entering the packaged composition (e.g., by needle for withdrawal of the ready-to-use composition) more than once.

In other aspects, methods provided by the invention do not comprise modification of the tonicity, e.g., the osmolality, of the composition prior to administration of the composition(s). In aspects, method comprise administration of only ascorbic acid compound(s) in the treatment of an indicated condition, such as scurvy.

In certain aspects, compositions herein do not require refrigeration, e.g., compositions do not require storage at 2° C.-8° C. (36° F.-46° F.) prior to use.

Methods of Manufacturing

In one aspect, composition(s) can be prepared by using any suitable technique, many of which are known to those skilled in the art.

In aspects, steps of a manufacturing process employed for preparing compositions of the invention can be combined in any suitable order resulting in a sterile product, and capable of meeting stability standard(s) as described herein.

In aspects, the invention provides a process (method) for preparing (manufacturing) a stable, ready-to-use, liquid, pharmaceutical composition comprising an ASCC component and one or more pharmaceutically acceptable excipients, wherein the composition does not require any dilution prior to administration and can be stored at controlled room temperature of about 20° C. to 25° C.±2° C. for at least one month, such as, e.g., ≥~3 months, ≥~6 months, ≥~9 months, ≥~12 months, ≥~18 months, or, e.g., ≥~24 months prior to use.

In aspects, the invention provides a process for manufacturing RTU compositions described herein wherein the process comprises terminal sterilization, wherein steps of manufacturing are performed in facility(ies) and using equipment, procedures, and personnel according to US FDA Good Manufacturing Practice (GMP) rules for non-aseptic processing.

In aspects, the invention provides a method of manufacturing ready-to-use composition(s) of ASCC(s) comprising first collecting/depositing/placing a sufficient quantity of water for injection (WFI) into a sufficiently sized vessel, e.g., a standard formulation compounding vessel. In aspects, constituents of a chelation component are added to the WFI in the vessel. In aspects, the chelation component comprises a single chelation agent. In aspects, the single chelation agent is disodium edetate. In aspects, the total quantity of the chelation component, the ASCC component, the tonicity component (e.g., sodium chloride, dextrose, or both) are added to the WFI in the vessel and allowed to dissolve to form a clear solution. The amount of ASCC(s) and all excipients in each manufactured batch of composition(s) is/are adjusted according to the desired final concentration of API (ASCC(s)). In aspects, an amount of a base such as sodium hydroxide is then added. In aspects, sodium hydroxide is added under continuous mixing. In aspects, such steps are followed by pH measurement of the solution. In aspects, the pH of the solution is adjusted by the addition of a pH adjusting component, e.g., one or more pH adjusting agents. In aspects, a final step comprises bringing the final solution of the composition up to the desired total volume using remaining WFI and the solution is filled into suitable containers, such as, e.g., vials, e.g., glass vials, each filled to a final target volume, such as, e.g., a volume representing a single dose of composition, e.g., about 10 mL, about 9 mL, about 8 mL, about 7 mL, about 6 mL, about 5 mL, about 4 mL, about 3 mL, about 2 mL, or, e.g., about 1 mL.

According to aspects, a manufacturing method, such as, e.g., a method of manufacturing conducted under (comprising) non-aseptic processing conditions, can comprise a terminal sterilization step. In aspects, terminal sterilization is accomplished using moist heat. In aspects, the terminal sterilization step destroys, e.g., reduces to a non-detectable or acceptable level of, all viable microorganisms within the final, sealed container(s) of the pharmaceutical composition.

In aspects, an autoclave is used to accomplish terminal heat-sterilization of the composition(s) in the final packaging. In aspects, a typical autoclave cycle used to achieve terminal sterilization of the final product is a cycle operating at, for example, about 121° C. for at least about 10 minutes, such as, e.g., at least about 7 minutes, ≥~8 minutes, ≥~9 minutes, ≥~10 minutes, ≥~11 minutes, ≥~12 minutes, ≥~13 minutes, ≥~14 minutes, or, e.g., at least about 15 minutes. In certain aspects, a terminal sterilization step can comprise sterile filtration. In aspects, terminal sterilization can comprise any suitable sterilization step known in the art. In aspects, such a suitable sterilization step can be any sterilization step which does not detectably or significantly negatively impact the efficacy of the composition, stability of the composition, effective dose of ASCC component, or any combination thereof.

ASCC(s) of compositions provided by the invention can be, in aspects and depending on their form, sensitive to oxidation. Further, the ASCC(s) of compositions provided by the invention can be, in aspects and depending on their form, sensitive to light. Therefore, in some respects/aspects, the API(s) of the composition (e.g., the ASCC(s)), the solution comprising ASCC(s), and filled containers (e.g., vials) comprising ASCCs can be detectably or significantly protected from exposure to air, exposure to light, or both, or protected to a maximum extent possible (e.g., using materials that are not light transmitting, airtight, etc.) during all applicable stages of manufacturing. In aspects, suitable containers for final packaging are containers which detectably or significantly, generally entirely, essentially entirely, or entirely (within the limits of current technology and detection) protect contents therein from exposure to light.

In aspects, the process used to produce a composition does not comprise terminal sterilization. In aspects, terminal sterilization can be detrimental to the composition. In aspects, sterile, ready-to-use compositions are prepared using aseptic processing techniques. In aspects, sterility is maintained throughout the manufacturing process, e.g., the process described above minus the terminal sterilization step, by use of sterile materials and a controlled working/manufacturing environment. In aspects, all containers and related apparatuses are sterilized, e.g., by heat sterilization, prior to filling. In aspects, final containers are filled under aseptic conditions, such as, e.g., by passing the composition through a filter and filling each final container to its target volume, such as volumes described above. In aspects, composition(s) can be sterile filled into container(s) to avoid the stress of terminal sterilization, such as, e.g., the stress of heat sterilization (e.g., potential detrimental effect on an ASCC or other composition component which may be imparted by terminal sterilization, such as, e.g., heat sterilization.)

In one specific aspect, the invention provides a process for the preparation of stable, ready-to-use, pharmaceutical composition(s) comprising ASCC(s) for parenteral administration comprising: an ASCC component in a concentration of between about 1.0 mg/ml to about 35.0 mg/mL, a chelation component in a concentration of about 0.001% w/v to about 0.1% w/v wherein, in aspects, the chelation component comprises a single chelating agent, and optionally a tonicity component in a concentration of about 0.1% w/v to about 5.0% w/v, a buffer component, a pH-adjusting component, and water. In general, in similar exemplary compositions described herein one or more of the components can be optionally removed from the formulation, where suitable. E.g., formulations described herein in connection with tonicity agents can be prepared without such tonicity agents, and such similar formulations lacking such one or more elements are to be considered implicitly provided herein as a part of this disclosure.

Product By Process Aspects

In aspects, the invention provides a RTU pharmaceutical composition comprising an ASCC component and one or more excipients wherein (a) all steps of the manufacturing process are performed under aseptic (inert) conditions, and (b) the resulting composition is stable according to one or more industry recognized, e.g., United States Food and Drug Administration-recognized, stability indicators, when stored at 20° C. to 25° C.±2° C. for at least one month, such as, e.g., at least about 3 months, ≥~6 months, ≥~9 months≥~12 months, ≥~18 months, or, e.g., ≥~24 months prior to use. In aspects, such compositions comprise one or more additional characteristics of composition(s) described herein, such as, e.g., comprising a chelating component, such as, e.g., a chelating component comprising a single chelating agent, the osmolality of the composition(s) is between about 270 mOsm/kg to about 340 mOsm/kg, such as, e.g., ~280 mOsm/kg to about 310 mOsm/kg, etc.

In aspects, the invention provides a RTU pharmaceutical composition for use in the treatment of scurvy, wherein (a) the composition provides an ASCC component and one or more excipients, (b) the composition is manufactured by an aseptic (inert) process not comprising terminal sterilization; and (c) the resulting product is stable when stored at 20° C. to 25° C.±2° C. for at least one month prior to use, such as, e.g., at least about 3 months, ≥~6 months, ≥~9 months, ≥~12 months, ≥~18 months, or, e.g., ≥~24 months prior to use.

In aspects, the invention provides a RTU pharmaceutical composition comprising an ASCC component and one or more excipients wherein (a) steps of the manufacturing process are performed under non-aseptic conditions and wherein the manufacturing process comprises a terminal sterilization step, and (b) the resulting composition is stable according to one or more industry recognized, e.g., United States Food and Drug Administration-recognized, stability indicators, when stored at 20° C. to 25° C.±2° C. for at least one month, such as, e.g., at least about 3 months, ≥~6 months, ≥~9 months, ≥~12 months, ≥~18 months, or, e.g., ≥~24 months prior to use. In aspects, such compositions comprise one or more additional characteristics of composition(s) described herein, such as, e.g., comprising a chelating component, such as, e.g., a chelating component comprising a single chelating agent, the osmolality of the composition(s) is between about 270 mOsm/kg to about 340 mOsm/kg, such as, e.g., ~280 mOsm/kg to about 310 mOsm/kg, etc.

In aspects, the invention provides a RTU pharmaceutical composition for use in the treatment of scurvy, wherein (a) the composition provides an ASCC component and one or more excipients, (b) the composition is manufactured under non-aseptic processing conditions and the process comprises a terminal sterilization step; and (c) the resulting product is stable when stored at 20° C. to 25° C.±2° C. for at least one month prior to use, such as, e.g., at least about 3 months, ≥~6 months, ≥~9 months, ≥~12 months, ≥~18 months, or, e.g., ≥~24 months prior to use.

In aspects, invention provides a ready-to-use pharmaceutical composition, the composition wherein the composition is manufactured by a process comprising (a) mixing a chelating component, e.g., in aspects a chelating component comprising a single chelating agent, an ascorbic acid component, e.g., an ASCC component comprising sodium ascorbate, with one or more additional excipients, e.g., excipients selected from one or more of a tonicity component, buffer component, pH-adjusting component, etc., (b) establishing a pH of the composition to be about 5 to about 8, and filling single-use containers (single-dose containers), or, e.g., in aspects, multi-use containers (multi-dose containers) with the resulting composition. In aspects, such a process is performed non-aseptically, and the process comprises a terminal sterilization step, e.g., a heat sterilization step, typically applied near or at the end of the production process. In alternative aspects, such a process is performed aseptically, wherein the process does not comprise a terminal sterilization step. In aspects, the resulting composition is suitable for use in methods comprising the treatment of scurvy. In aspects, manufacturing steps comprise mixing the ASCC component and all other excipients in a sufficient amount of water, e.g., water for injection (WFI) to form a clear solution, such that the resulting product is an aqueous solution. In aspects, the resulting composition is suitable for use in methods comprising the treatment of one or more other vitamin C-related diseases, conditions, or symptoms, such as, e.g., vitamin C-deficiency-related diseases, conditions, or symptoms.

Packaging/Delivered Form

Single-Dose Packaging

In aspects, pharmaceutically acceptable compositions provided by the invention are provided in a container component. The phrase "container(s)", in aspects, is used to reference the container component. That is, e.g., in aspects, a "container component" is a container comprising a composition of the invention, and, similarly, a "container" is a "container component" comprising a composition of the invention. In certain aspects, composition(s) provided by the invention are provided in individual, single dose containers (single dose packaging). In aspects, composition(s) provided by the invention are not provided in pharmacy bulk packaging. In aspects, composition(s) provided by the invention are packaged in individual, single dose packages/containers, each single dose package comprises a single unit dose amount of ASCC(s).

In aspects, composition(s) provided by the invention are provided in single unit dose packages/containers, wherein each single unit dose package/container comprises a ready-to-use total amount of ASCC(s) of less than about 500 mg, or, e.g., ≤~475 mg, ≤~450 mg, ≤~425 mg, ≤~400 mg, ≤~375 mg, ≤~350 mg, ≤~325 mg, ≤~300 mg, ≤~275 mg, ≤~250 mg, ≤~225 mg, ≤~200 mg, ≤~175 mg, ≤~150 mg, ≤~125 mg, ≤~100 mg, ≤~75 mg, ≤~50 mg, or, e.g., ≤~25 mg.

In aspects, composition(s) provided by the invention are provide in single unit dose packages/containers, wherein the composition is provided in a ready-to-use condition/state, and the concentration of the composition is, e.g., less than about 50 mg/mL, such as, e.g., ≤~45 mg/mL, ≤~40 mg/mL, ≤~35 mg/mL, ≤~30 mg/mL, ≤~25 mg/mL, or, e.g., ≤~20 mg/mL.

In aspects, compositions provided by the invention are provided in single unit dose packages/containers, wherein each single unit dose package/container comprises a composition in ready-to-use form, and wherein (a), the total amount of ASCC(s) provided is less than or equal to about 400 mg, the concentration of the ASCC(s) is less than about 50 mg/mL, and the composition is capable of being stored at a temperature of 20° C. to 25° C.±2° C. for at least about 1 month, such as, e.g., at least about 3 months, ≥~6 months, ≥~9 months, ≥~12 months, ≥~18 months, or, e.g., ≥~24 months prior to use.

In aspects, compositions provided by the invention are provided in single-dose packaging, wherein each single dose package/container comprises no more than about 15 mL of composition, such as, e.g., ≤~14 mL, ≤~13 mL, ≤~12 mL, ≤~11 mL, ≤~10 mL, ≤~9 mL, ≤~8 mL, ≤~7 mL, ≤~6 mL, ≤~5 mL, ≤~4 mL, ≤~3 mL, ≤~2 mL, or, e.g., ~2 mL. In aspects, compositions are provided in containers comprising about 2 mL to about 10 mL of ready-to-use composition. In aspects, a single unit dose of composition comprises between about 2 mL and about 10 mL of composition, such as, e.g., ~2 mL, ~4 mL, ~6 mL, ~8 mL, or, e.g., ~10 mL of composition. In some aspects, the entire contents of the single-use packaging can be safely administered to a single patient. In aspects, the single dose packaging is entered (e.g., penetrated with a composition withdrawal device, such as, e.g., a needle) only once. In aspects, at least about 50%, such as, e.g., ≥~55%, ≥~60%, ≥~65%, ≥~70%, ≥~75%, ≥~80%, ≥~85%, ≥~90%, ≥~95%, or, e.g., ≥~98% of the content of the single dose packaging is administered to a single patient in a method/administration or in an indication demonstrated to be effective.

In alternative aspects, compositions are provided in multi-dose containers, wherein each container contains at least two doses of composition, such as about 2, about 3, about 4, about 5, or, e.g., about 6 doses of composition. In certain aspects, the compositions provided by the invention are provided as a pharmacy bulk package (in pharmacy bulk packaging), e.g., as a sterile preparation for, e.g., parenteral use, comprising a plurality of doses, e.g., multiple single doses. In certain aspects, such preparations are RTU preparations as described elsewhere herein, and which remain stable when stored at controlled room temperature conditions as described elsewhere herein.

In aspects, the composition is packaged in a pharmaceutically acceptable container. In aspects, the packaging/container is selected from a vial, ampoule, intravenous bag, bottle, or other suitable packaging known in the art. In aspects, vials, ampoules, bottles, and the like can be made of glass.

In aspects, the ready-to-use composition(s) are provided in a pharmaceutically acceptable container such as plastic intravenous bags, including, e.g., pre-mix bags and admix bags or bottles. In aspects, intravenous bags well known in the art and commercially available are used. In aspects, composition(s) are provided in intravenous containers comprising a polymeric contact surface, such as, e.g., a surface comprising ethylene-propylene copolymer, polyethylene, polyolefin blend or ethylene-vinyl acetate.

In aspects, the ready-to-use compositions provided by the invention are packaged in a glass container. In some aspects, the pharmaceutical compositions are packaged in USP Type I borosilicate glass vials or USP Type II soda lime silica glass vials. In some respects, the glass packaging/container can be clear glass. In some aspects, packages can be used that reduce the amount of light which can reach the composition. In some respects, the glass packaging/container can be a colored or tinted glass, so as to detectably or significantly reduce the amount of light exposure of the compositions held therein. In some respects, the glass packaging/container can be amber glass. In aspects, the packaging/container is amber glass vials. In some aspects, the package/container can, optionally, further comprise an additional light barrier, such as, e.g., an aluminum over-pouch or a carton.

In certain aspects, the packaging/containers can be capable of holding about 1 mL to about 200 mL of composition. For example, in aspects, the packaging/containers can be, e.g., glass vials, e.g., clear, or amber glass vials, capable of holding about 1 mL to about 200 mL of composition, such as, e.g., 2 mL, 4 mL, 8 mL, 10 mL, 20 mL, 50 mL, 100 mL, or 200 ml vials.

In aspects, packaging/containers, e.g., glass vials, have a USP Elastomer Closure for Injections described under and meeting the requirements of USP<381> (elastomeric stopper). In aspects, the closure, e.g., a stopper, is selected from a butyl, EPDM, natural rubber, nitrile, or silicone material. In aspects, the closure, e.g., stopper, comprises a butyl material. In aspects, the butyl material (e.g., butyl stopper) is selected from a chlorobutyl or bromobutyl stopper. In some aspects, the package/container is closed by both a stopper and a cap. In aspects, the cap can be an aluminum cap. In aspects, a stopper, a cap, or both, is/are coated with a silicone, B2 crosslinked coating, Flurotec coating, Teflon coating, Westar RS treatment, RTS treatment, or thermoplastic elastomer (TPE) product. In some aspects, the package/container, e.g., glass vial, is closed with a bromobutyl stopper and sealed with aluminum caps.

According to one aspect, the invention provides a ready-to-use pharmaceutical composition comprising an ASCC component for parenteral administration provided in single-use packaging, wherein the entire contents of the single-use packaging can be safely administered to a single patient, and wherein the single-dose packaging comprises no more than about 400 mg of the ASCC component and no more than about 10 mL of composition.

According to certain aspects, the invention provides a collection of single dose containers, each providing a single dose of composition(s) described herein. In aspects, each single dose of the collection of single doses comprises the same concentration of ASCC component. In aspects, at least two single doses of the collection of single doses comprises a different concentration of ASCC component. In aspects, each single dose of the collection of single doses comprises the same total amount of ASCC component. In aspects, at least two single doses of the collection of single doses comprises a different total amount of ASCC component. In aspects, each single dose of the collection of single dose containers comprises the same volume of composition. In aspects, at least two single doses of the collection of single doses comprises a different volume of composition.

Kits (Collections of Compositions and Administration Devices)

According to aspects, the invention provides a kit comprising one or more packaged composition(s) or unit dose compositions described herein. In aspects, such a "kit" or collection of components further comprises a device for collecting or administering the composition, e.g., withdrawing, the composition from its packaging/container, such as, e.g., a needle, syringe, or both (e.g., a needle and syringe system). In aspects, the collection or withdrawal/administration device is maintained as a sterile device in the kit (e.g., it is maintained in sterile packaging). In aspects, the device is capable of collecting the composition from its packaging in a sterile manner, without introducing detectable or significant contamination. In aspects, such a needle, syringe, or needle and syringe system is known in the art.

In aspects, a kit can comprise one or more containers comprising a single unit dose of composition. In aspects, a kit can comprise multiple unit doses of composition. In aspects, a kit comprises multiple unit doses of composition each comprising the same volume of composition. In aspects, a kit comprises multiple unit doses of composition each comprising the same total amount of ASCC(s). In aspects, a kit comprises multiple unit doses of composition each comprising a composition having the same concentration of ASCC(s). In aspects, a kit comprises multiple unit doses of composition, each comprising a different volume of composition, a different total amount of ASCC(s), a different concentration of ASCC(s), or any combination thereof.

In aspects, kit packaging can aid in the protection of compositions held therein from light exposure during storage, such that the kit packaging detectably or significantly reduces the amount of light reaching the compositions prior to their extraction/removal from the kit prior to use.

Stored at Room Temperature

According to aspects, composition(s) provided by the invention are characterizable as being able to be stored at controlled room temperature, e.g., temperatures between about 20° C. and about 30° C., such as, e.g., 20° C. to about 25° C., such as, for example, about 25° C.±2° C. In aspects, composition(s) provided by the invention are characterizable as not requiring storage at refrigerated temperatures or freezing temperatures, such as, e.g., temperatures at or below about 4° C.

In aspects, compositions provided by the invention are stable (e.g., stable as determined by one or more stability determinants/assays described herein) when stored at temperatures above 0° C., such as, e.g., temperatures >2° C., >4° C., >6° C., >8° C., >10° C., >12° C., >16° C., >20° C., >22° C., >24° C., >26° C., or >28° C., but less than or equal to about >30° C., for a period of at least about 1 month, such as, e.g., ≥~2 months, ≥~3 months, ≥~6 months, ≥~9 months, ≥~12 months, ≥~18 months, or, e.g., ≥~24 months prior to use. As stated elsewhere herein, in aspects, compositions provided by the invention do not require storage under refrigerated conditions in order to maintain stability during shipment or storage periods. In aspects, compositions do not require any period of freezer storage in order to maintain stability, effectiveness, and the like.

In one general aspect, there is provided a stable ready-to-use pharmaceutical compositions of ASCC(s), wherein the composition does not require dilution prior to administration and can be stored at controlled room temperature for a period of at least about 1 month, such as, e.g., at least ~3, ~6, ~9, ~12, or at least about 18 or 24 months prior to use.

EXEMPLARY ASPECTS OF THE INVENTION

The following is a non-limiting list of exemplary aspects of the invention.

In aspects, the invention provides a ready-to-use (RTU) parentally administrable pharmaceutical composition comprising (a) a pharmaceutically effective amount of an ascorbic acid compound component and (b) one or more pharmaceutically acceptable excipients, wherein the composition can be stored at 20° C. to 25° C.±2° C. for at least about one month prior to use, wherein the pharmaceutical composition is pharmaceutically acceptable when obtained from storage under suitable conditions and thereafter directly administered parenterally to a patient (aspect 1).

In aspects, the invention provides the ready-to-use pharmaceutical composition of aspect 1, wherein the ascorbic acid compound component comprises ascorbic acid (aspect 2).

In aspects, the invention provides the ready-to-use pharmaceutical composition of aspect 2, wherein the ascorbic acid is L-ascorbic acid (aspect 3).

In aspects, the invention provides the ready-to-use pharmaceutical composition of aspect 1, wherein the ascorbic acid compound component comprises a derivative of ascorbic acid (aspect 4).

In aspects, the invention provides the ready-to-use pharmaceutical composition of aspect 4, wherein the ascorbic acid derivative is an ascorbic acid salt (aspect 5).

In aspects, the invention provides the ready-to-use pharmaceutical composition of aspect 5, wherein the ascorbic acid salt is sodium ascorbate (aspect 6).

In aspects, the invention provides the ready-to-use pharmaceutical composition of any one or more of aspects 1-6, wherein the concentration of the ascorbic acid compound component is about 1 mg/mL to about 50 mg/mL or is, e.g. (as is applicable throughout the exemplary aspects of the invention as described herein) present in an amount which is equivalent to such an amount of ascorbic acid (aspect 7).

In aspects, the invention provides the ready-to-use pharmaceutical composition of aspect 7, wherein the concentration of the ascorbic acid compound component is about 1 mg/mL to about 35 mg/mL (aspect 8).

In aspects, the invention provides the ready-to-use pharmaceutical composition of aspect 8, wherein the concentration of the ascorbic acid compound component is about 15 mg/mL-about 25 mg/mL, such as about 25 mg/mL (aspect 9).

In aspects, the invention provides the ready-to-use pharmaceutical composition of any one or more of aspects 1-9, wherein the one or more excipients comprises, mostly comprises, generally consists of, consists essentially of, or consists of a tonicity component comprising, mostly comprising, generally consisting of, consisting essentially of, or consisting of one or more tonicity agent(s), and wherein one or more tonicity agent(s) optionally comprise, mostly comprise, or consist of one or more of sodium chloride, dextrose, sucrose, xylitol, fructose, glycerol, sorbitol, mannitol, potassium chloride, mannose, calcium chloride, and magnesium chloride (aspect 10).

In aspects, the invention provides the ready-to-use pharmaceutical composition of aspect 10, wherein the one or more tonicity agent(s) are present in an amount/concentration effective in establishing an osmolality of the composition of about 270 mOsm/kg to about 340 mOsm/kg (aspect 11).

In aspects, the invention provides the ready-to-use pharmaceutical composition of one or both of aspect 10 or aspect 11, wherein the tonicity agent(s) comprise, mostly comprise, generally consist of, consist essentially of, or consists of one or more of sodium chloride, dextrose, or sodium chloride and dextrose (aspect 12).

In aspects, the invention provides the ready-to-use pharmaceutical composition of any one or more of aspects 10-12, wherein the composition comprises sodium chloride in an amount of about 0.1% w/v to about 0.9% w/v and dextrose in an amount of about 0.1% w/v to about 5% w/v (aspect 13).

In aspects, the invention provides the ready-to-use pharmaceutical composition of any one or more of aspects 10-13, wherein the ratio of the ascorbic acid compound to the tonicity component is about 1:50 to about 1:0.018 (aspect 14).

In aspects, the invention provides the ready-to-use pharmaceutical composition of any one or more of aspects 1-14, wherein the composition is adapted to be administered to a recipient by a parenteral route of administration, is in a device adapted for parental delivery, have been proven to be safe and effective when parentally delivered, or a combination of any or all thereof, where in parental delivery includes intravenous administration, subcutaneous administration, intramuscular administration, intra-atrial administration, or intra-arterial continuous infusion (aspect 15).

In aspects, the invention provides the ready-to-use pharmaceutical composition of aspect 15, wherein the composition is formulated to be administered intravenously, placed in a device for intravenous administration, or both, or the composition has been demonstrated to be safe and effective in a significant number of patients when delivered intravenously (aspect 16).

In aspects, the invention provides the ready-to-use pharmaceutical composition of aspect 16, wherein the composition has been demonstrated to be safe and effective (in a significant number of patients, through bioequivalence, or otherwise) when administered intravenously at a rate of about 1 mg/min to about 50 mg/min (aspect 17).

In aspects, the invention provides the ready-to-use pharmaceutical composition of aspect 17, wherein the composition has been demonstrated to be safe and effective when administered intravenously at a rate of about 1.3 mg/min to about 33 mg/min (aspect 18).

In aspects, the invention provides the ready-to-use pharmaceutical composition of any one or more of aspects 1-18, wherein the composition has been demonstrated to be safe and effective when administered at least once per day for up to about 7 days (aspect 19).

In aspects, the invention provides the ready-to-use pharmaceutical composition of aspect 19, wherein the composition has been demonstrated to be safe and effective when administered at least two times per day for up to about 7 days (aspect 20).

In aspects, the invention provides the ready-to-use pharmaceutical composition of aspect 20, wherein the composition has been demonstrated to be safe and effective when the composition is administered at least three times per day for up to about 7 days (aspect 21).

In aspects, the invention provides the ready-to-use pharmaceutical composition of aspect 21, wherein the composition has been demonstrated to be safe and effective when administered at least four times per day for up to about 7 days (aspect 22).

In aspects, the invention provides the ready-to-use pharmaceutical composition of any one or more of aspects 1-22, wherein the composition has been demonstrated to be safe and effective for human recipients (patients) of at least 5 months of age (aspect 23).

In aspects, the invention provides the ready-to-use pharmaceutical composition of any one or more of aspects 1-23, wherein the composition has been demonstrated to be safe and effective for human patients for whom oral ascorbic acid compound administration is not possible or the composition has been proven to be effective (aspect 24).

In aspects, the invention provides the ready-to-use pharmaceutical composition of any one or more of aspects 1-24, wherein the composition has been demonstrated to be safe and effective when administered to human patients for whom prior oral ascorbic acid compound administration has been unsuccessful or insufficient (aspect 25).

In aspects, the invention provides the ready-to-use pharmaceutical composition of any one or more of aspects 1-25, wherein the composition has been demonstrated to be safe and effective for administration to human recipients for whom oral ascorbic acid compound administration is contraindicated (aspect 26).

In aspects, the invention provides the ready-to-use pharmaceutical composition of any one or more of aspects 1-26 wherein at least one of the one or more pharmaceutically acceptable excipients is selected from the group consisting of chelating agent(s), stabilizing agent(s), buffer(s), pH adjusting agent(s), antioxidant(s), preservative(s), and carrier(s) (aspect 27).

In aspects, the invention provides the ready-to-use pharmaceutical composition of aspect 27, wherein the one or more pharmaceutically acceptable excipients comprises a chelation component (aspect 28).

In aspects, the invention provides the ready-to-use pharmaceutical composition of aspect 28, wherein the chelation component comprises, mostly comprises, generally consists of, consists essentially of, or consists of a single chelation agent (aspect 29).

In aspects, the invention provides the ready-to-use pharmaceutical composition of aspect 29, wherein the single chelation agent is edetate disodium (aspect 30).

In aspects, the invention provides the ready-to-use pharmaceutical composition of any one or more of aspects 28-30, wherein the chelation component is present in an amount of about 0.001% w/v to about 0.1% w/v (aspect 31).

In aspects, the invention provides the ready-to-use pharmaceutical composition of aspect 31, wherein the chelation component comprises only a single chelation agent (aspect 32).

In aspects, the invention provides the ready-to-use pharmaceutical composition of aspect 32, wherein the single chelation agent is edetate disodium (aspect 33).

In aspects, the invention provides the ready-to-use pharmaceutical composition of any one or more of aspects 28-33, wherein the ratio of the ascorbic acid compound to the chelation component is less than about 1:0.0004 (aspect 34).

In aspects, the invention provides the ready-to-use pharmaceutical composition of aspect 34, wherein the ratio of the ascorbic acid compound to the chelation component is between about 1:0.04 to about 1:0.0004 (aspect 35).

In aspects, the invention provides the ready-to-use pharmaceutical composition of any one or more of aspects 27-35, wherein the one or more pharmaceutically acceptable excipients comprises a buffer component, a pH component, or both, wherein the buffer component, pH component, or both comprise, mostly comprise, generally consist of, consist essentially of, or consist of one or more of sodium bicarbonate, hydrochloride acid, and sodium hydroxide (aspect 36).

In aspects, the invention provides the ready-to-use pharmaceutical composition of any one or more of aspects 1-36, wherein the concentration of ascorbic acid compound component in the composition is less than about 50 mg/mL (aspect 37).

In aspects, the invention provides the ready-to-use pharmaceutical composition of any one or more of aspects 1-37, wherein the concentration of ascorbic acid compound component in the composition is less than about 45 mg/mL (aspect 38).

In aspects, the invention provides the ready-to-use pharmaceutical composition of any one or more of aspects 1-38, wherein the concentration of ascorbic acid compound component in the composition is less than about 40 mg/mL (aspect 39).

In aspects, the invention provides the ready-to-use pharmaceutical composition of any one or more of aspects 1-39, wherein the concentration of ascorbic acid compound component in the composition is less than about 35 mg/mL (aspect 40).

In aspects, the invention provides the ready-to-use pharmaceutical composition of any one or more of aspects 1-40, wherein the concentration of ascorbic acid compound component in the composition is less than about 30 mg/mL (aspect 41).

In aspects, the invention provides the ready-to-use pharmaceutical composition of any one or more of aspects 1-41, wherein the concentration of ascorbic acid compound component in the composition is about 25 mg/mL (aspect 42).

In aspects, the invention provides the ready-to-use pharmaceutical composition of any one or more of aspects 1-42, wherein the composition is provided in a single dose, ready-to-use package, and the total amount of ascorbic acid compound component provided in a single dose, ready-to-use packaging of the composition is less than about 350 mg (aspect 43).

In aspects, the invention provides the ready-to-use pharmaceutical composition of any one or more of aspects 1-43, wherein the composition is provided in a single dose, ready-to-use package, and the total amount of ascorbic acid compound component provided in a single dose, ready-to-use packaging of the composition is less than about 300 mg (aspect 44).

In aspects, the invention provides the ready-to-use pharmaceutical composition of any one or more of aspects 1-44, wherein the composition is provided in a single dose, ready-to-use package, and the total amount of ascorbic acid compound component provided in a single dose, ready-to-use packaging of the composition is less than about 250 mg (aspect 45).

In aspects, the invention provides the ready-to-use pharmaceutical composition of any one or more of aspects 1-45, wherein the composition is provided in a single dose, ready-to-use package, and the total amount of ascorbic acid compound component provided in a single dose, ready-to-use packaging of the composition is less than about 200 mg (aspect 46).

In aspects, the invention provides the ready-to-use pharmaceutical composition of any one or more of aspects 1-46, wherein the composition is provided in a single dose, ready-to-use package, and the total amount of ascorbic acid compound component provided in a single dose, ready-to-use packaging of the composition is less than about 150 mg (aspect 47).

In aspects, the invention provides the ready-to-use pharmaceutical composition of any one or more of aspects 1-47, wherein the composition is provided in a single dose, ready-to-use package, and the total amount of ascorbic acid compound component provided in a single dose, ready-to-use packaging of the composition is less than about 100 mg (aspect 48).

In aspects, the invention provides the ready-to-use pharmaceutical composition of any one or more of aspects 1-48, wherein the composition is provided in a single dose, ready-to-use package, and the total amount of ascorbic acid compound component provided in a single dose, ready-to-use packaging of the composition is less than about 50 mg (aspect 49).

In aspects, the invention provides the ready-to-use pharmaceutical composition of any one or more of aspects 1-49, wherein the composition is contained in an airtight container and the pressure within airtight packaging containing the composition during storage of the composition does not increase by an amount indicative of composition instability as determined by one or more industry recognized stability measures (aspect 50).

In aspects, the invention provides the ready-to-use pharmaceutical composition of any one or more of aspects 1-50, wherein the composition is packaged in single-dose, single administration packaging comprising no more than about 10 mL of the composition (aspect 51).

In aspects, the invention provides the ready-to-use pharmaceutical composition of aspect 51, wherein the composition is packaged in single-dose, single administration packaging comprising no more than about 8 mL of the composition (aspect 52).

In aspects, the invention provides the ready-to-use pharmaceutical composition of aspect 52, wherein the composition is packaged in single-dose, single administration packaging comprising no more than about 6 mL of the composition (aspect 53).

In aspects, the invention provides the ready-to-use pharmaceutical composition of aspect 53, wherein the composition is packaged in single-dose, single administration packaging comprising no more than about 4 mL of the composition (aspect 54).

In aspects, the invention provides the ready-to-use pharmaceutical composition of aspect 54, wherein the composition is packaged in single-dose, single administration packaging comprising no more than about 2 mL of the composition (aspect 55).

In aspects, the invention provides the ready-to-use pharmaceutical composition of any one or more of aspects 51-55, wherein the entire contents of the single-use packaging can be safely administered to a single patient (aspect 56).

In aspects, the invention provides the ready-to-use pharmaceutical composition of any one or more of aspects 1-56, wherein the amount of ascorbic acid compound component present after 1 month of storage at 20° C. to 25° C.±2° C. is at least 90% of the amount of the ascorbic acid compound component present in the composition at the time of packaging (aspect 57).

In aspects, the invention provides the ready-to-use pharmaceutical composition of aspect 57, wherein the amount of ascorbic acid compound component present after 3 months of storage at 20° C. to 25° C.±2° C. is at least 90% of the amount of the ascorbic acid compound component present in the composition at the time of packaging (aspect 58).

In aspects, the invention provides the ready-to-use pharmaceutical composition of aspect 58, wherein the amount of ascorbic acid compound component present after 6 months of storage at 20° C. to 25° C.±2° C. is at least 90% of the amount of the ascorbic acid compound component present in the composition at the time of packaging (aspect 59).

In aspects, the invention provides the ready-to-use pharmaceutical composition of aspect 59, wherein the amount of ascorbic acid compound component present after 9 months of storage at 20° C. to 25° C.±2° C. is at least 90% of the amount of the ascorbic acid compound component present in the composition at the time of packaging (aspect 60).

In aspects, the invention provides the ready-to-use pharmaceutical composition of aspect 60, wherein the amount of ascorbic acid compound component present after 12 months of storage at 20° C. to 25° C.±2° C. is at least 90% of the amount of the ascorbic acid compound component present in the composition at the time of packaging (aspect 61).

In aspects, the invention provides the ready-to-use pharmaceutical composition of aspect 61, wherein the amount of ascorbic acid compound component present after 18 months of storage at 20° C. to 25° C.±2° C. is at least 90% of the amount of the ascorbic acid compound component present in the composition at the time of packaging (aspect 62).

In aspects, the invention provides the ready-to-use pharmaceutical composition of any one or more of aspects 1-62, wherein the composition passes the Particulate Matter Test under USP<788> at the time of manufacture and when stored at 20° C. to 25° C.±2° C. for at least about 1 month (aspect 63).

In aspects, the invention provides the ready-to-use pharmaceutical composition of any one or more of aspects 1-63, wherein the composition passes the pH test under USP<791> with a variation±0.5 pH unit(s) compared to original pH when stored at 20° C. to 25° C.±2° C. for at least about 1 month (aspect 64).

In aspects, the invention provides the ready-to-use pharmaceutical composition of any one or more of aspects 1-64, wherein the composition passes the Completeness of Solution Test under USP<641>, exhibiting a clear solution at the time of manufacture and when stored at 20° C. to 25° C.±2° C. for at least about 1 month (aspect 65).

In aspects, the invention provides the ready-to-use pharmaceutical composition of any one or more of aspects 1-65, wherein the composition passes the Visible Particles test under USP<790>, exhibiting absence of visible particles at the time of manufacture and when stored at 20° C. to 25° C.±2° C. for at least about 1 month (aspect 66).

In aspects, the invention provides the ready-to-use pharmaceutical composition of any one or more of aspects 1-66, wherein the composition demonstrates an amount of ascorbic acid compound as measured by HPLC which is 95-105% of initial value (at the time of manufacture) under USP<621> when stored at 20° C. to 25° C.±2° C. for at least about 1 month (aspect 67).

In aspects, the invention provides the ready-to-use pharmaceutical composition of any one or more of aspects 1-67, wherein the composition does not exhibit more than 0.1% ascorbic acid related impurity(ies) by HPLC under USP<621> at the time of manufacture and when stored at 20° C. to 25° C.±2° C. for at least about 1 month (aspect 68).

In aspects, the invention provides the ready-to-use pharmaceutical composition of any one or more of aspects 1-68, wherein the composition does not exhibit more than 0.1% of any single unidentified impurity by HPLC under USP<621> at the time of manufacture and when stored at 20° C. to 25° C.±2° C. for at least about 1 month (aspect 69).

In aspects, the invention provides the ready-to-use pharmaceutical composition of any one or more of aspects 1-69, wherein the composition does not exhibit more than 0.4% total impurities by HPLC under USP<621> at the time of manufacture and when stored at 20° C. to 25° C.±2° C. for at least about 1 month (aspect 70).

In aspects, the invention provides the ready-to-use pharmaceutical composition of any one or more of aspects 1-70, wherein the composition exhibits a Total Aerobic Microbial Count (TAMC) of ≤10 cfu/100 mL by USP <621> at the time of manufacture and when stored at 20° C. to 25° C.±2° C. for at least about 1 month (aspect 71).

In aspects, the invention provides the ready-to-use pharmaceutical composition of any one or more of aspects 1-71, wherein the composition exhibits a Total Yeast and Molds Count (TYMC) of ≤10 cfu/100 mL by USP <621> at the time of manufacture and when stored at 20° C. to 25° C.±2° C. for at least about 1 month (aspect 72).

In aspects, the invention provides the ready-to-use pharmaceutical composition of any one or more of aspects 1-72, wherein the composition exhibits ≤35 IU/mL Endotoxins by USP<85> at the time of manufacture and when stored at 20° C. to 25° C.±2° C. for at least about 1 month (aspect 73).

In aspects, the invention provides the ready-to-use pharmaceutical composition of any one or more of aspects 1-73, wherein the composition is characterizable as sterile by USP <71> at the time of manufacture and when stored at 20° C. to 25° C.±2° C. for at least about 1 month (aspect 74).

In aspects, the invention provides the ready-to-use pharmaceutical composition of any one or more of aspects 1-74, wherein the composition has a pH of about 5 to about 8 by USP <791> at the time of manufacture and when stored at 20° C. to 25° C.±2° C. for at least about 1 month (aspect 75).

In aspects, the invention provides the ready-to-use pharmaceutical composition of any one or more of aspects 63-75, wherein the one or more characteristic(s) described by the aspect(s) is/remains true in a significant number of cases or all cases when the composition is stored at 20° C. to 25° C.±2° C. for at least about 3 months (aspect 76).

In aspects, the invention provides the ready-to-use pharmaceutical composition of any one or more of aspects 63-76, wherein the one or more characteristic(s) described by the aspect(s) is/remains true in a significant number of cases or all cases when the composition is stored at 20° C. to 25° C.±2° C. for at least about 6 months (aspect 77).

In aspects, the invention provides the ready-to-use pharmaceutical composition of any one or more of aspects 63-77, wherein the one or more characteristic(s) described by the aspect(s) is/remains true in a significant number of cases or all cases when the composition is stored at 20° C. to 25° C.±2° C. for at least about 9 months (aspect 78).

In aspects, the invention provides the ready-to-use pharmaceutical composition of any one or more of aspects 63-78, wherein the one or more characteristic(s) described by the aspect(s) is/remains true in a significant number of cases or all cases when the composition is stored at 20° C. to 25° C.±2° C. for at least about 12 months (aspect 79).

In aspects, the invention provides the ready-to-use pharmaceutical composition of any one or more of aspects 63-79, wherein the one or more characteristic(s) described by the aspect(s) is/remains true in a significant number of cases or all cases when the composition is stored at 20° C. to 25° C.±2° C. for at least about 18 months (aspect 80).

In aspects, the invention provides the ready-to-use pharmaceutical composition of any one or more of aspects 1-80, wherein the composition does not require dilution prior to use (aspect 81).

In aspects, the invention provides a ready-to-use pharmaceutical composition comprising (a) an ascorbic acid compound component in an amount of less than 50 mg/mL (or, e.g., is present in a form, e.g., salt form, in an amount which is less than such an amount of ascorbic acid, with appropriate weight conversion(s) applied) and (b) a chelation component, wherein the ratio of the ascorbic acid compound component the chelation component is less than 1:0.0004, and wherein the composition can be stored at 20° C. to 25° C.±2° C. for at least about one month prior to use (aspect 82).

In aspects, the invention provides the ready-to-use pharmaceutical composition of aspect 82, wherein the composition further comprises any one or more of the characteristics of compositions described in any one or more of aspects 1-81 (aspect 83).

In aspects, the invention provides a ready-to-use pharmaceutical composition comprising (a) an ascorbic acid compound component in an amount of less than 50 mg/mL and (b) a single chelating agent, wherein the composition can be stored at 20° C. to 25° C.±2° C. for at least about one month prior to use (aspect 84).

In aspects, the invention provides the ready-to-use pharmaceutical composition of aspect 84, wherein the composition further comprises any one or more of the characteristics of compositions described in any one or more of aspects 1-81 (aspect 85).

In aspects, the invention provides a ready-to-use pharmaceutical composition comprising (a) an ascorbic acid compound component, and (b) one or more tonicity agent(s), wherein the ratio of the ascorbic acid compound and the one or more tonicity agent(s) during storage and prior to the administration of the composition, is about 1:2-1:0.04 (aspect 86).

In aspects, the invention provides the ready-to-use pharmaceutical composition of aspect 86, wherein the composition further comprises any one or more of the characteristics of compositions described in any one or more of aspects 1-81 (aspect 87).

In aspects, the invention provides a ready-to-use pharmaceutical composition comprising an ascorbic acid compound component, wherein the composition is provided in packaging comprising no more than 350 mg of the compound, and wherein the composition is capable of being stored at a temperature of 20° C. to 25° C.±2° C. for at least 1 month (aspect 88).

In aspects, the invention provides the ready-to-use pharmaceutical composition of aspect 88, wherein the composition further comprises any one or more of the characteristics of compositions described in any one or more of aspects 1-81 (aspect 89).

In aspects, the invention provides a ready-to-use pharmaceutical composition for parenteral administration comprising (a) an ascorbic acid compound component in a concentration of about 1.0 mg/mL to about 35.0 mg/mL, (b) one or more tonicity agents in a concentration of about 0.1% w/v to about 5.0% w/v, (c) a chelation component in a concentration of about 0.001% w/v to about 0.1% w/v, (d) one or more buffers or pH-adjusting agents, and (e) a carrier (aspect 90).

In aspects, the invention provides the ready-to-use pharmaceutical composition of aspect 90, wherein the composition further comprises any one or more of the characteristics of compositions described in any one or more of aspects 1-81 (aspect 91).

In aspects, the invention provides a ready-to-use, pharmaceutical composition for parenteral administration, comprising (a) an ascorbic acid compound component in an amount of no more than about 350 mg, (b) one or more tonicity agents in an amount of no more than about 10- about 600 mg, (c) a chelation component in an amount of no more than about 0.1-10 mg, (d) one or more buffers or pH-adjusting agents, and (e) a carrier (aspect 92).

In aspects, the invention provides the ready-to-use pharmaceutical composition of aspect 92, wherein the composition further comprises any one or more of the characteristics of compositions described in any one or more of aspects 1-81 (aspect 93).

In aspects, the invention provides a ready-to-use pharmaceutical composition for parenteral administration comprising an ascorbic acid compound component, one or more tonicity agent(s), and one or more pharmaceutically acceptable excipients, wherein the composition can be stored for a period of at least 1 month at controlled room temperature in an airtight container without an increase in pressure within the container indicative of instability of the composition or component(s) thereof as measured by an applicable United States Pharmacopeia (such as specifically the United States Pharmacopeia-National Formulary (USP-NF) version USP-NF 2021, Issue 3, dated Dec. 1, 2021) defined test indicative of product stability (aspect 94).

In aspects, the invention provides the ready-to-use pharmaceutical composition of aspect 94, wherein the composition further comprises any one or more of the characteristics of compositions described in any one or more of aspects 1-81 (aspect 95).

In aspects, the invention provides a ready-to-use pharmaceutical composition comprising an ascorbic acid compound component for parenteral administration provided in single-use packaging, wherein the entire contents of the single-use packaging can be safely administered to a single patient, and wherein the single-dose packaging comprises no more than about 10 mL of composition (aspect 96).

In aspects, the invention provides the ready-to-use pharmaceutical composition of aspect 96, wherein the composition further comprises any one or more of the characteristics of compositions described in any one or more of aspects 1-81 (aspect 97).

In aspects, the invention provides a method of treating scurvy in an individual diagnosed with scurvy, the method comprising administration of a composition comprising an ascorbic acid compound component, wherein the composition has any one or more of the characteristics described in any one or more of aspects 1-81 (aspect 98).

In aspects, the invention provides a method of treating scurvy in an individual diagnosed with scurvy, the method comprising administering an individually packaged dose of a composition provided in ready-to-use form, the composition having any one or more of the characteristics described in any one or more of aspects 1-81 (aspect 99).

In aspects, the invention provides a method of treating scurvy in an individual, the method comprising administering an individually packaged dose of a composition provided in ready-to-use form, the composition comprising an ascorbic acid compound component present in the composition in a total amount of no more than 350 mg (aspect 100).

In aspects, the invention provides the method of aspect 100, wherein the composition further comprises any one or more of the characteristics of compositions described in any one or more of aspects 1-81 (aspect 101).

In aspects, the invention provides a method of treating scurvy in an individual, the method comprising administering an individually packaged dose of a composition provided in ready-to-use form, the composition comprising an ascorbic acid compound component present in the composition in a concentration of no more than 50 mg/mL (aspect 102).

In aspects, the invention provides the method of aspect 102, wherein the composition further comprises any one or more of the characteristics of compositions described in any one or more of aspects 1-81 (aspect 103).

In aspects, the invention provides a method of treating scurvy in a population of patients diagnosed with scurvy, wherein (a) the population of patients comprises at least 2 patients requiring a different total amount of ascorbic acid compound per dose; (b) the method comprises administering to each patient of the population of patients an individually packaged, ready-to-use, single dose of a composition comprising an ascorbic acid compound component, stable when stored at about 20° C. to 25° C.±2° C. for a period of at least 1 month, and (c) the method results in an amount of waste of the ascorbic acid compound(s) which is detectably or significantly less than the amount of an ascorbic acid compound left unused with respect to treatment of scurvy in a similar population of patients with the product approved under the United States Food and Drug Administration NDA number 209112 (ASCOR®) (aspect 104).

In aspects, the invention provides the method of aspect 104, wherein the composition further comprises any one or more of the characteristics of compositions described in any one or more of aspects 1-81 (aspect 105).

In aspects, the invention provides a method of treating scurvy in a population of patients diagnosed with scurvy, wherein the method comprises administration of at least one individually packaged, ready-to-use single dose of a composition comprising an ascorbic acid compound component, wherein the risk of administering to any single patient within the population of patients a total amount of the ascorbic acid compound(s) other than the intended total amount of the ascorbic acid compound(s) is detectably or significantly less than the risk of administering to any single patient within a similar population of patients treated with the product approved under the United States Food and Drug Administration NDA number 209112 (ASCOR®) a total amount of ascorbic acid compound other than the intended total amount of ascorbic acid compound (aspect 106).

In aspects, the invention provides the method of aspect 106, wherein the composition further comprises any one or more of the characteristics of compositions described in any one or more of aspects 1-81 (aspect 107).

In aspects, the invention provides a method of treating scurvy in a population of patients diagnosed with scurvy, wherein the method comprises administration of at least one individually packaged, ready-to-use, single dose of a composition comprising an ascorbic acid compound component, wherein the method results in a risk of contaminating the composition prior to administration of the composition to any single patient within the population of patients which is detectably or significantly less than the risk of contaminating a second composition approved under the United States Food and Drug Administration NDA number 209112 (ASCOR®) prior to the administration of ASCOR® for treating scurvy in a similar population of patients (aspect 108).

In aspects, the invention provides the method of aspect 108, wherein the composition further comprises any one or more of the characteristics of compositions described in any one or more of aspects 1-81 (aspect 109).

In aspects, the invention provides a method of treating scurvy in a patient diagnosed with scurvy with a ready-to-use composition comprising an ascorbic acid compound component, wherein the composition (a) is stable when stored at 20° C. to 25° C.±2° C. for at least about one month prior to use, and (b) is provided in a single dose container entered a single time by a collection device when being administered to a patient (aspect 110).

In aspects, the invention provides the method of aspect 110, wherein the composition further comprises any one or more of the characteristics of compositions described in any one or more of aspects 1-81 (aspect 111).

In aspects, the invention provides a method of treating vitamin C deficiency in an individual diagnosed with vitamin C deficiency, the method comprising administration of a composition comprising an ascorbic acid compound component, wherein the composition has any one or more of the characteristics described in any one or more of aspects 1-81 (aspect 112).

In aspects, the invention provides a method of treating vitamin C deficiency in an individual diagnosed with vitamin C deficiency, the method comprising administering an individually packaged dose of a composition comprising an ascorbic acid compound component provided in ready-to-use form, the composition having any one or more of the characteristics described in any one or more of aspects 1-81 (aspect 113).

In aspects, the invention provides a method of treating a vitamin C deficiency in a patient, the method comprising administration of a ready-to-use composition comprising (a) an ascorbic acid compound component, (b) at least one of a chelation component, a tonicity component, or both, and (c) one or more additional excipients, wherein the composition is stable when stored between 20° C. to 25° C.±2° C. for at least about one month (aspect 114).

In aspects, the invention provides the method of aspect 114, wherein the composition further comprises any one or more of the characteristics of compositions described in any one or more of aspects 1-81 (aspect 115).

In aspects, the invention provides a method of treating a vitamin C deficiency in a patient, the method comprising administration of a ready to use composition comprising (a) an ascorbic acid compound which is (I) present in an amount of less than 350 mg, (II) present in a concentration of no more than 50 mg/mL, or (III) both (I) and (II), (b) at least one of a chelation component, tonicity component, or both and (c) one or more additional excipients, wherein the composition is stable when stored between 20° C. to 25° C.±2° C. for at least about one month (aspect 116).

In aspects, the invention provides the method of aspect 116, wherein the composition further comprises any one or more of the characteristics of compositions described in any one or more of aspects 1-81 (aspect 117).

In aspects, the invention provides a method of detectably or significantly decreasing the healing time of a wound in a mammal suffering therefrom, the method comprising administration of a composition comprising an ascorbic acid compound component, wherein the composition has any one or more of the characteristics described in any one or more of aspects 1-81 (aspect 118).

In aspects, the invention provides a method of detectably or significantly decreasing the healing time of a wound in a mammal suffering therefrom, the method comprising administering an individually packaged dose of a composition provided in ready-to-use form, the composition having any one or more of the characteristics described in any one or more of aspects 1-81 (aspect 119).

In aspects, the invention provides a method of detectably or significantly decreasing the healing time of a wound in a mammal suffering therefrom, the method comprising administration of a ready-to-use composition comprising (a) an ascorbic acid compound component, (b) at least one of a chelation component, a tonicity component, or both, and (c) one or more additional excipients, wherein the composition is stable when stored between 20° C. to 25° C.±2° C. for at least about one month (aspect 120).

In aspects, the invention provides the method of aspect 120, wherein the composition further comprises any one or more of the characteristics of compositions described in any one or more of aspects 1-81 (aspect 121).

In aspects, the invention provides a method of detectably or significantly decreasing the healing time of a wound in a mammal suffering therefrom, the method comprising administration of a ready to use composition comprising (a) an ascorbic acid compound component which is (I) present in an amount of less than 350 mg, (II) present in a concentration of no more than 50 mg/mL, or (III) both (I) and (II), (b) at least one chelation agent, and (c) one or more additional excipients, wherein the composition is stable when stored between 20° C. to 25° C.±2° C. for at least about one month (aspect 122).

In aspects, the invention provides the method of aspect 122, wherein the composition further comprises any one or more of the characteristics of compositions described in any one or more of aspects 1-81 (aspect 123).

In aspects, the invention provides a ready-to-use pharmaceutical composition for the treatment of scurvy, wherein (a) all steps of the manufacturing process are performed under inert processing conditions; (b) the resulting product is stable when stored under wherein the composition is stable when stored at 20° C. to 25° C.±2° C. for at least about one month prior to use; and (c) the composition comprises any one or more additional characteristics described in any one or more of aspects 1-81 (aspect 124).

In aspects, the invention provides a ready-to-use pharmaceutical composition for the treatment of scurvy, wherein (a) the composition is manufactured by a non-aseptic process comprising terminal sterilization; (b) the resulting product is stable when stored at 20° C. to 25° C.±2° C. for at least about one month prior to use, and (c) the composition comprises any one or more additional characteristics described in any one or more of aspects 1-81 (aspect 125).

In aspects, the invention provides a ready-to-use pharmaceutical composition for the treatment of scurvy, wherein (a) the composition is manufactured by a process wherein all steps of the manufacturing process are performed under aseptic processing conditions; (b) the resulting product is stable when stored under wherein the composition can be stored at 20° C. to 25° C.±2° C. for at least about one month prior to use; and (c) the composition comprises any one or more additional characteristics described in any one or more of aspects 1-81 (aspect 126).

In aspects, the invention provides a ready-to-use pharmaceutical composition for the treatment of scurvy, wherein the composition is manufactured by (a) non-aseptically mixing a single chelating agent, an ascorbic acid compound, and optionally one or more tonicity agents with a sufficient amount of water to form a clear solution; (b) non-aseptically mixing one or more pH adjusting agents to establish a pH of about 5 to about 8; and (c) filling single-use containers with the resulting composition, wherein a terminal sterilization step is used to sterilize the final composition (aspect 127).

In aspects, the invention provides a ready-to-use pharmaceutical composition for the treatment of scurvy, wherein the composition is manufacture by (a) aseptically mixing a single chelating agent, an ascorbic acid compound, and optionally one or more tonicity agents with a sufficient amount of water to form a clear solution; (b) aseptically mixing one or more pH adjusting agents to establish a pH of about 5 to about 8; and (c) aseptically filling single-use containers with the resulting composition (aspect 128).

In aspects, provides stable ready-to-use pharmaceutical compositions of ascorbic acid or a pharmaceutically acceptable salt thereof, one or more tonicity agents and one or more pharmaceutically acceptable excipients, wherein the composition does not need any dilution prior to administration and can be stored at controlled room temperature (aspect 129).

In aspects, the invention provides the ready-to-use composition of aspect 129, wherein the ascorbic acid or a pharmaceutically acceptable salt thereof is ascorbic acid (aspect 130).

In aspects, the invention provides the ready-to-use composition of aspect 130, wherein the ascorbic acid or a pharmaceutically acceptable salt thereof present at a concentration between about 1 mg/mL to about 35 mg/mL (aspect 131).

In aspects, the invention provides the ready-to-use composition of aspect 131, wherein the ascorbic acid or a pharmaceutically acceptable salt thereof present at a concentration between about 25 mg/mL (aspect 132).

In aspects, the invention provides the ready-to-use composition of aspect 129, wherein the one or more tonicity agent(s) is selected from the group consisting of sodium chloride, dextrose, sucrose, xylitol, fructose, glycerol, sorbitol, mannitol, potassium chloride, mannose, calcium chloride, and magnesium chloride (aspect 133).

In aspects, the invention provides the ready-to-use composition of aspect 129, wherein the one or more tonicity agent(s) is in a concentration effective to impart osmolality of from 270 to 340 mOsm/kg (aspect 134).

In aspects, the invention provides the ready-to-use composition of aspect 129, wherein the one or more tonicity agent(s) is sodium chloride and dextrose (aspect 135).

In aspects, the invention provides the ready-to-use composition of aspect 135, wherein the sodium chloride present in an amount of about 0.1% w/v to about 0.9% w/v and or dextrose present in an amount of about 0.1% w/v to about 5% w/v (aspect 136).

In aspects, the invention provides the ready-to-use composition of aspect 129, wherein the composition is administered by a parenteral route of administration such as intravenous administration, subcutaneous administration, intramuscular administration, intra-atrial administration, or intra-arterial continuous infusion to a patient (aspect 137).

In aspects, the invention provides the ready-to-use composition of aspect 129, wherein the one or more pharmaceutically acceptable excipients are selected from chelating agents, stabilizing agents, buffers, pH adjusting agents, antioxidants, preservatives, and water or suitable solution for dilution (aspect 138).

In aspects, the invention provides the ready-to-use composition of aspect 129, wherein controlled room temperature is between 20° to 25°±2° C. (aspect 139).

In aspects, the invention provides ready-to-use pharmaceutical compositions for parenteral administration comprising: (a) ascorbic acid or a pharmaceutically acceptable salt thereof in a concentration between about 1 mg/mL to about 35 mg/mL, (b) ascorbic acid or a pharmaceutically acceptable salt thereof in a concentration between about 1 mg/mL to about 35 mg/mL, (c) one or more tonicity agents in a concentration of about 0.1% w/v to about 5% w/v, (d) a chelating agent in a concentration of about 0.001% w/v to about 0.1% w/v, (e) water, and (f) one or more buffers or pH-adjusting agents (aspect 140).

In aspects, the invention provides the ready-to-use composition of aspect 140, wherein the composition does not need any dilution prior to administration and can be stored at controlled room temperature (aspect 141).

In aspects, the invention provides the ready-to-use composition of aspect 140, wherein the one or more tonicity agent is sodium chloride and/or dextrose (aspect 142).

In aspects, the invention provides the ready-to-use composition of aspect 141, wherein the sodium chloride present in an amount of about 0.1% w/v to about 0.9% w/v and or dextrose present in an amount of about 0.1% w/v to about 5.0% w/v (aspect 143).

In aspects, the invention provides the ready-to-use composition of aspect 140, wherein the chelating agent is edetate disodium (aspect 144).

In aspects, the invention provides the ready-to-use composition of aspect 140, wherein the buffers or pH-adjusting agents selected from the group consisting of sodium bicarbonate, hydrochloric acid, sodium hydroxide and a mixture thereof (aspect 145).

It is to be understood that the above description is intended to be illustrative and not restrictive. Many aspects will be apparent to those of skill in the art upon reading the above description. The scope of the invention should, therefore, be determined with reference to the appended claims, along with the full scope of equivalents to which such claims are entitled.

EXAMPLES

The following detailed Examples of certain aspects of the invention are provided to assist readers in further understanding aspects of the invention or principles related to practicing aspects of the invention. Any particular materials, methods, steps, and conditions employed/described in the following Examples, and any results thereof, are intended to further illustrate aspects of the invention. These Examples reflect exemplary embodiments of the invention, and the specific methods, findings, principles of such Examples, and the general implications thereof, can be combined with any other aspect of the invention. However, readers should understand that the invention is not limited by or to any part of the Examples.

The following Example 1 and Example 2 are prophetic Examples, describing compositions and manufacturing processes of the same.

Example 1—Ready-to-Use Ascorbic Acid Injection—Formulation A

TABLE 1

| Formulation A | | |
| --- | --- | --- |
| Sr. No | Ingredient | Quantity/mL |
| 1 | Ascorbic acid | 25 mg/mL |
| 2 | Edetate Disodium | 0.001% w/v to 0.1% w/v |
| 3 | Sodium Hydroxide | 0.1% to 15% w/v |
| 4 | Sodium Chloride | 0.1% to 0.9% w/v |
| 5 | Dextrose | 0.1% to 5% w/v |
| 6 | Sodium bicarbonate/Hydrochloric acid | QS for pH adjustment |
| 7 | Water for Injection | QS to volume adjustment |

A composition according to Formulation A shown in Table 1 (above) is manufactured according to the following process, under varying conditions. In one experiment, the following process is conducted under aseptic conditions. In a second experiment, the following process is conducted under non-aseptic conditions and the process comprises a terminal sterilization step.

A sufficient quantity of water for injection (WFI) is collected in a suitable compounding vessel.

The total required quantity of each of disodium edetate, ascorbic acid, and sodium chloride, dextrose, or sodium chloride and dextrose is weighed out and each ingredient is added under continuous stirring.

The resulting composition is stirred until all ingredients are completely dissolved.

The total required quantity of sodium hydroxide is then added and stirred until completely dissolved.

The pH of the solution is then measured, and the pH of the solution adjusted as necessary with sodium bicarbonate and/or hydrochloric acid to a pH of about 5 to about 8, targeting a pH of about 5.6 to about 6.6.

The composition, in the form of a solution, is then brought up to a final target volume with remaining water for injection (WFI).

In experiments wherein the steps of the manufacturing process described in this Example are conducted under non-aseptic processing conditions, the solution is subjected to a terminal sterilization step.

The final solution is filled into suitable containers, such as 2 mL, 4 mL, 6 mL, 8 mL, or 10 mL containers (e.g., glass vials) or combinations thereof.

The final solution is expected to have an osmolality of between about 270 mOsm/kg to about 340 mOsm/kg.

The final solution is expected to have a pH of between about 5 to about 8, such as between about 5.6 to about 6.6 according to the pH adjustment step above.

The resulting composition is then used in stability studies and stability assessment assays such as those described herein.

Example 2—Ready-to-Use Ascorbic Acid Injection—Formulation B

TABLE 2

Formulation B

| Sr. No | Ingredient | Quantity/mL |
|---|---|---|
| 1 | Sodium Ascorbate | 28.1 mg/mL equivalent to 25 mg/mL ascorbic acid |
| 2 | Edetate Disodium | 0.001% w/v to 0.1% w/v |
| 3 | Sodium Bicarbonate | 0.1% to 1.5% w/v |
| 4 | Sodium Chloride | 0.1% to 0.9% w/v |
| 5 | Dextrose | 0.1% to 5% w/v |
| 6 | Sodium hydroxide/Hydrochloric acid | QS for pH adjustment |
| 7 | Water for Injection | QS to volume adjustment |

A composition according to Formulation B shown in Table 2 is manufactured according to the following process. In one experiment, the composition is manufactured under aseptic processing conditions. In another experiment, the composition is manufactured under non-aseptic processing conditions and the manufacturing process comprises a terminal sterilization step. In Formulation B, each mL of the exemplary composition contains 28.1 mg of sodium ascorbate, equivalent to 25 mg of ascorbic acid.

A sufficient quantity of water for injection (WFI) is collected in a suitable compounding vessel.

The total required quantity of each of disodium edetate, ascorbic acid, and sodium chloride, dextrose, or sodium chloride and dextrose is weighed out and each ingredient is added under continuous stirring.

The resulting composition is stirred until all ingredients are completely dissolved.

The total required quantity of sodium bicarbonate is then added and stirred until completely dissolved.

The pH of the solution is then measured, and the pH adjusted as necessary with sodium hydroxide and/or hydrochloric acid to a pH of about 5 to about 8, targeting a pH of about 5.6 to about 6.6.

The composition, in the form of a solution, is brought up to a final target volume with remaining water for injection (WFI).

In experiments wherein the steps of the manufacturing process described in this Example are conducted under non-aseptic processing conditions, the solution is subjected to a terminal sterilization step.

The final solution is filled into suitable containers, such as 2 mL, 4 mL, 6 mL, 8 mL, or 10 mL containers (e.g., glass vials) or combinations thereof.

The final solution is expected to have an osmolality of between about 270 mOsm/kg to about 340 mOsm/kg.

The final solution is expected to have a pH of between about 5 to about 8, such as between about 5.6 to about 6.6 according to the pH adjustment step above.

The resulting composition is then used in stability studies and stability assessment assays such as those described herein.

What is claimed is:

1. A method of treating a disease related to vitamin C deficiency, the method comprising (a) providing an injectable pharmaceutically acceptable composition in a container component, the composition comprising an effective unit dose amount of an ascorbic acid compound component in a concentration of about 20 mg/ml— about 50 mg/mL and one or more excipients, wherein the one or more excipients comprise (1) a chelation component consisting of an ethylenediaminetetraacetic acid (EDTA) compound or a suitable EDTA salt, (2) an antioxidant component consisting of a single antioxidant compound, and (3) a buffer in a concentration of between 1-1.5%; wherein there are no additional excipients present in the composition that exhibit antioxidant activity and the composition is contained in the container component in ready-to-use form, wherein the composition has an osmolality of about 270 mOsm/kg to about 340 mOsm/kg and is stable when stored at 20° C. to 25° C.±2° C. for at least 3 months prior to use, (b) directly administering an effective amount of the composition by parenteral administration to a subject having a vitamin C deficiency, and (c) if necessary, repeating steps (a) and (b) for a number of times effective to treat a vitamin C deficiency in the subject.

2. The method of claim 1, wherein the disease is scurvy.

3. The method of claim 1, wherein the parenteral administration comprises injection or intravenous infusion.

4. The method of claim 3, wherein the parenteral administration is intravenous infusion.

5. The method of claim 1, wherein the ascorbic acid compound component is at least 50% composed of sodium ascorbate.

6. The method of claim 1, wherein the concentration of the ascorbic acid compound component in the composition is about 25 mg/mL.

7. The method of claim 1, wherein the container comprises about 2 mL-about 10 mL of the composition.

8. The method of claim 1, wherein the ratio of the ascorbic acid compound component to the chelation component is less than or equal to 1:0.00018 w/v.

9. The method of claim 8, wherein the chelation component is present in a concentration of about 0.0005% w/v to about 0.15% w/v of the composition.

10. The method of claim 1, wherein the one or more excipients further comprise a tonicity component comprising one or more tonicity agent(s) selected from a group comprising sodium chloride, dextrose, sucrose, xylitol, fructose, glycerol, sorbitol, mannitol, potassium chloride, mannose, calcium chloride, magnesium chloride, and combinations of any two or more thereof.

11. The method of claim 10, wherein the tonicity component comprises sodium chloride, dextrose, or both sodium chloride and dextrose.

12. The method of claim 10, wherein the ratio of the ascorbic acid compound component to the total tonicity agent component in the composition is about 1:50 to about 1:0.018 w/v.

13. The method of claim 11, wherein the composition comprises sodium chloride in a concentration of about 0.1% w/v to about 0.9% w/v and dextrose in a concentration of about 0.1% w/v to about 5% w/v.

14. The method of claim 1, wherein the composition is stable when stored at 20° C. to 25° C.±2° C. for at least 12 months prior to use.

15. The method of claim 1, wherein part (c) of the method comprises repeating steps (a) and (b) at least two times.

16. The method of claim 15, wherein part (c) of the method comprises repeating steps (a) and (b) at least once per day for a period of about 2 days to about 7 days.

17. The method of claim 1, wherein the composition is stable when stored at 20° C. to 25° C.±2° C. for at least 6 months prior to use.

* * * * *